(12) United States Patent
Muhie et al.

(10) Patent No.: US 11,618,922 B2
(45) Date of Patent: Apr. 4, 2023

(54) BIOMARKERS OF IMMUNE DYSFUNCTION IN RESPONSE TO CHRONIC STRESS, METHODS OF USE AND DIAGNOSTIC KITS

(71) Applicant: The Government of the United States, As Represented by the Secretary of the Army, Fort Detrick, MD (US)

(72) Inventors: Seid Muhie, Greenbelt, MD (US); Marti Jett, Washington, DC (US); Rasha Hammamieh, Gaithersburg, MD (US)

(73) Assignee: The Government of the United States, as Represented by the Secretary of the Army, Fort Detrick, MD (US)

( * ) Notice: Subject to any disclaimer, the term of this patent is extended or adjusted under 35 U.S.C. 154(b) by 520 days.

(21) Appl. No.: 14/121,808

(22) Filed: Oct. 20, 2014

(65) Prior Publication Data

US 2015/0051094 A1    Feb. 19, 2015

Related U.S. Application Data

(63) Continuation of application No. PCT/US2013/000097, filed on Mar. 29, 2013.

(60) Provisional application No. 61/687,731, filed on Apr. 28, 2012.

(51) Int. Cl.
*C12Q 1/6883* (2018.01)
*C12Q 1/6837* (2018.01)
*C12Q 1/6809* (2018.01)

(52) U.S. Cl.
CPC ......... *C12Q 1/6883* (2013.01); *C12Q 1/6809* (2013.01); *C12Q 1/6837* (2013.01); *C12Q 2600/158* (2013.01)

(58) Field of Classification Search
CPC .................. C12Q 1/6883; C12Q 2600/158
See application file for complete search history.

(56) References Cited

U.S. PATENT DOCUMENTS

2012/0094859 A1* 4/2012 Redei .................. C12Q 1/6883
                                                                506/9

OTHER PUBLICATIONS

Muhie (2007) "Host Gene Expression Responses to Dengue, Plague and *Staphylococcus* Enterotoxin B in the Presence and Absence of Severe Physiological Stress" dissertation, Georgetown University, ISBN 9780549939672 http://pqdtopen.proquest.com/pubnum/3339919.html.*
Shippee et al. (1994) Nutritional and Immunological Assessment of Ranger Students with Increased Caloric Intake. No. USARIEM-T95-5. Army Research Inst of Environmental Medicine Natick MA.*
Hughes et al. (2001) "DNA microarrays for expression profiling" Current Opinion in Chemical Biology 5(1):21-25.*

(Continued)

*Primary Examiner* — Jeremy C Flinders
(74) *Attorney, Agent, or Firm* — McBee Moore & Vanik IP, LLC

(57) ABSTRACT

Diagnostic biomarkers for diagnosing immune suppression/dysfunction. The diagnostic biomarkers are genes and/or transcripts that are up or down regulated compared to normal expression when a subject has been stressed either mentally and/or physically. The invention also relates to a method of detecting comprised or suppressed immune response in a subject by comparing certain diagnostic biomarkers in the subject to a control set of diagnostic biomarkers.

5 Claims, 30 Drawing Sheets

(56) References Cited

OTHER PUBLICATIONS

Yoo et al. (J. Microbiol. Biotechnol., 2008, 19(7):635-646) (Year: 2008).*
Statnikov et al. (Bioinformatics, 2005, 21(5):631-643) (Year: 2005).*
George-Gay et al. (Journal of PeriAnesthesia Nursing, 2003, 18(2):96-117) (Year: 2003).*
Kanno et al. (BMC Genomics, 2006, 7(64):1-14) (Year: 2006).*
Lyons et al. (BMC Genomics, 2007, 8:64, doi:10.1186/1471-2164-8-64) (Year: 2007).*
Affymetrix (GeneChip® Human Genome U133 Plus 2.0 Array datasheet, 2004) (Year: 2004).*
Invitrogen (Handbook for Dynabeads® and mRNA DirectTM Micro Kit, 2007) (Year: 2007).*
Cohen, et al., Psychological stress and disease. JAMA 2007;298(14):1685-1687.
Rokutan, et al., Gene expression profiling in peripheral blood leukocytes as a new approach for assessment of human stress response.,J Med Invest 2005; 52(3-4):137-144.
Motoyama et al., Isolation stress for 30 days alters hepatic gene expression profiles, especially w/ reference to lipid metabolism in mice, Physiol Genomics 2009; 37(2):79-87.
Zhang et al., Chronic restrain stress promotes immune suppression through toll-like receptor 4-mediated phosphoinositide 3-kinase signaling, J Neuroimmunol 2008;204(1-2);13-19.
Padgett, et al., Haw stress influences ths immune response; Trends in Immunology 2003;24(8),444-448.
Kiecolt-Glaser, et al., Chronic stress alters the immune response to influenza virus vaccine in older adults; Pro Nat Acad Sci (USA) 1996;93(7);3043-3047.
Tournier, et al., Chronic restraint stress induces severe disruption of the T-cell 3 specific response to tetanus toxin vaccine, immunology 2001;102(1);87-93.
Li, et al., Effects of chronic stress and interleukin-10 gene polymorphisms on antibody response to tetanus vaccine . . . , Psychosom Med 2007;69(6): 551-559.
Glaser, et al., Chronic stress modulates the immune response to a pneumococcal pneumonia vaccine, Psychosom Med 2000; 62(6): 804-807.
Kiank, et al., Stress susceptibility predicts the severity of immune depression and the failure to combat bacterial infection . . . ; Brain Behav Immun 20(4):359-368, (2006).
Reiche, e tal., Stress, depression, the immune system, and cancer; Lancet Oncol 2004; 5(10):617-625.
Freidl, et al., Endocrine markers of semistravation in healthy lean men in a multistressor environment; J Appl Physiol 2000; 88(5): 1820-1830.
Nindl, et al.,Physiological consequences of U.S. Army Ranger training; Med Sci Sprots Exerc 2007; 39(8): 1380-1387.
Mendis, et al, Transcriptional response signature of human lymphoid cells to *staphylococcal* enterotoxin B. Genes Immun 2005; 6(2):84-94.
Paik, et al., Psychological stress may induce increased humoral and decreased cellular immunity; Behav Med 2000; 26(3): 139-141.
Glaser, et al., Evidence for a shift in the Th-1 to Th-2 cytokine response asociated w/ chronic stess and aging; J Gerontol ser A-Biol Sci Med Sci 2001; 56(8); M477-M482.
O'Connell, et al., MicroRNA-155 promotes autoimmune inflammation by enhancing inflammatory T cell development; Immunity; 33(4): 607-619, (2010).
Kurowska-Stolarska, et al., MicroRNA-155 as a proinflammatory regulator in clinical and experimental arthritis; Proc Natl Acad Sci USA; 108(27): 11193-11198, (2011).
Das, et al., Early indicators of exposure to biological threat agents using host gene profiles in peripheral blood mononuclear cells; BMC Infect Dis 2008; 8: 104.
Marinescu, et al., The MAPPER database: a multi-genome catalog of putative transcription factor binding sites. In: Nucleic Acids Res pp. D91-D97, (2005).
Christin, et al., A critical assessment of feature selection methods for biomarker discovery in clinical proteomics; Mol Cell Proteomics; 12(1): 263-276, (2013).
Wang, et al., Improved centroids estimation for the nearest shrunken centroid classifier; Bioinformatics 2007; 23(8): 972-979.
Tibshirani, et al., Diagnosis of multiple cancer types by shrunken centroids of gene expression; Proc Natl Acad Sci USA 2002; 99(10): 6567-6572.
Sharma, et al., Early detection to breast cancer based on gene-expression patterns in peripheral blood cells. Breast Cancer Res 2005; 7(5): R634-644.
Shankavararn, et al, Transcript and protein expression profiles of the NCI-60 cancer cell panel: an integromic microarray study; Mol Cancer Ther 2007; 6(3): 820-832.
Selaru, et al., Beyond field effect: Analysis of shrunken centroids in normal esophageal epithelia detects concomitant esophageal . . . ; Bioinform Bio Insights 2007; 1: 127-136.
Suarez-Farinas, et al., Personalized medicine in psoriasis: developing a genomic classifier to predict histological response io Alfacept; BMC Dermatol; 10: 1, (2010).

* cited by examiner

Displaying 1983 entities out of 8968 satisfying corrected p-value (Benjamini Hochberg FDR) cut-off 0.05.

| Differential Expression Analysis Report | | | | | | |
|---|---|---|---|---|---|---|
| Test Description | | | | | | |
| Selected Test:    TTest unparied unequal variance (Welch)<br>p-value computation:    Asymptotic<br>Multiple Testing Correction:   Benjamini-Hochberg | | | | | | |
| Result Summary | | | | | | |
|  | p all | p < 0.05 | p < 0.02 | p < 0.01 | p < 0.0050 | p < 0.0010 |
| FC all | 8968 | 1983 | 1181 | 820 | 575 | 288 |
| FC > 1.1 | 7120 | 1983 | 1181 | 820 | 575 | 288 |
| FC > 1.5 | 1725 | 1396 | 1011 | 759 | 557 | 288 |
| FC > 2.0 | 434 | 423 | 402 | 369 | 332 | 225 |
| FC > 3.0 | 109 | 109 | 107 | 102 | 98 | 87 |
| Expected by chance |  | 99 | 23 | 8 | 2 | 0 |

FC = Fold Change

BIOMARKERS OF IMMUNE DYSFUNCTION IN RESPONSE TO CHRONIC STRESS, METHODS OF USE AND DIAGNOSTIC KITS

This application claims priority and is a continuation application of PCT application no. PCT/US2013/000097 filed Mar. 28, 2013, pending, which claims priority of U.S. provisional application No. 61/687,731 filed Apr. 28, 2012.

GOVERNMENT INTEREST

The invention described herein may be manufactured, used and licensed by or for the U.S. Government.

BACKGROUND OF THE INVENTION

1 Field of the Invention

The present invention relates to diagnostic biomarkers of immune suppression/dysfunction. The diagnostic biomarkers may be used to evaluate the capability of immune cells in subjects, and screen subjects for immune suppression/dysfunction in response to stress and/or pathogen exposure.

The present invention further relates to diagnostic biomarkers suitable for diagnosing *Staphylococcus* Enterotoxin B (SEB) exposure in a subject, and methods of using the same. These diagnostic biomarkers are suitable for diagnosing SEB exposure in the presence of comprised immune response or stress.

SUMMARY OF THE INVENTION

Diagnostic biomarkers for diagnosing immune suppression/dysfunction. The diagnostic biomarkers are transcripts that are up or down regulated compared to normal expression when a subject has been stressed either mentally and/or physically. The invention also relates to a method of detecting comprised or suppressed immune response in a subject by comparing certain diagnostic biomarkers in the subject to a control set of diagnostic biomarkers.

BRIEF DESCRIPTION OF THE FIGURES

FIG. 2A is a table showing the analysis of differentially expressed genes in leukocytes of Ranger Trainees before and after Training;

Figure 15:
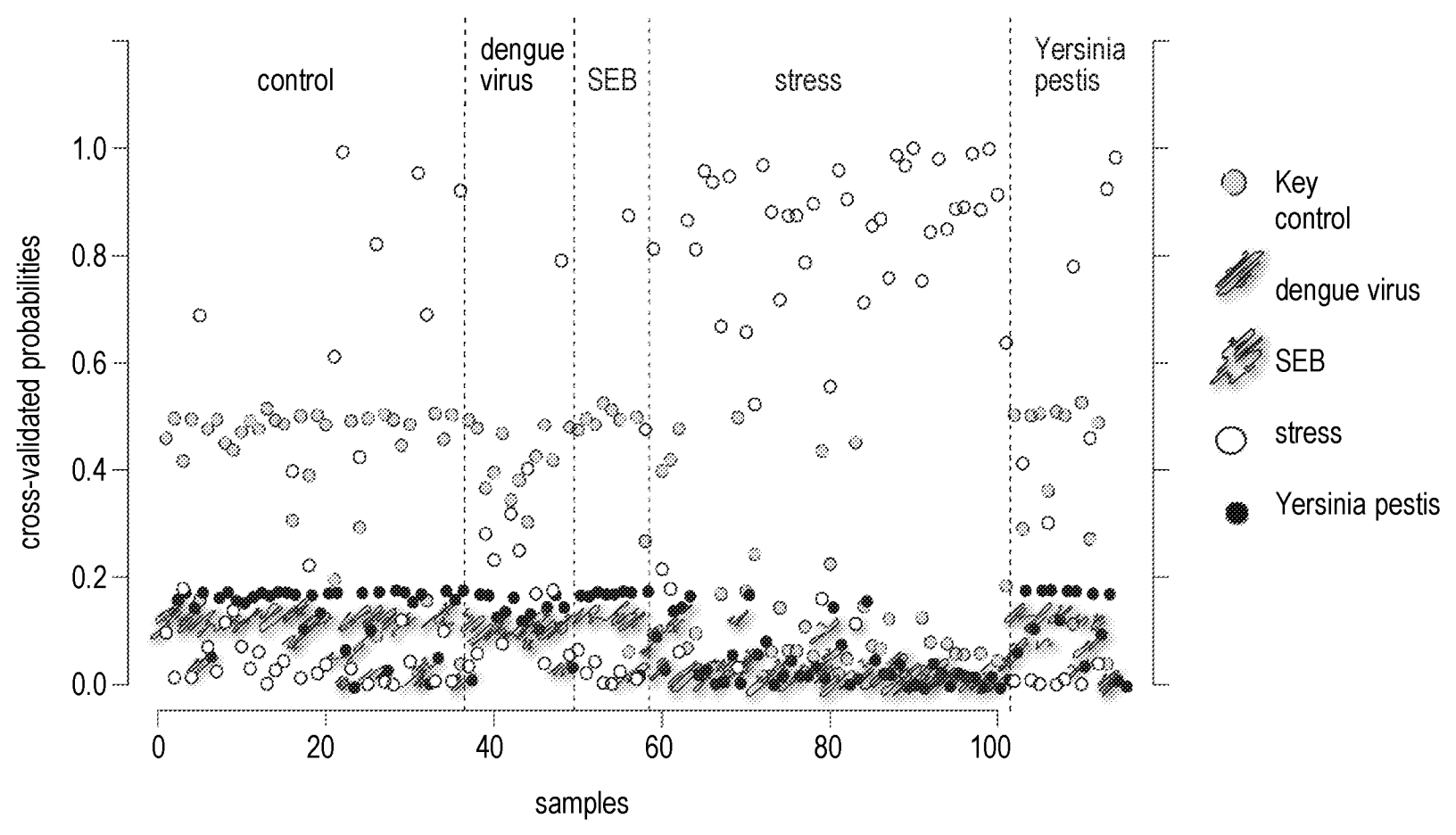

FIG. 15 is a graph showing cross-validation of the prediction analysis of the invention.

DETAILED DESCRIPTION

Figure 1A:
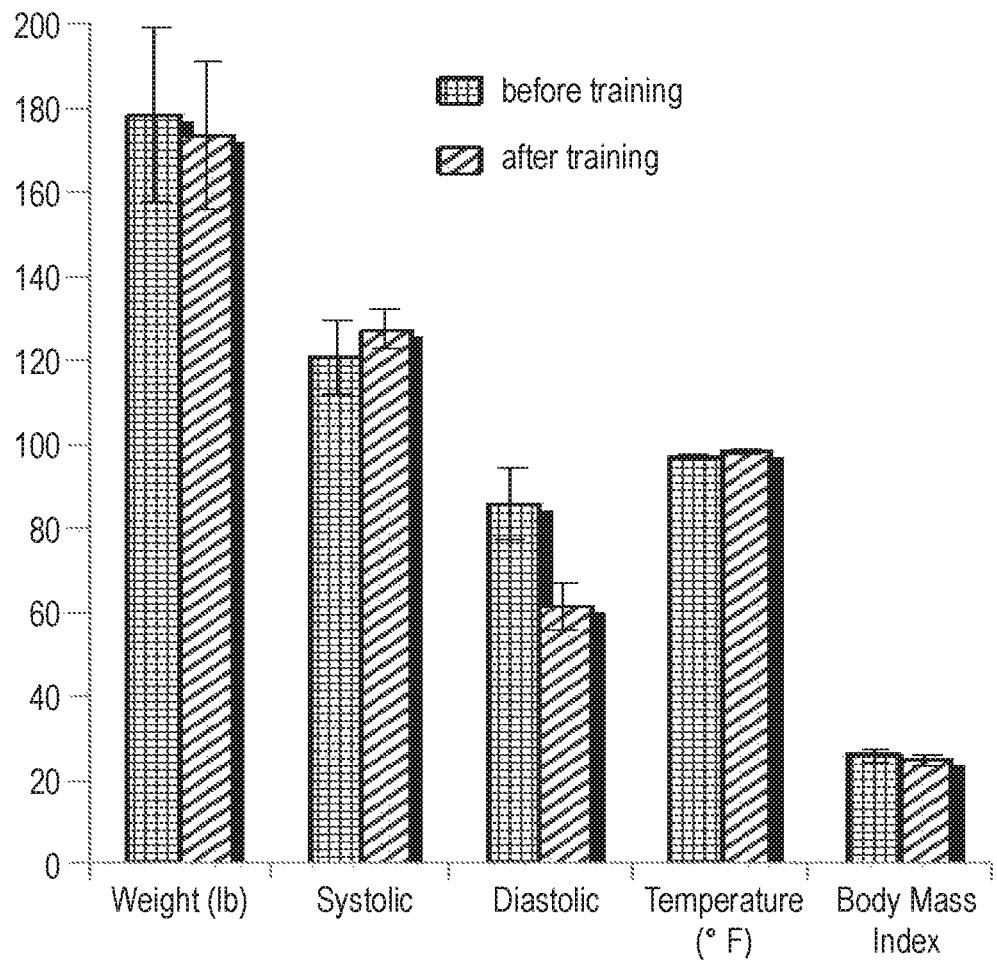
FIG. 1A is a graph showing comparisons of before and after training of weights, temperatures and blood pressures of cadets.

Previous studies suggest that excessive or prolonged stress impairs protective immunity towards infection leading to increase susceptibility to illness. Comprehensive molecular explanations of the host's physiological stress response and the results of failed adaptation over time offer the potential to identify the debilitating pathophysiologic consequence of severe stress on health. More importantly, molecular approaches offer the opportunity to implement clinical strategies to differentiate immune impaired individuals from their normal counterparts.

Applicants examined the effects of long-term battlefield-like stressors of U.S. Army Ranger Training on genome wide expression profiles for biomarker identification of prolonged severe, stress-induced, compromised immune response. Applicants identified 59 differentially regulated transcripts using comparative Welch's T-test along with Bonferroni correction (q<0.01) followed by 3-fold change. These 59 differentially regulated transcripts are identified at Table 3 herein. Among the 59 differentially regulated transcripts identified, 48 were down regulated and 11 were up regulated. Most of the down-regulated transcripts were directly involved in protective immunity.

Differentially regulated transcripts identified and their cognate pathways were confirmed using quantitative real-time PCR arrays. Antigen preparation and presentation, chemotaxis, inflammation, and activation of leukocytes were among overrepresented immune response processes that were significantly associated with suppressed transcripts. Differentially regulated transcripts identified or genes from their corresponding pathway can serve as diagnostic biomarkers to differentiate/identify individuals with stress-induced immune suppression. cDNAs of some of these transcripts can be electrochemically tethered in the wells of micro- or nano-chips for quick diagnosis purpose.

Diagnostic biomarkers within the scope of the present invention for use in identifying or screening individuals for immune suppression/dysfunction include five (5) or more, seven (7) or more, or ten (10) or more of the 59 differentially regulated transcripts identified herein or genes from their corresponding pathway. For example purposes, Applicants provide herein a subset of 14 of the 59 transcripts that can be used as a single batch of biomarkers (see Table 3A and 3B). The five (5) or more, seven (7) or more, ten (10) or more or twenty (20) or more of the differentially regulated transcripts or genes from their corresponding pathway may, for example, be selected from these. It is understood to one of ordinary skill in the art that there may be additional biomarkers, not yet identified, that can be used to screen individuals for immune suppression/dysfunction. This invention is not limited to the 59 biomarkers listed in Table 3.

These diagnostic biomarkers would be useful to diagnose immune suppression/dysfunction in a subject due to stress. The present invention further relates to diagnostic kits for use in screening immune function of a subject, where the kit employs the diagnostic biomarkers identified herein.

Applicants further conducted studies on the effect of stress on a patient's ability to respond to other pathogens. More specifically, Applicants studied the effect of *Staphylococcus* Enterotoxin B (SEB) on host response gene expression profiles, and identified genes that showed consistent differential expression towards SEB whether or not the host had been exposed to stress. These transcripts or genes from their corresponding pathway were SEB-specific (independent of the physiologic and pathologic status of the host), and may serve as diagnostic markers of SEB exposure.

Therefore, this invention proposes a simple test to identify the capability of immune cells to respond to pathogenic agents in military personnel. This biomarker profile would allow for a semi-quantitative method to evaluate the immune system in terms of gene expression.

Transcriptomic Characterization of Immune Suppression from Battlefield-Like Stress This invention identifies changes in transcriptome of human due to battlefield-like stress. Thorough understanding of stress reactions is likely to produce better strategies to manage stress, and improve health[1]. Stress modulates gene expression, behavior, metabolism and immune function[2-5]. Chronic physiological and psychological stresses are major contributors of stress-induced suppression of protective immunity. For example, chronic stress impairs lymphocyte proliferation, vaccination efficacy[6-9], NK cell activity, resistance to bacterial and viral infection[10], and increases risk of cancer[11].

Yet, comprehensive descriptions of molecular responses to stress are needed to fully understand modulated networks and pathways, and hence to reduce and prevent pathophysiologic effects of intense and prolonged stresses.

Here we report gene expression changes occurring in leukocytes collected from Army Ranger Cadets before and after eight-week Ranger Training. Ranger cadets are exposed to different and extreme physical and psychological stressors of Ranger Training Course, which is designed to emulate extreme battlefield scenarios: sleep deprivation, calorie restriction, strenuous physical activity, and survival emotional stresses—pushing cadets to their physical and psychological limits. The Ranger population provides a rare opportunity to study intense chronic battlefield-like stress, and to contribute to the understanding of intense chronic stress in general. Ranger Training has been shown to impair cognitive function, cause significant declines in 3,5,3'-triiodothyroxine and testosterone, and increase cortisol and cholestero[12; 13].

Transcriptomic alterations, in this study, were assayed using cDNA microarrays. Results were corroborated with oligonucleotide, microRNAs, and real-time QPCR arrays, and were confirmed using Quantitative RT-PCR and ELISA. Analyses of functional and regulatory pathways of differentially altered transcripts revealed suppression of immune processes due to battlefield-like stress. Some of stress induced microRNAs, and a number of stress inhibited transcription factors were found to regulate or be modulated by many compromised immune response transcripts. Suppressed immune response genes remained suppressed even after exposure of post-stress leukocytes to mitogenic toxin, SEB. This impaired activation is a clear indicator of anergy, and compromised protective immunity.

Results

Ranger Trainees experience an average daily calorie deficit of 1000-1200 kcal, restricted and random sleep of less than 4 hours per day, strenuous and exhaustive physical toiling and emotional survival stressors. Five of the initial fifteen Trainees enrolled in our study were replaced with five others due to attrition (to maintain 15 study subjects at both time points). All study subjects had complete and differential blood counts performed, and were observed for infections and injuries. By the end of training, Trainees showed significant average weight loss, decreased body mass index and diastolic blood pressure, and significant increase in average body temperature and systolic blood pressure (FIG. 1A); and they showed metabolite patterns typical of severe stress. The vertical lines show the ranges of cell counts. (Normal Ranges are WBC 5-12×10³/mm³; NEU 2-8×10³/mm³; LYM 1-5×10³/mm³; MON 0.1-1×10³/mm³; EOS 0.0-0.4×10³/mm³; BAS 0.0-0.2×10³/mm³.)

Figure 1B:
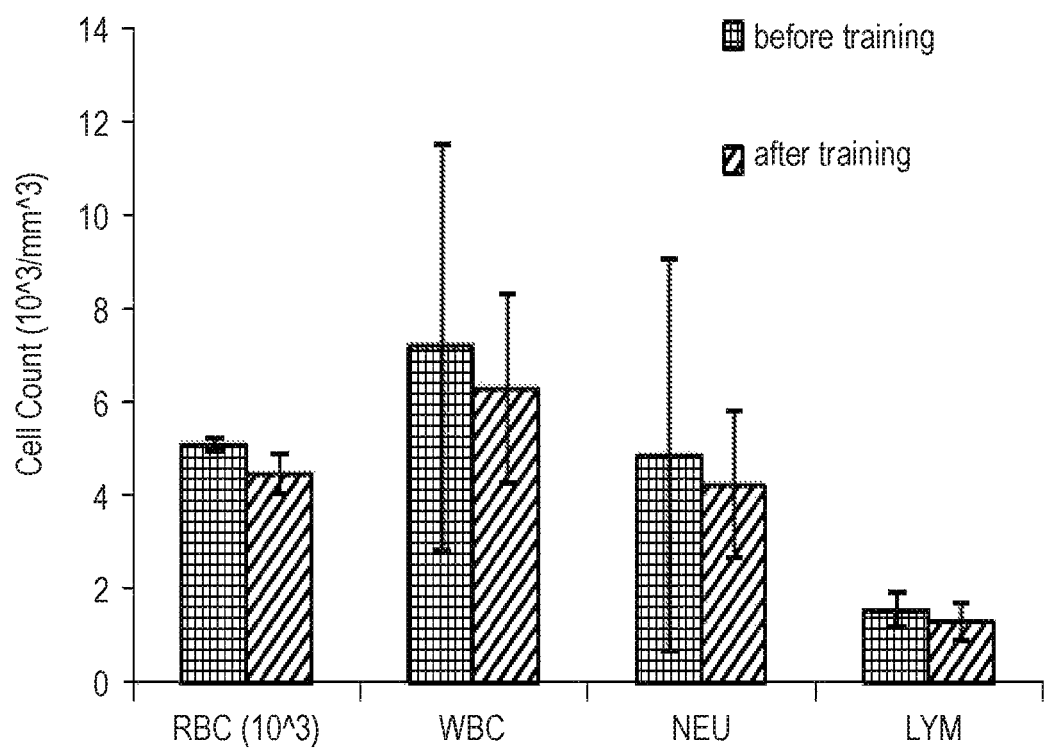
FIG. 1B is a graph showing differential and complete leukocyte counts of trainees before and after training including complete and differential blood counts for pre- and post-Training subjects that include red blood cells, white blood cells, neutrophils and lymphocytes; monocytes, eosophils and basophils.
Figure 1C:
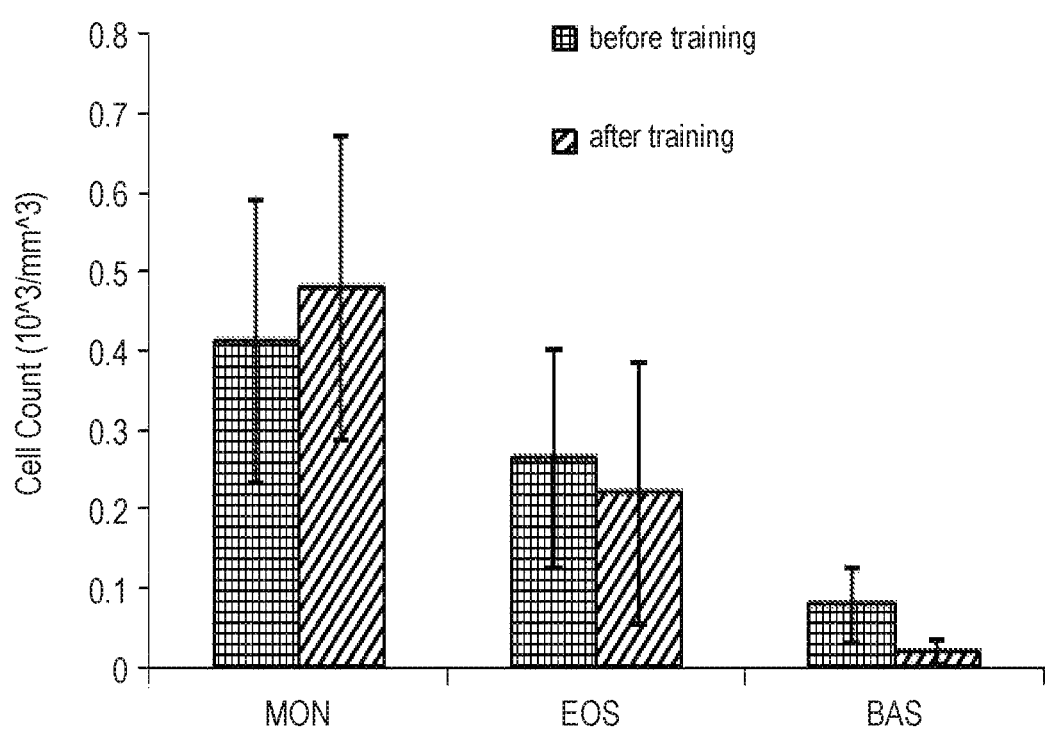
FIG. 1C is a graph showing differential and complete leukocyte counts of trainees before and after training that include complete and differential blood counts for pre- and post-Training subjects included monocytes, eosophils and basophils.

Differential and complete blood counts showed small but significant differences between pre- and post-Training cells, yet all were within normal ranges (FIGS. 1B and 1C). To normalize for cell count differences, equal number of pre- and post-Training leukocytes were used for isolation of RNA, and equal amounts of isolated RNAs were used for microarrays, and RT-QPCR assays.

As shown in FIGS. 1B-1C, differential and complete leukocyte counts of soldiers before and after RASP are presented. Differential and complete blood counts for pre- and post[RASP subjects included red blood cells (RBC), white blood cells (WBC), neutrophils (NEU), lymphocytes (LYM), monocytes (MON), eosinophils (EOS) and baseophils, (BAS). Using comparative t-test, only RBC (P<0.006) and BAS (p<0.02) were significantly changed (reduced) after RASP. The ranges of cell counts including RBC and BAS (shown by the vertical lines) were within normal ranges. Normal ranges are WBC5-12×10$^3$ mm$^{-3}$; NEU 2-8×10$^3$ mm$^{-3}$; LYM 1-5×10$^3$ mm$^{-3}$; MON 0.1-1×10$^3$ mm$^{-3}$; EOS 0.0-0.4×10$^3$ mm$^{-3}$; BAS 0.0-0.2×10$^3$ mm$^{-3}$.

Transcriptome Profiling of Pre- and Post-Training Leukocytes

We used three transcriptome profiling techniques to cross-validate our findings: cDNA and oligonucleotide microarrays, and quantitative real time PCR arrays. Expression profiles were done on total RNAs isolated using two different methods: Trizol (Invitrogen. Inc) and PAXgene, (Qiagen.Inc).

cDNA Microarrays Analyses

To analyze gene expression profiles of leukocytes of Ranger Cadets collected before and after eight-week Training, we used custom cDNA microarrays that contained ~10 000 well-characterized cDNA probes of 500 to 700 base pairs representing ~9 000 unique human gene targets.

Figure 2B:
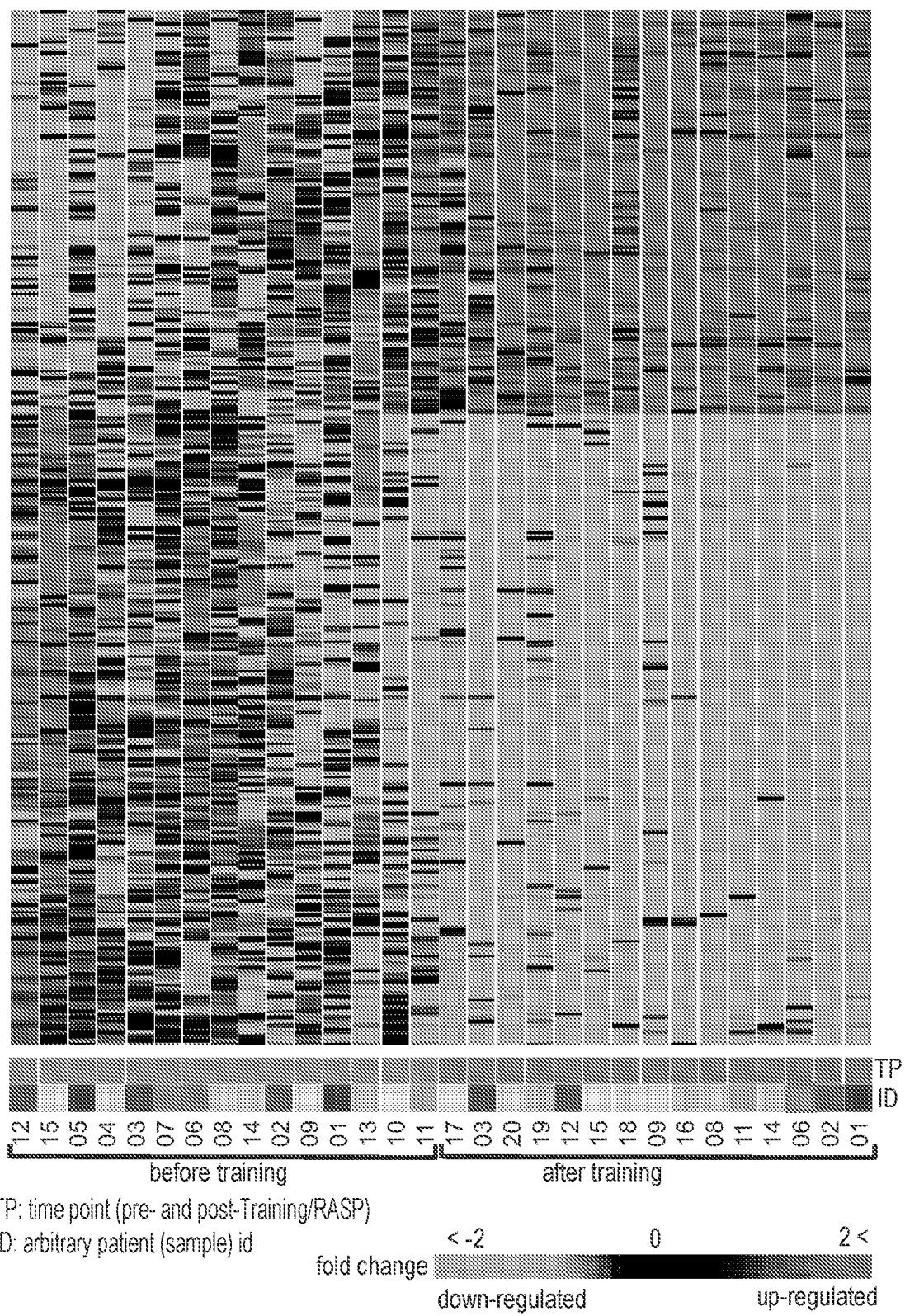
FIG. 2B is a heat map that shows Hierarchical clustering of 288 genes that passed Welch's t-test with FDR correction (q<0.001) and had expression alteration of ≥1.5 fold with each lane showing the 288 genes and their leukocyte expression level for each subject before (left panel) or after (right panel) training in comparison to human universal RNA.

Welch's (unpaired unequal variance) t-test along with false discovery rate (FDR) correction was used on normalized expression data to identify 1 983 transcripts that were significantly changed (q≤0.05), with 1 396 showing ≥1.5 fold change in expression level between pre- and post-Training samples (Table 4). Among 1 396 differentially regulated genes, 288 genes FIG. 2B were significantly changed at q≤0.001, and 87 of these were differentially regulated by >3-fold change. Of these 87 genes, 72 were down-regulated, and 68 of 72 genes have direct role in immune response, including 23 of the 25 most down-regulated genes. These results strongly suggest that Ranger Training stressors suppress the immune response, and this finding was corroborated by functional and pathway enrichments.

Functional enrichments of significantly regulated genes using both hypergeometric test (FDR correction, q≤0.05), and Fishers exact test identified the immune system as the most affected biological process. Apoptosis, stress response, response to wounding, metabolism, hormone receptor signaling (peptide and steroid), cell cycle and unfolded protein response signaling were also significantly associated with altered transcripts. Yet, immune system process was most significantly over-represented (q<1.7E-16), and was associated with 177 differentially regulated genes. Of the 177 genes, 151 were down-regulated, and 26 were up-regulated. Further functional enrichment of the 151 genes indicated that these genes were significantly associated with microbial recognition, inflammation, chemotaxis, antigen presentation, and activation of lymphocytes, mast cells and macrophages (Tables 1). The 26 Up-regulated immune response genes were associated with response to steroid hormone stimulus, regulation of leukocyte activation, complement activation, negative regulation gene expression, and negative regulation of phosphorylation (Table 1).

TABLE 1

Functions significantly associated with differentially regulated immune response genes that passed Welch's t-test and FDR correction (q < 0.05 and showed >1.3 fold change in post RASP leukocyted compared with pre-RASP leukocytes.

| GO-ID | Function | Gene symbol (note these ar symbols and not sequences) |
|---|---|---|
| | | Functions of down-regulated immune response genes |
| 45321 | leukocyte activation | MICA, CD8A, CD8B, ELF4, TLR4, ADA, CD74, CD93, CD2, FCER1G, CD4, SYK, IL4, KLF6, PTPRC, CD3D, IL8, CD3E, RELB, SLAMF7, CD40, LAT, LCK, CD79A, LCP2 |
| 6954 | inflammatory response | CXCL1, ITGAL, TNF, TLR2, NFKB1, ITGB2, TLR4, CCL5, CD97, CCL20, KRT1, IL1B, IL1A, CEBPB, IL8, IL1RN, GRO3, CD40, CCL18, CD180, C8G, SCYA7, CCL13, CCR7, CYBB, CCR5, CRH, CD14 |
| 19882 | antigen processing and presentation | HLA-DQB1, MICA, CD8A, HLA-DRB1, RELB, HLA-C, FCGRT, HLA-B, HLA-G, CD74, B2M, FCER1G, HLA-DPA1, HLA-DPB1, HLA-DOB, AP3B1, HLA-DRA |
| 46649 | lymphocyte activation | IL4, PTPRC, KLF6, MICA, CD3D, CD8A, ELF4, CD3E, CD8B, RELB, CD40, SLAMF7, CD74, ADA, LCK, CD2, CD4, CD79A, SYK |
| 30097 | hemopoiesis | IL4, PTPRC, KLF6, CD3D, LYN, HCLS1, RELB, IFI16, MYH9, CD164, CD74, LCK, CD4, SPIB, CD79A, MYST1, SYK, MYST3 |
| 52033 | pathogen-associated molecular pattern recognition | PF4, CHIT1, TLR2, TLR4, SCYA7, CD14, PF4V1, CLP1, TICAM1, FPRL1, FPR1 |
| 6935 | chemotaxis | IL4, CXCL1, C5AR1, IL8, GRO3, ITGB2, PF4, CCL5, CCL18, SCYB5, SCYA7, CCL13, CCR7, CCR5, PPBP, CCL20, IL1B, FCER1G, SYK, |
| 42110 | T- cell activation | PTPRC, MICA, CD3D, CD8A, CD3E, CD8B, ELF4, RELB, CD74, ADA, LCK, CD2, CD4, SYK |
| 2274 | myeloid leukocyte activation | LAT, IL8, CD93, RELB, FCER1G, TLR4, LCP2 |
| 50778 | positive regulation of immune response | PTPRC, MICA, SLK, FYN, KRT1, TLR2, FCER1G, CD79A, C8G, SYK |
| 6959 | humoral immune response | PSMB10, CD83, ST6GAL1, TNF, HLXB9, POU2F2, KRT1, AIRE, C8G |
| 1934 | positive regulation of phosphorylation | TNF, CCND3, LYN, HCLS1, IL1B, CD4, SYK |
| 45087 | innate immune response | CYBB, IL1R1, SARM1, CLP1, KRT1, TLR2, TLR4, SLAMF7, CD180, C8G |

TABLE 1-continued

Functions significantly associated with differentially regulated immune response genes that passed Welch's t-test and FDR correction (q < 0.05 and showed >1.3 fold change in post RASP leukocyted compared with pre-RASP leukocytes.

| GO-ID | Function | Gene symbol (note these ar symbols and not sequences) |
|---|---|---|
| 2252 | immune effector process | PTPRC, LAT, MICA, FCN2, KRT1, FCER1G, SLAMF7, CD74, C8G |
| 30593 | neutrophil chemotaxis | IL8, FCER1G, IL1B, ITGB2, SYK |
| 7229 | integrin- signaling | LAT, ITGAL, ITGAX, ITGB2, MYH9, ITGAM, SYK |
| 45058 | T- cell selection | CD3D, CD4, CD74, SYK |
| 1816 | cytokine production | IL4, CD4, ISGF3G, CD226, LCP2 |
| 6909 | phagocytosis | CD93, FCN2, CLP1, FCER1G, CD14 |
| 2460 | somatic recombination for adaptive response | IL4, RELB, FCER1G, TLR4, CD74, C8G |
| | Functions associated with up-regulated immune response genes | |
| 48545 | response to steroid hormones | CEBPA, CAV1, HMGB2, PRKACA, CD24 |
| 42326 | negative regulation of phosphorylation | CAV1, PRKACA, INHA |
| 6956 | complement activation | C4B, C3, C2 |
| 10817 | regulation of hormone levels | DHRS2, ACE, FKBP1B |
| 43434 | response to peptide hormones | HHEX, PRKDC, PRKACA |
| 2762 | negative regulation of myeloid leukocyte differentiation | FSTL3, INHA |
| 32088 | negative regulation of NFkB activity | POP1, SIVA |
| 51384 | response to glucocorticoids | CEBPA, CAV1, PRKACA |
| 16481 | negative regulation of transcription | CEBPA, HHEX, CAV1, HMGB2, FST, HELLS |

Oligonucleotide Microarrays

Gene expression alterations in leukocytes of Rangers before and after Training were also analyzed using PAXgene RNA isolation and oligonucleotide microarrays representing 24 650 human gene probes. This different RNA isolation procedure and microarray assay again showed that the immune system was most significantly affected process. Normalized expression levels were analyzed using Welch's t-test (p<0.05, without multiple correction), and fold change filter (>=1.5 fold). Among 1570 genes (that passed these filters), 104 genes were associated with the immune response processes including microbial recognition, chemotaxis, inflammation, antigen presentation, and T-cell, B-cell and NK-cell activations (FIGS. 3A-E & Table 5).

Real Time Quantitative PCR Array

Figure 3A:
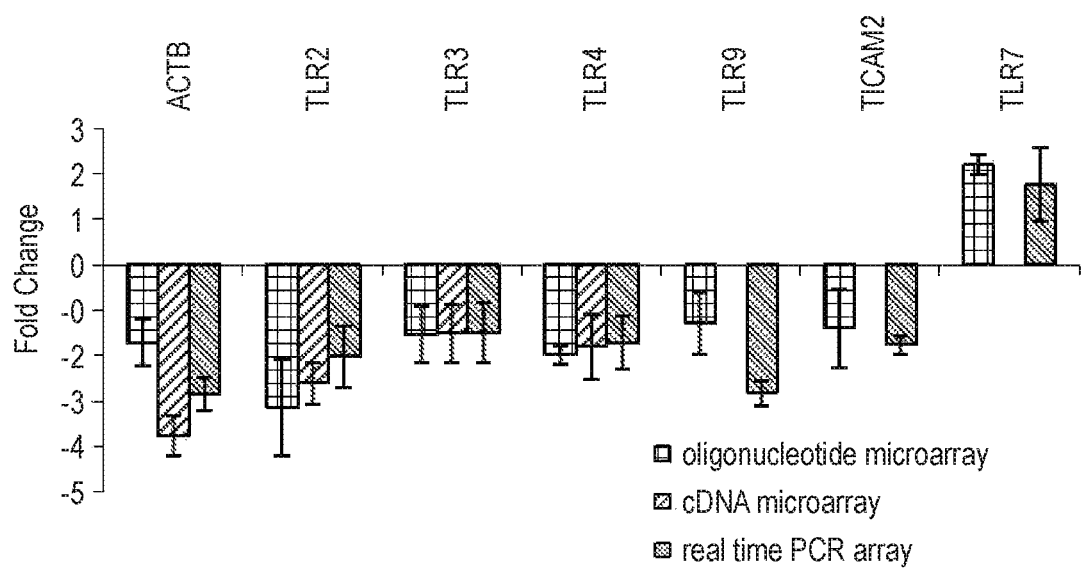
FIGS. 3A-E are graphs showing correlation of real time PCR arrays with those from cDNA and oligonucleotide microarrays.
Figure 3B:
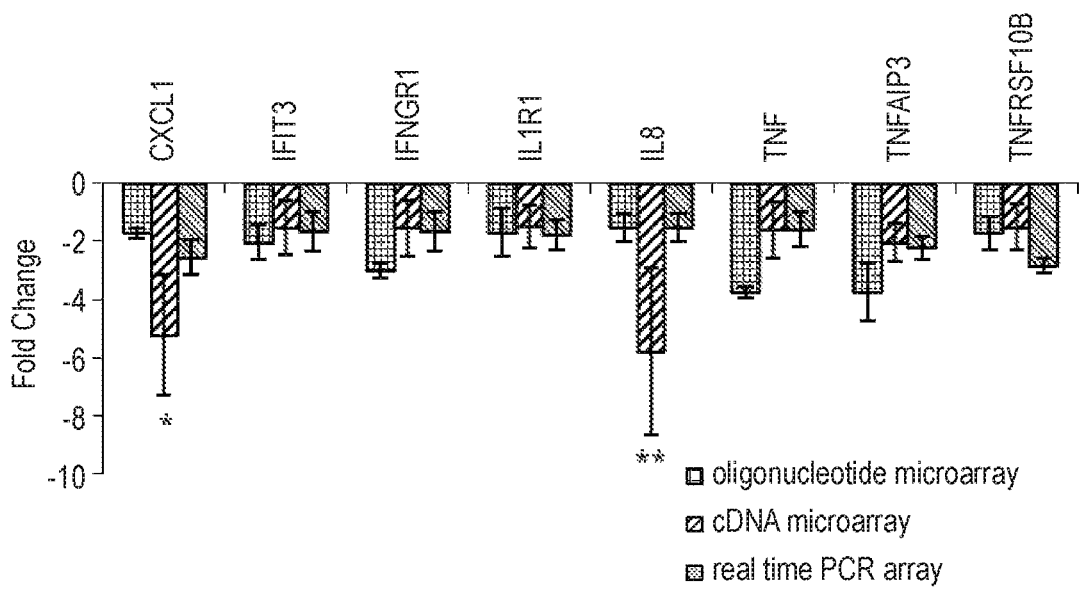
Figure 3C:
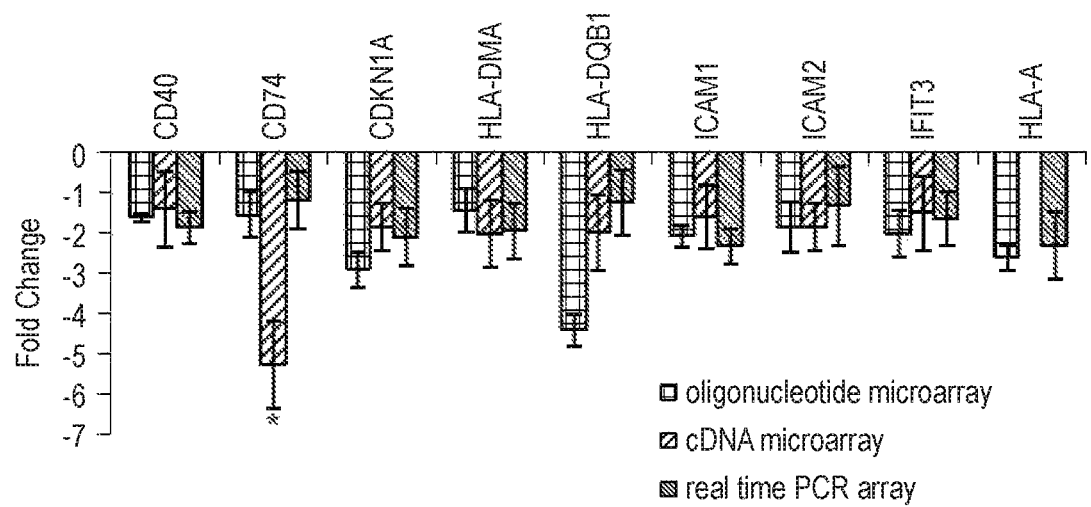

We used real time quantitative PCR (QPCR) arrays to confirm differential expression of genes identified by cDNA and oligonucleotide microarrays, and to survey additional immune related genes. Assay results of PCR arrays that contained more than 160 genes in antigen presentation and NFkB signaling pathways (RT² Profiler™ PCR Arrays, SABioscience, MD) verified down-regulation of 116 immune response genes, consistent with microarray data (Tables 3A, 3B and 4). The vast majority of the genes important for microbial pattern recognition, inflammation, antigen presentation, T-cell activation and transcription factors related to immune response were suppressed across cDNA, oligonucleotide and PCR arrays (FIGS. 3A and 3B)

Figure 3D:
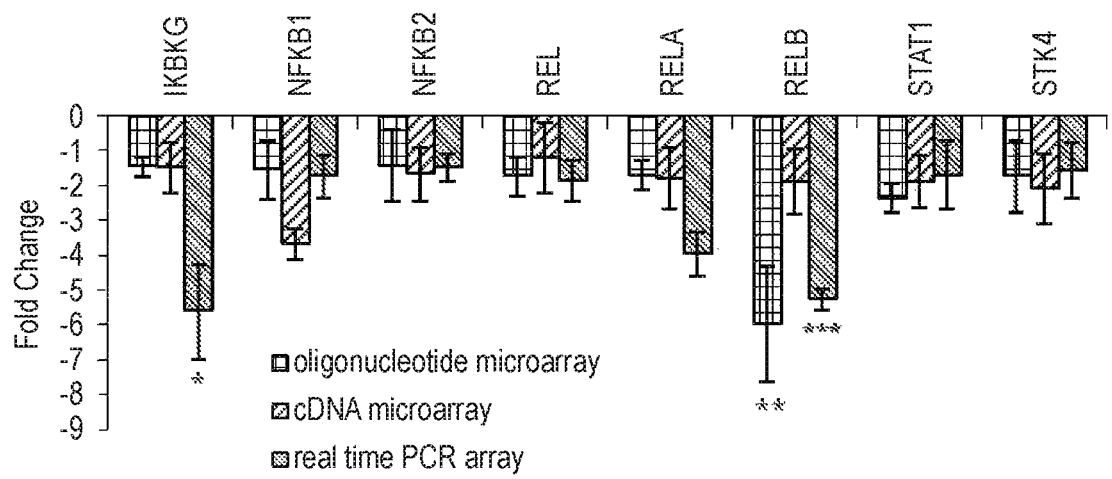
Figure 3E:
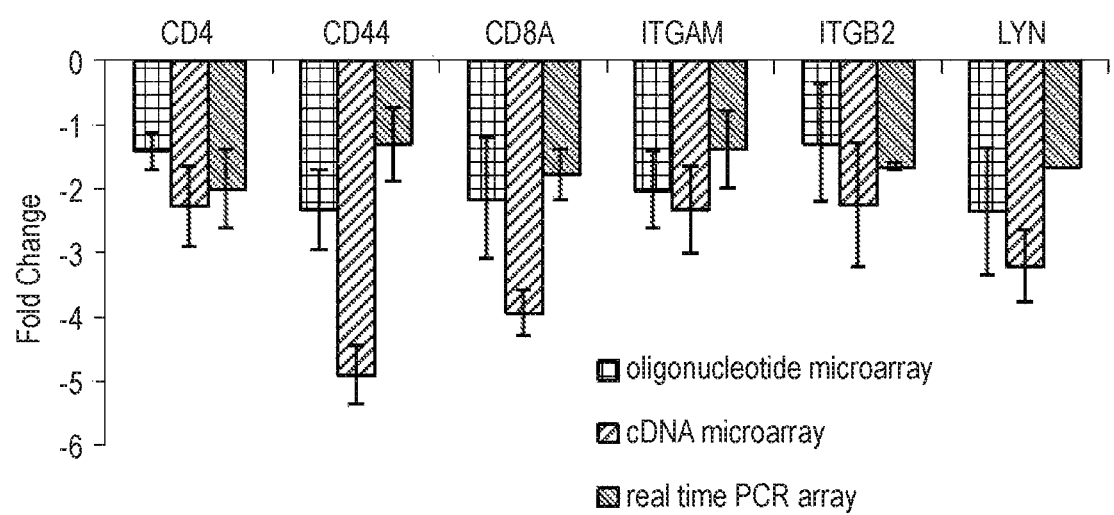

Referring to FIGS. 3A-E, genes are shown that are associated with pattern recognition receptors (FIG. 3A); inflammatory response (to scale the graph, fold changes of −15.2 and −23.8, labeled * and **, respectively, were assigned a values of ~5 and 6, respectively (FIG. 3B); antigen preparation and presentation (*fold change: −12.3; assigned value ~−5 for scaling the graph) (Fig. C); transcription factors (*fold change: −12.6; fold change: −12.3; *fold change −14; these were adjusted to around −5 for scaling the graph) (FIG. 3D); T-cell activation, differentiation and proliferations. Expression profiles of genes shown in pannels A-E were assayed using SABiosciences RT²Profiler™ (PAHS 406 and PHAS 25) PCR Arrays, cDNA microarrays, and oligonucleotide microarrays (FIG. 3E). Total RNA samples were isolated using Trizol reagents for cDNA microarray analysis, and total RNA samples used for PCR and oligonucleotide arrays were isolated from blood samples collected in PAXgene tubes. (Note: PCR arrays were carried out on subjects participated throughout our study, and fold changes for these figures were calculated on data from both round subjects).

Real Time Quantitative PCR

Additional quantitative real-time PCR assays were carried out using specific primer pairs to confirm 10 representative genes among 1396 significantly altered genes shows number of genes that passed Welch's t-test at different q-values (FDR corrected p-values) and Fold Change cut-offs) (FIG. 2A)(Table 2). Real-time QPCR Assayed and confirmed genes included IL1B, IL2RB, CD 14, HLA-G, RAP1A, AQP9, ALB, CSPG4, CDC2, A2M, and GAGE2. Individual real-time QPCR results confirmed and validated these differentially expressed genes identified by cDNA arrays (FIG. 4A).

Figure 4A:
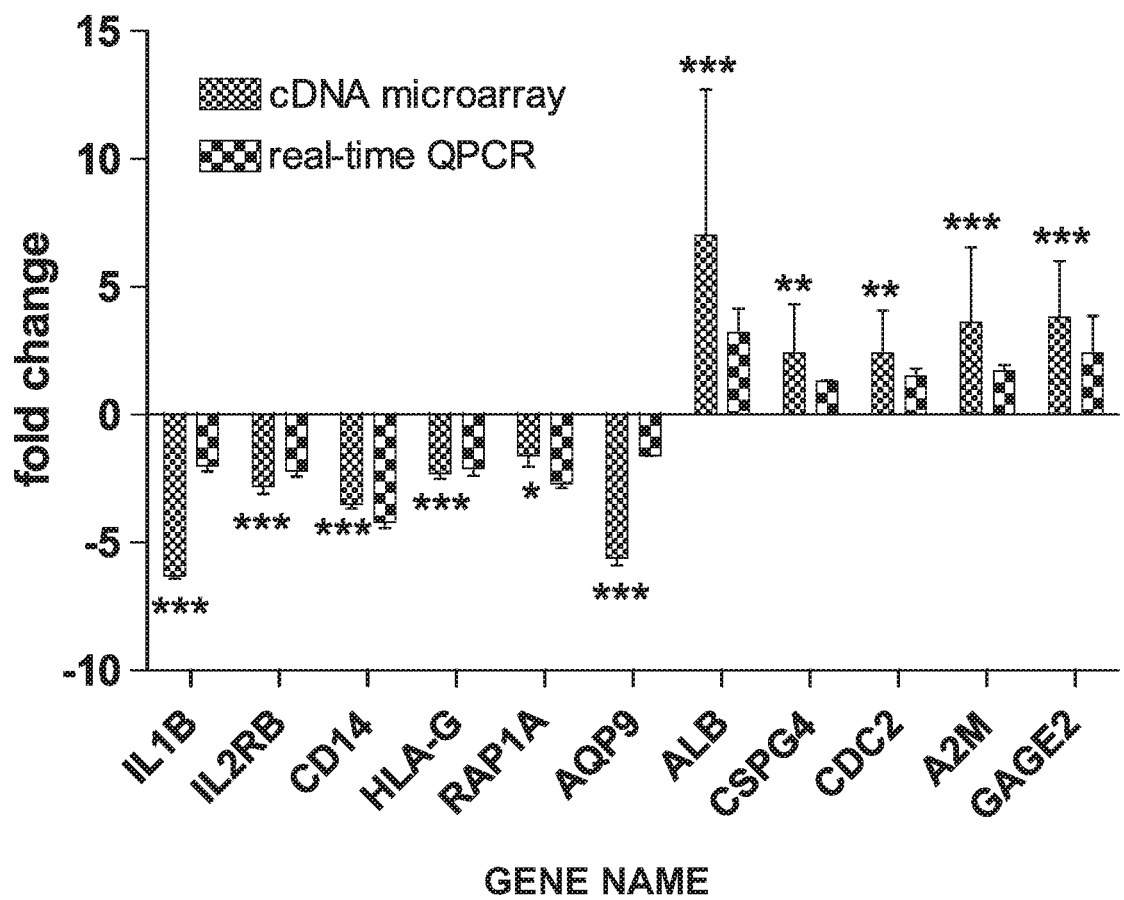
FIG. 4A is a graph showing correlation of Real time QPCR and cDNA microarray analyses.

FIG. 4A shows Real time PCR reactions for each gene were carried out with three or more replicates. The microarray data were from Trizol RNA isolation and cDNA microarrays (*p-values<$10^{-5}$, p-values<0.0002, *p-value<0.02). The p-values given here were taken from the microarray analyses obtained after FDR correction.

Genes Associated with Microbial Recognition

Figure 5A:
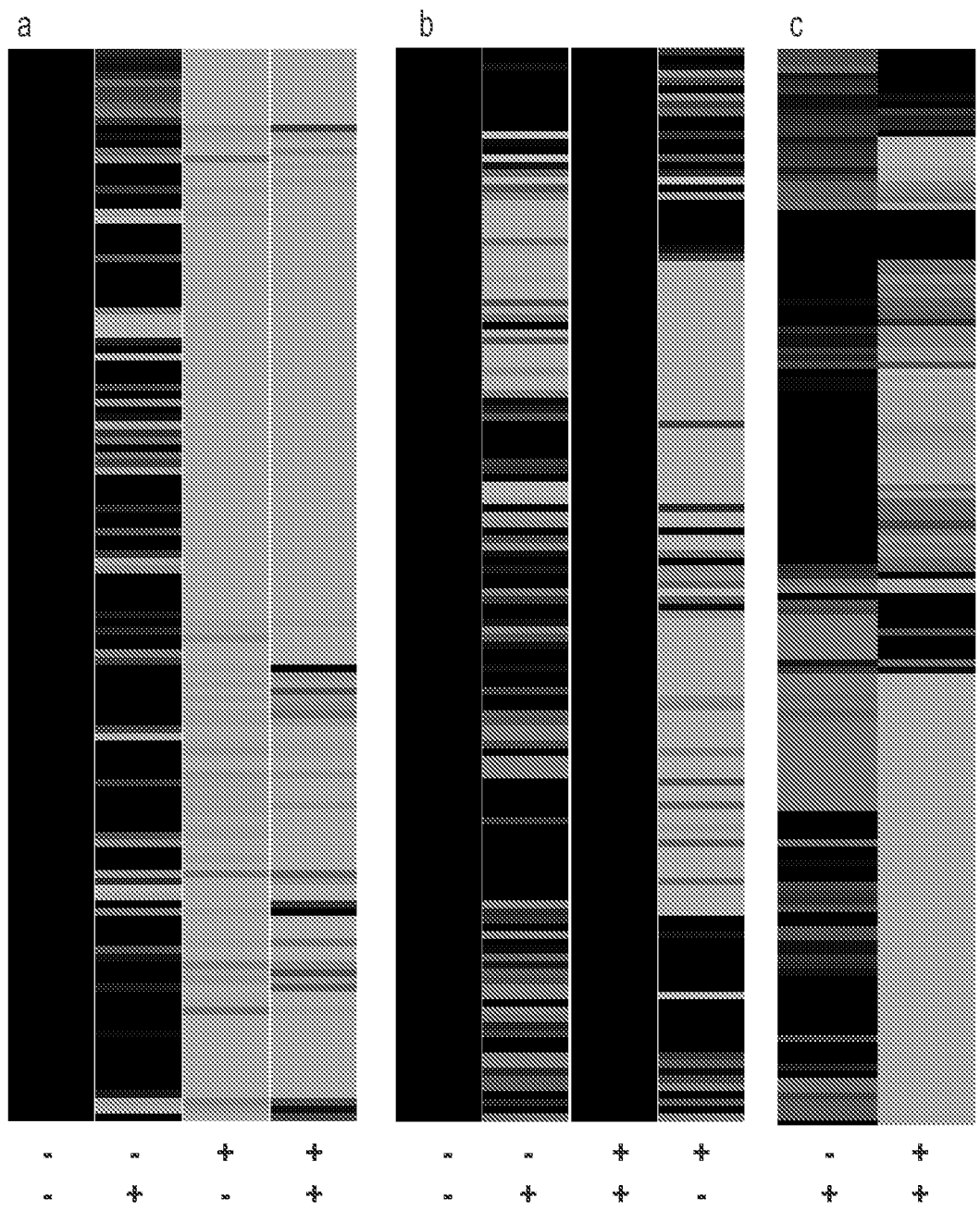
FIG. 5A is a heat map of expression patterns of immune response genes in leukocytes in-vitro exposed to SEB.
Figure 5B:
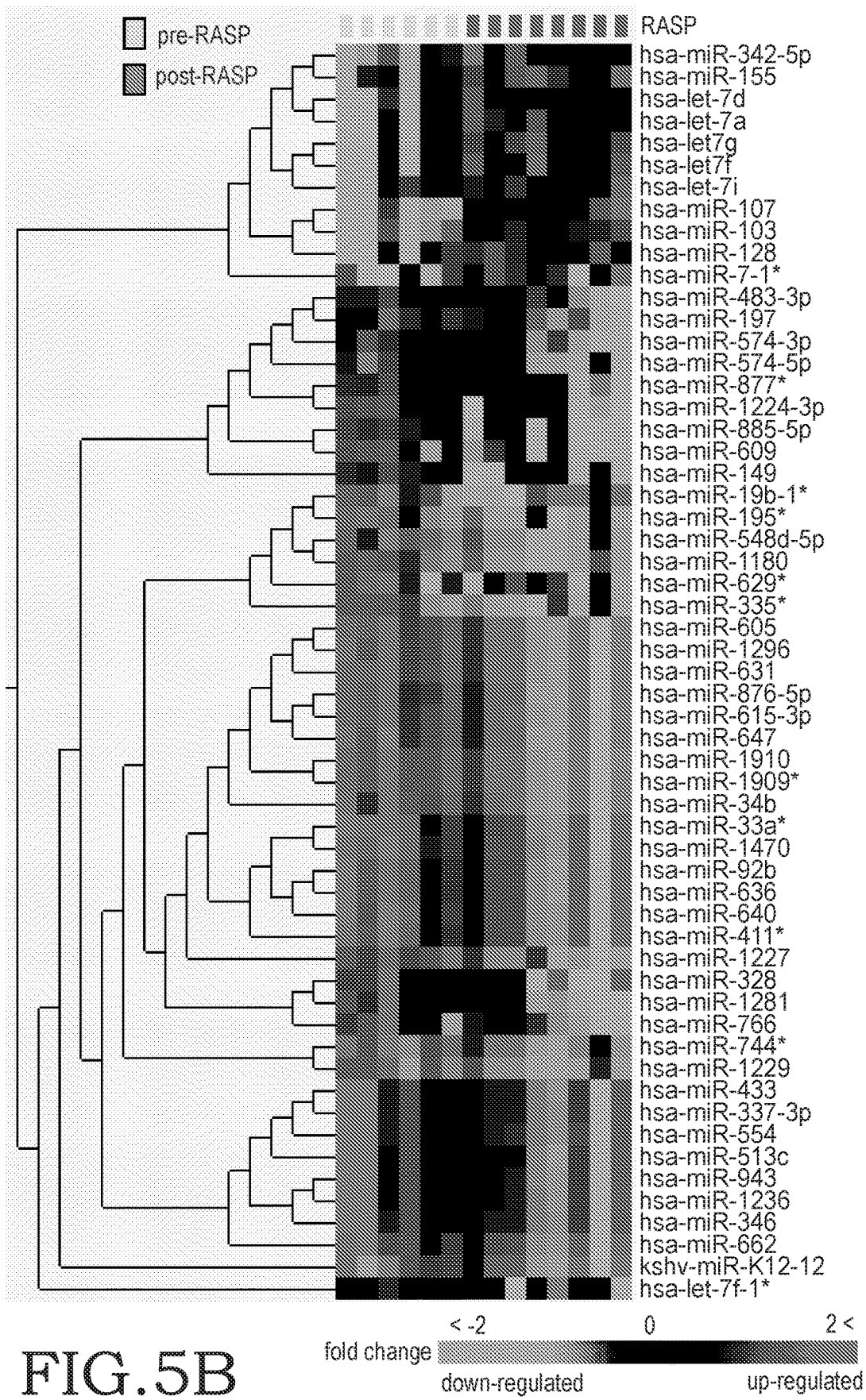
FIG. 5B is a heat map of predicted and experimentally observed targets of RASP-regulated microRNAs.
Figure 5C:
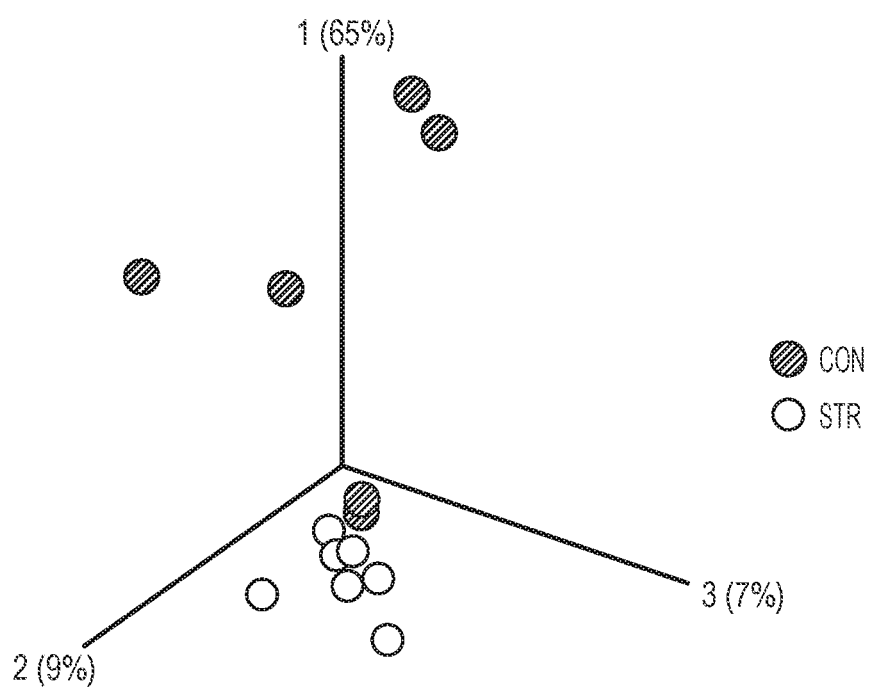
FIG. 5C is a sample PCA of differentially regulated microRNAs that passed Welch's Test (p<0.25) and 1.3 fold change cut off.
Figure 5D:
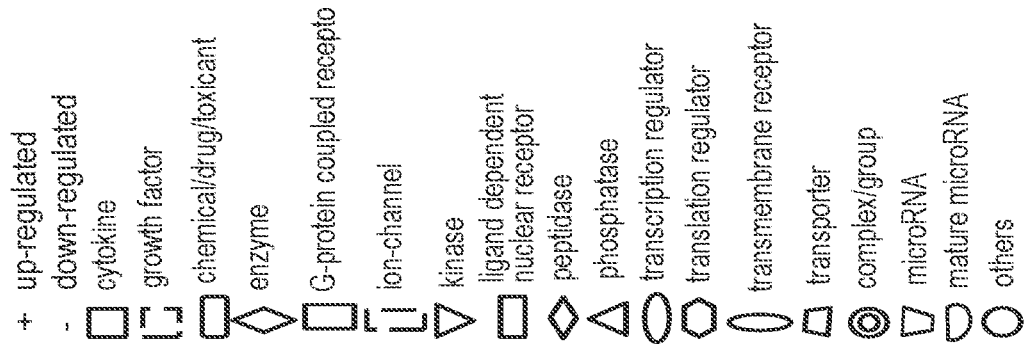
FIG. 5D is a map of regulatory interaction among stress-induced miRs, important transcription factors (NFkB1, NR3Ca, SATB1), inflammatory cytokines and antigen presenting molecules.
Figure 5D:
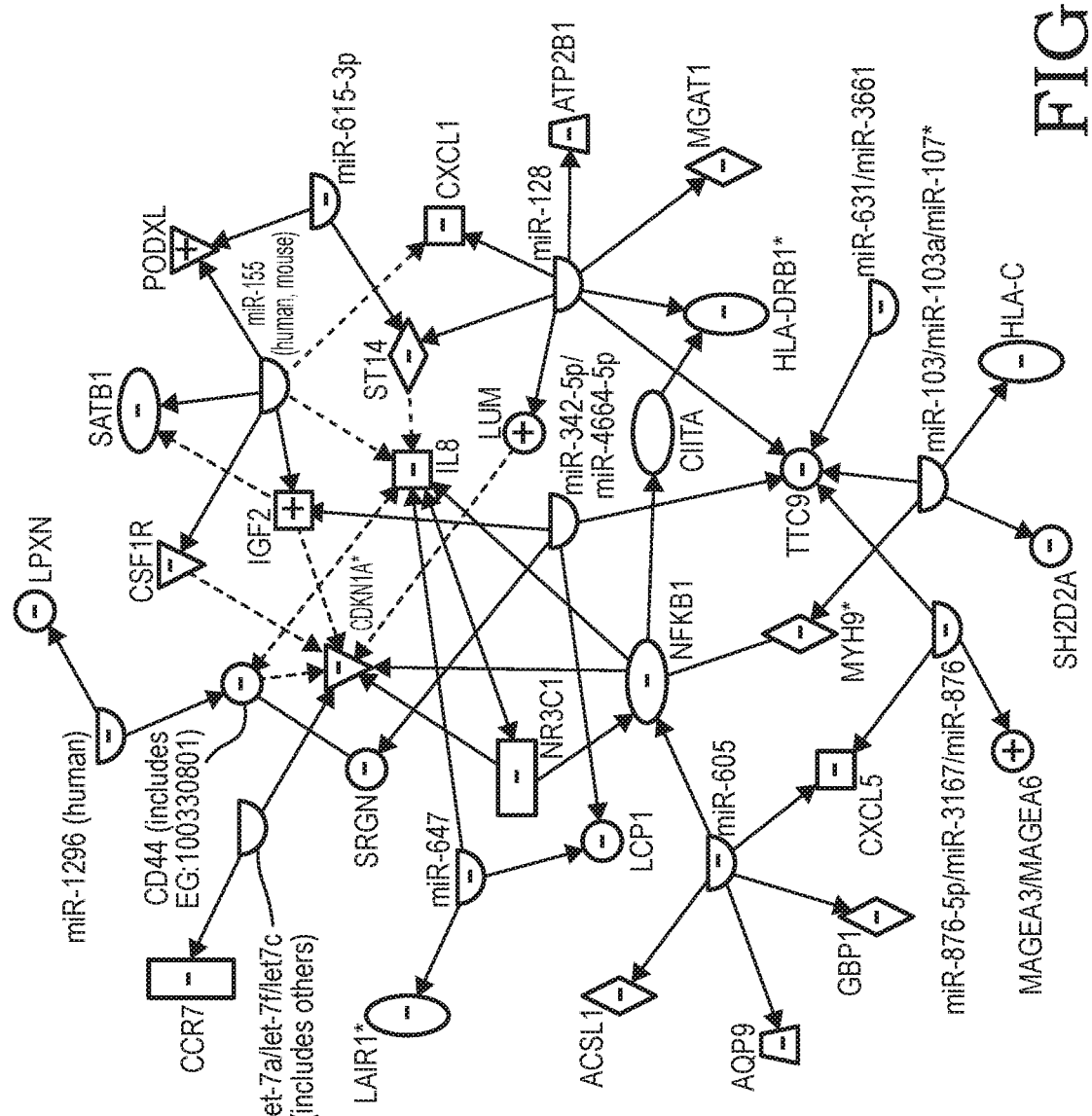

Genes associated with microbial pattern recognition were significantly suppressed in post-Training leukocytes (Table 5, & Tables 1 & FIG. 5D). These genes include Toll-like receptors (TLR 2, 3, and 4), CD14, CD93, chitinase 1 (CHIT1), formyl peptide receptor 1 (FPR1), formyl peptide receptor like 1 (FPRL1), dicer1 (DICER1), cleavage and polyadenylation factor I subunit (CLP1), platelet factor 4 (PF4), platelet factor 4 variant 1 (PF4V1), toll-like receptor adaptor molecule 1 (TICAM1), and myeloid differentiation primary response gene 88 (MYD88). TLR6 was down-regulated but it did not pass the FDR correction filter.

CD 14, along with TLR4/TLR4 and TLR2/TLR6, recognize lipopolysaccharides and peptideoglycans, respectively. TLR3, CLP1 and DICER1 bind to double stranded viral RNAs. TLR9 and CD93 recognize unmethylated CpG dinucleotides of bacterial DNA, and patterns of apoptotic cells, respectively. FPR1 and FPRL1 bind bacterial N-terminal formyl-methionine peptides. CHIT1 recognizes fungal and pathogens with chitin patterns. PF4 and PF4V1 recognize patterns of *plasmodium* and tumor cells. TICAM1 and MYD88 are important cytosolic adaptor molecules of microbial pattern recognitions. Transcripts of these genes were down-regulated suggesting a compromised innate immune response with regard to microbial recognition.

Genes Associated with Chemotaxis and Inflammation

Stress suppressed transcripts associated with chemotaxis and inflammation included interleukins (IL 1A, IL1B, IL4, IL8), interleukin receptors (IL1R1, IL1RN, IL2RB, IL10RA), chemokine (C-X-C motif) ligands (CXCL 1), chemokine (C-C motif) ligands (CCL13, CCL18, CCL20), tumor necrosis factor alpha (TNFα), TNF receptor superfamily members 1B, 10B and 10C (TNFRSF1B, TNFRSF10B and TNFRSF10C), TNF superfamily members 3, 8, (LTB, TNFSF8), complement component 8 gamma (C8G), cytochrome b-245 beta (CYBB), CD97 and interferon gamma receptor (IFNGR2) (Tables 1 & 5).

Genes Associated with Activation of Myeloid Leukocytes

Tables 1 & 5 show suppressed transcripts associated with activation of mast cells and macrophages. These included toll-like receptors (TLR4), TNF, LAT, lymphocyte cytosolic protein 2 (LCP2), SYK, CD93, and IL4 RELB. Suppressed genes associated with inflammatory responses (ILL CD14, INFGR1) were also significantly associated with activation of myeloid cells. Differentiations of myeloid leukocytes were significantly associated with interferon gamma inducible proteins 16 and 30 (IFI16), myosin heavy chain 9 (MYH9), IL4, Spi-B transcription factor (SPIB), NFkB3, MYST histone acetyltransferases (MYST1 and 3), TNF, PF4, hematopoitic cell-specific lyn substrate 1 (HCLS1), V-yes-1 Yamaguchi sarcoma viral related oncogene homolog (LYN) and V-maf (musculoaponeurotic fibrosarcoma) oncogene homolog b (MAFB). Down-regulation of hemopoietic transcription factors (MAFB and HCLS1) and CSF1R may indicate less viability of myeloid cells to expand or to replenish. Suppression of mRNAs of these genes suggests poor activation, differentiation and proliferation of myeloid leukocytes in response to infection, and hence poor innate and adaptive immune responses.

Genes Associated with Antigen Presentation

Genes associated with antigen preparation encompass MHC classes (I & II), CD1s, B-cell co-receptors and integrins (Tables 1 and 5). Transcripts of MHC class I (HLA-B, HLA-C, HLA-G, beta-2-microglobulin (B2M)), MHC class II (HLA-DRB1, HLA-DRA, HLA-DPA1, HLA-DPB1, HLA-DQA1, HLA-DQB1, CD74, HLA-DOB), B-cell co-receptors (CD79A, CD79B), Ig heavy constant gamma 1 (IGHG1), Ig heavy constant alpha 1 (IGHA1), MHC class I polypeptide related sequence A (MICA), adaptor-related protein complex 3 beta1 (AP3B1), intercellular adhesion molecules 1, 2 and 3 (ICAM1, ICAM2, ICAM3) were down-regulated implying poor antigen preparation and presentation, and hence impaired adaptive immune response.

Genes Associated with Activation of Lymphocytes

Suppressed transcripts associated with T-cell activation, differentiation and proliferation included TCR co-receptors (CD4, CD8α, CD8β, CD3ε, CD3δ, CD247), linker for activation of T cells (LAT), TCR signaling molecules [protein kinase c theta (PRKCQ), protein tyrosine phosphatase receptor type C (PTPRC), C-SRC tyrosine kinase (CSK), spleen tyrosine kinase (SYK) lymphocyte specific protein tyrosine kinase (LCK)], integrins CD2, CD44, integrin alpha L, M and X (ITGAL, ITGAM, ITGAX), and cyclin D3 (CCND3) (Tables 1 & 5).

Interleukin 4, SYK, PRKCD, CD40, PTPRC, cyclin-dependent kinase inhibitor 1A (CDKN1A), Kruppel-like factor 6 (KLF6), SLAM family member 7 (SLAMF7), and killer cell Ig-like receptor three domains long cytoplasmic tail1 (KIR3DL1) were significantly associated with activation, differentiation and proliferation of B-cells, and NK-cells (Tables 1 & 5).

Transcription Factors Associated with Immune Responses

Transcription factors that are important regulators of immune response genes were down-regulated. Suppressed factors included nuclear factor kappa B family (NFkB1, NFkB2, RELA, RELB), interferon regulatory factors 1, 5, 7, 8 (IRF1, IRF5, IRF7 and IRF8), signal transducer and activator of transcription (STAT2, STAT6), and SP transcription factors (SP1, SP140) (Tables 1 & 5). In addition, transcription factors GA binding protein alpha (GABPA), POU class 2 homeobox 2 (POU2F2), p53 (TP53), p53 binding protein 1 (TP53BP1), early growth response 2 (EGR2), splicing factor 1 (SF1), and hypoxia inducible factor 3 and alpha subunit (HIF3A) were down-regulated. Up-regulated transcription factors included hepatocyte nuclear factor 4 alpha (HNF4A) hepatic leukemia factor (HLF), sterol regulatory element binding transcription factor 2 (SREBF2) transcription factor AP-2 alpha (TFAP2A), transcription factor 7-like 2 (TCF7L2) and NF-kappa-B inhibitor-like 2 (NFKBIL2) (Tables 1 & 5).

ELISA Assays of Plasma Proteins

Figure 4B:
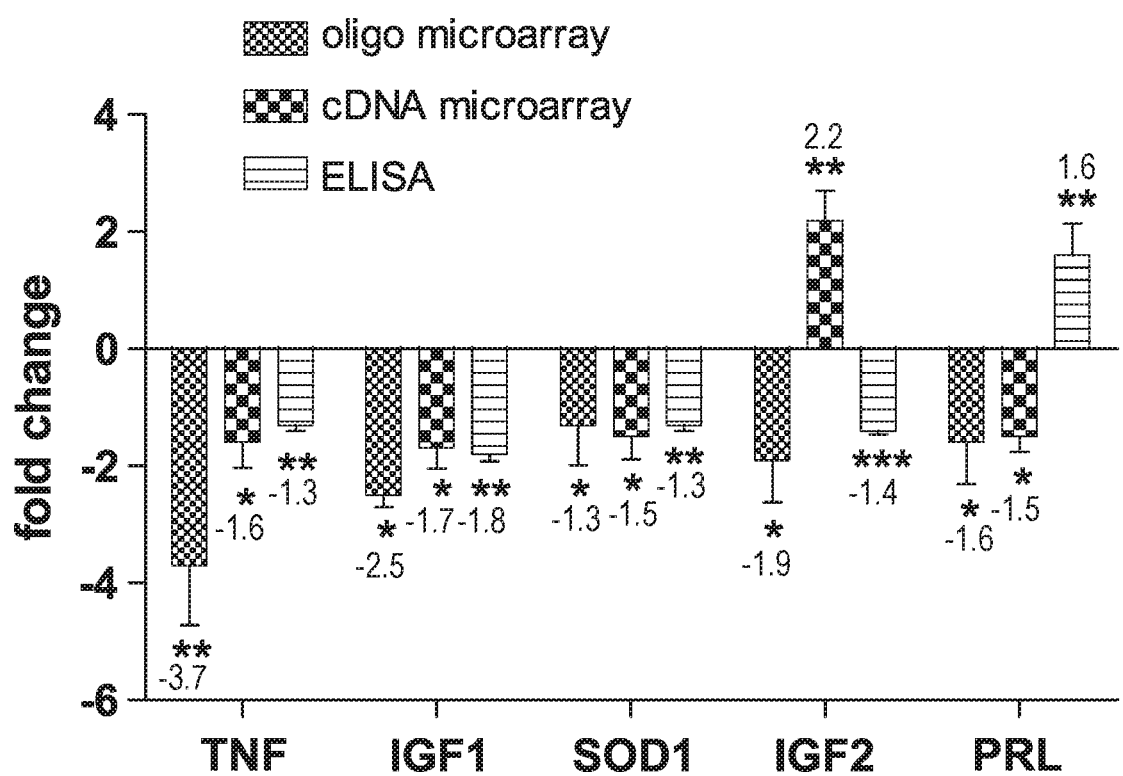
FIG. 4B) is a graph showing ELISA determination of plasma concentrations of proteins, and comparison with level of their transcripts from microarrays data.

Plasma concentrations of insulin-like growth hormones 1 and 2 (IGF1 and IGF2), prolactin (PRL), tumor necrosis factor alpha (TNF), and enzymatic-activity of superoxide dismutase 1 (SOD 1) were determined by ELISA to examine gene expression alterations at the protein level. Relative quantities of proteins, and levels of transcripts profiled by cDNA and oligonucleotide microarrays were compared (FIG. 4B). Reduced IGF1 has been shown to be a biomarker of negative energy balance under conditions of multiple Ranger Training stressors[12], and IGF1 transcript in leukocytes and protein in plasma are reduced after Training. Plasma concentration of PRL was up-regulated while transcriptome profiling showed down-regulation by microarray analyses, suggesting differential regulation of prolactin at transcription and translation levels.

FIG. 4B shows plasma concentrations of prolactin (PRL), insulin-like growth factors I and II, tumor necrosis factor alpha (TNF α) and enzymatic activity of superoxide dismutase 1 (SOD 1) were assayed using nine biological replicates and three experimental replicate samples corresponding to each biological replicate for each of these proteins. The IGF-I depletion is consistent with other studies that measured its plasma concentration on similar subjects[13] (*p-values<0.003, p-values<0.04, *p-value <0.0002).

Response of Leukocytes to Ex Vivo Treatment of Staphylococcal Enterotoxin B

*Staphylococcus* enterotoxin B (SEB) is a superantigen, and a potent T cell activator known to induce proinflammatory cytokine release in vitro[14]. Leukocytes of Ranger Trainees collected before and after Training were challenged ex vivo with SEB and immune response transcripts were analysed. In pre-Training leukocytes, SEB toxin induced majority of immune response genes (FIG. 5A). However, in post-Training leukocytes, stressed suppressed immune response genes showed no sign of re-activation even after ex vivo exposure to SEB (FIG. 5A). Rather SEB seemed to further suppress expression of many of these transcripts. Impaired response of post-Training leukocytes to SEB is consistent with suppression of immune response pathways and networks revealed by transcriptome analyses.

In FIG. 5A, expression of immune response genes in leukocytes exposed ex vivo to SEB is shown. Leukocytes isolated from whole blood were treated with SEB (~$10^6$ cells ml$^{-1}$ in RPMI 1640 and 10% human AB serum at a final concentration of 100 ng ml$^{-1}$ SEB). Total RNA was isolated using Trizol and expression levels were profiled using cDNA microarrays. Shown here are the 151 RASP-suppressed immune response genes that passed Welch's test and FDR correction (q<0.05). (a) Lanes left to right: pre-RASP samples not exposed to SEB (control), pre-RASP samples exposed to SEB, post-RASP samples not treated with SEB, post-RASP samples exposed to SEB. For comparative visualization purpose, expression values of the other groups were transformed against the Pre-RASP control samples (black lane). Heat map of the same data without transformation is given in the supplement. (b) Expression values in SEB exposed leukocytes (in both the pre- and post-RASP conditions) were compared with the corresponding SEB untreated groups (pre-RASP control and post-RASP stressed groups). (c) Heat map of 151 immune response genes in SEB treated groups (in both pre- and post-RASP leukocytes) clustered after subtraction of the corresponding baseline responses (cluster after subtraction of their expressions in the corresponding untreated groups shown in lane (b). Lane c clearly shows pour response of post-RASP leukocytes towards SEB exposure compared with pre-RASP leukocytes.

MicroRNA Arrays

Figure 5E:
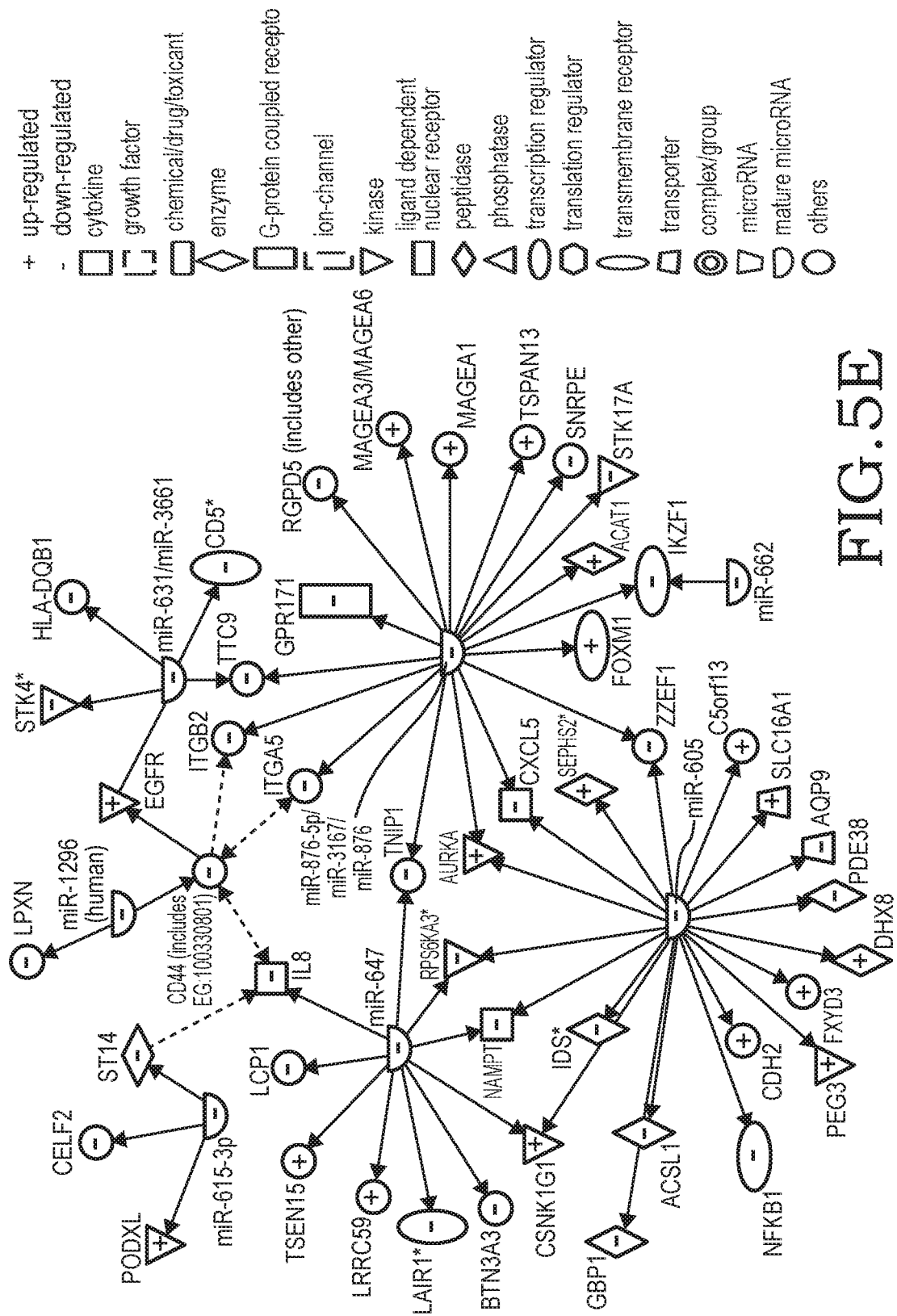
FIG. 5E is a map showing seven stress-suppressed miRs targeting 48 mRNAs among differentially regulated mRNAs that passed q<0.001 and 1.5 fold change.
Figure 6:
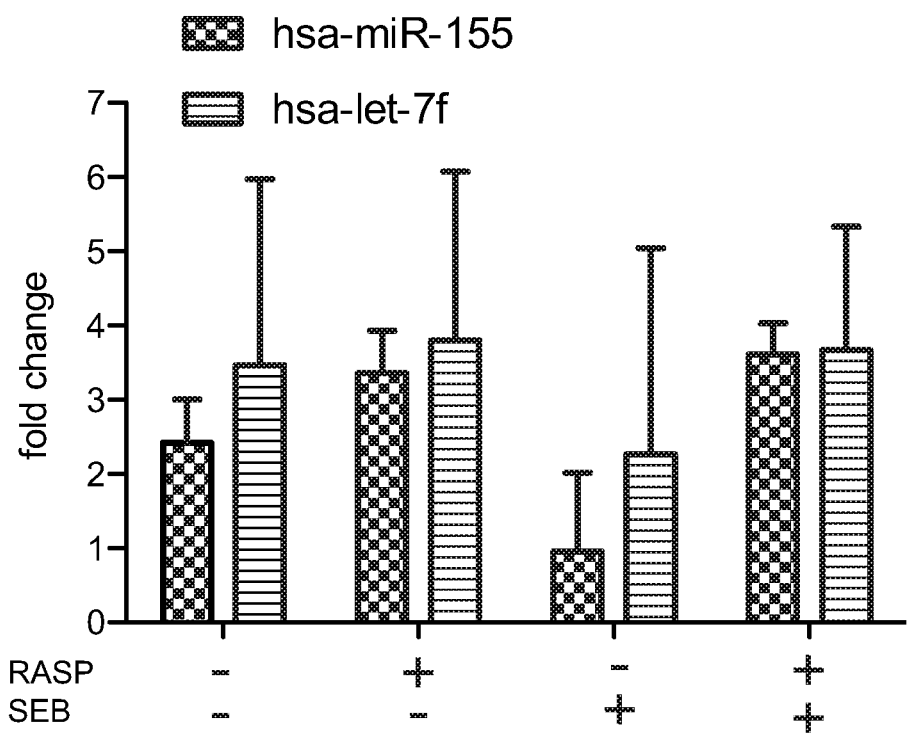
FIG. 6 is a graph showing predicted targets of miR-155 and let-7f families.

Differentially regulated microRNAs (miRs) in pre- and post-Training samples were assayed using Agilent's human microRNA chip containing ~15 000 probes representing 961 unique miRs. Comparison of 535 miRs (that passed normalization and flag filters) using Welch's t-test at p<0.1 with a 1.3 fold change cutoff gave 57 miRs (FIG. 5C). MicroRNA target scan was used to identify high-prediction and experimentally proven targets of these differentially regulated miRs. Among up-regulated miRs, hsa-miR-155 (p<0.08) and hsa-let-7f (p<0.1), were shown to target many suppressed transcripts, including transcription regulators of genes important for dendritic cell maturation and glucocorticoid receptor signaling. Expression of miR-155 was suppressed in pre-Training samples exposed to SEB, but it was induced in post-Training samples treated with SEB (FIG. 6). Other stress-induced miRs were predicted to have regulatory connection with stress-affected inflammatory cytokines, antigen-presenting molecules, and transcription regulators of genes involved in immune response (FIG. 5D). Stress-suppressed miRs—miR-662, miR-647, miR-876-5P, miR-631, miR-1296, miR-615-3P, and miR-605—have a number of regulation targets among stress-regulated genes involved in NFkB activation pathways (FIG. 5E). In FIG. 5E enriched pathways: IL-7 and IL-8 signalings, and NFkB activation pathways are shown. No targets were identified for two highly suppressed miRs, miR-1910 and 1909*.

FIG. 6 shows predicted targets of miR-155 and hsa-let 7f families. In FIG. 6, expression levels of hsa-miR-155 and hsa-let-7f in pre-RASP (control), post-RASP (stressed) and pre-RASP exposed to SEB, and post-RASP exposed to SEB groups. Sequences of mature miR-155 and let-7f are also shown.

See also FIG. 5B for predicted and experimentally observed targets of RASP-regulated micro RNAs. 57 microRNAs passed Welch's T-test (P<0.1) and 1.3 fold change. Most (46 of 57) miRs were downregulated, and 11 miRs were upregulated in post-RASP leukocytes.

Expression Data Based Prediction of Transcription Factors and Target Genes

Figure 7A:
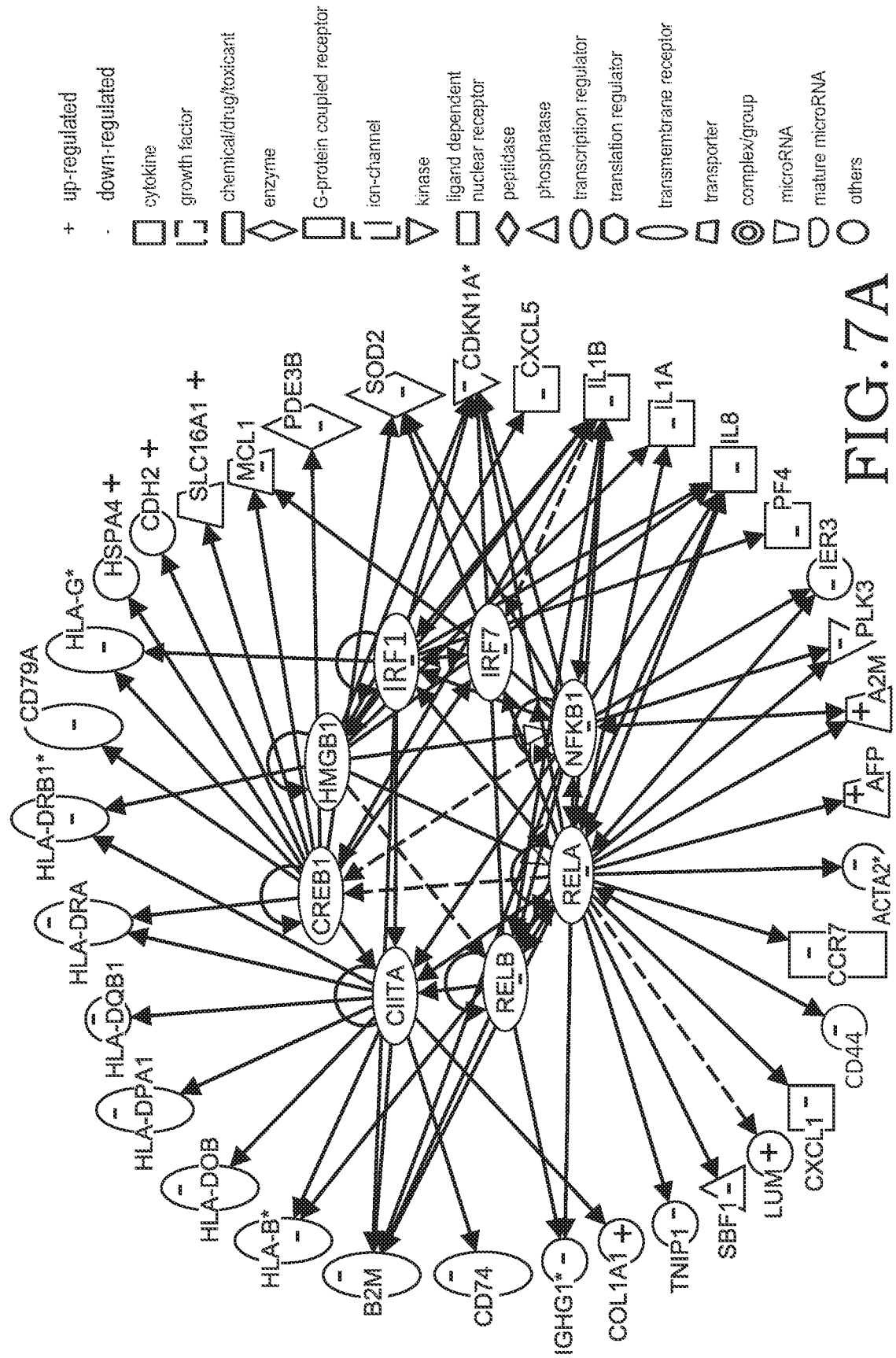
FIG. 7A is a map of transcription factors predicted to be inhibited by battlefield stressors and their targets among stress-affected genes.
Figure 7B:
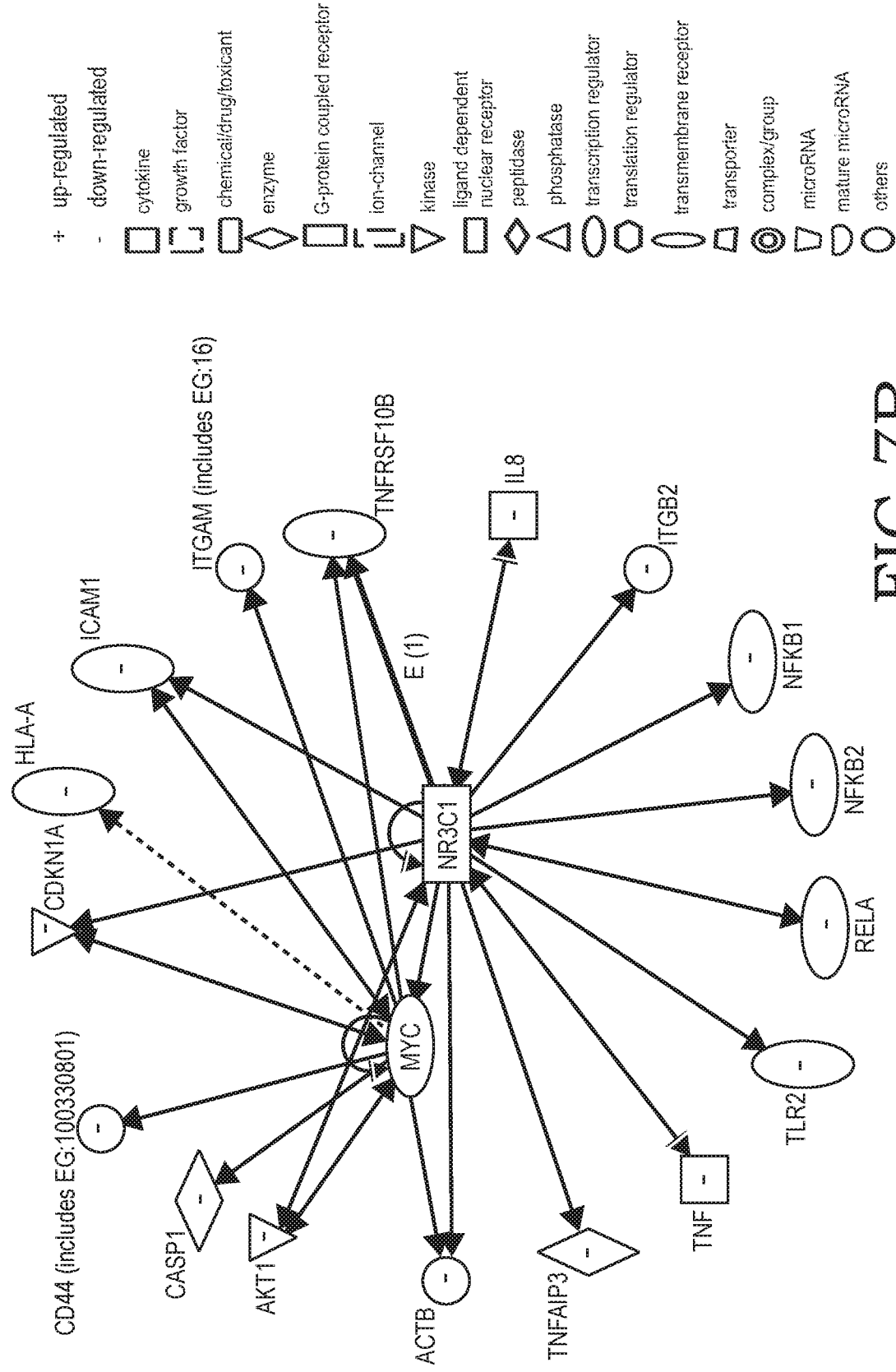
FIG. 7B is a map showing transcription factors targeting RT-PCR assayed and differentially regulated genes.

Computational & data analyses tools, and databases (see Materials and Methods) were used for empirical and predictive association of transcription factors (TFs) and their regulatory targets among stress-altered genes. Activated or inhibited TFs, common regulatory sites of target genes, and prediction z-scores of identified TFs were computed based on 1369 differentially regulated genes obtained from cDNA array data (Table 2). TFs at the top of stress-inhibited list (IRF7, RELA, NFkB1, RELB, CREB1, IRF1, HMGB1 & CIITA) and their differentially expressed targets (Table 2) were found to be involved in inflammation, priming of adaptive immune response, and glucocorticoid receptor signaling (FIG. 7A and FIG. 7B). FIG. 7B shows transcription factors targeting RT-PCR assayed and differentially regulated genes. Both MYC and NR3C1 were predicted to be activated (according to prediction z-score value, which were >2.5). The top function associated with these targets were apoptosis of leukocytes, hematopoisis, proliferation of blood cells, immune response; and top pathways are given in the table immediately below in Table A:

TABLE A

Network showing MYC and NR3C1 targets among immune response genes

| Symbol | EntrezID | FC | Family | Drugs | Entrez Gene Name |
|---|---|---|---|---|---|
| ACTB | 60 | −1.73 | other | | actin, beta |
| AKT1 | 207 | −3.13 | kinase | enzastaurin | v-akt murine thymoma viral oncogene homolog 1 |
| CASP1 | 834 | −1.58 | peptidase | | caspase 1, apoptosis-related cysteine peptidase |
| CD44 | 960 | −2.33 | other | | CD44 molecule (Indian blood group) |
| CDKN1A | 1026 | −2.92 | kinase | | cyclin-dependent kinase inhibitor 1A (p21, Cip1) |
| HLA-A | 3105 | −2.63 | other | | major histocompatibility complex, class I, A |
| ICAM1 | 3383 | −2.09 | transmembrane receptor | | intercellular adhesion molecule 1 |
| IL8 | 3576 | −1.53 | cytokine | | interleukin 8 |
| ITGAM | 3684 | −2.02 | other | | integrin, alpha M (complement component 3 receptor 3 subunit) |

TABLE A-continued

Network showing MYC and NR3C1 targets among immune response genes

| Symbol | EntrezID | FC | Family | Drugs | Entrez Gene Name |
|---|---|---|---|---|---|
| ITGB2 | 3689 | −1.29 | other | | integrin, beta 2 (complement component 3 receptor 3 and 4 subunit) |
| MYC | 4609 | | transcription regulator | | v-myc myelocytomatosis viral oncogene homolog (avian) |
| NFKB1 | 4790 | −1.56 | transcription regulator | | nuclear factor of kappa light polypeptide gene enhancer in B-cells 1 |
| NFKB2 | 4791 | −1.44 | transcription regulator | | nuclear factor of kappa light polypeptide gene enhancer in B-cells 2 (p49/p100) |
| NR3C1 | 2908 | | ligand-dependent nuclear receptor | rimexolone, | nuclear receptor subfamily 3, group C, member 1 (glucocorticoid receptor) |
| RELA | 5970 | −1.72 | transcription regulator | NF-kappaB decoy | v-rel reticuloendotheliosis viral oncogene homolog A (avian) |
| TLR2 | 7097 | −3.14 | transmembrane receptor | | toll-like receptor 2 |
| TNF | 7124 | −3.74 | cytokine | adalimumab | tumor necrosis factor |
| TNFAIP3 | 7128 | −3.74 | enzyme | | tumor necrosis factor, alpha-induced protein 3 |
| TNFRSF10B | 8795 | −1.71 | transmembrane receptor | tigatuzumab | tumor necrosis factor receptor superfamily, member 10b |

Regulatory sites for a number of transcription factors including SP1, CREB1, ATF6, cEBP, and binding sites for the defense critical—NFkB transcription factors complex, and stress response sites (STRE) were among common regulatory motifs identified for some of stress-suppressed genes, STRE site being predicted to be regulated by MAZ and MZF1. Stress activated factors included GFI1, MYC, FOXM1, GLI2, MAX and HNF1A (Table 2), and these factors induced genes important for hormone biosynthesis and suppressed immune related genes.

FIG. 7A shows transcription factors predicted to be inhibited by battlefield stressors and their targets among stress modulated genes. Shown here are transcription factors predicted to be inhibited by battlefield stessors (Table 2) and their targets among 288 stress-affected transcripts (filtered using Welch's t-test and FDR, q<0.001, and >1.5 fold change). Enriched function and pathways of these transcripts include activation and proliferation of leukocytes, maturation of dendritic cells (DCs), communication between innate and adaptive immunity, glucocorticoid receptor signaling and antigen presentation pathway.

TABLE 2

Predicted transcription factors and targets identified among 1396 genes that passed Welch's t-test, FDR correction (q ≤ 0.05) and 1.5 fold change cutoff.

| TF | z-score | p-value | target molecules in dataset |
|---|---|---|---|
| | | | activated transcription factors and targets |
| GFI1 | 3.1 | 4.1E−04 | CASP1, CDKN1A, CEBPA, GUSB, ICAM1, IL1A, IL1B, IL8, IRF1, MMP7, NFKB1, NFKB2, RELA, RELB, TRAF3 |
| MYC | 3 | 1.6E−17 | ACAT1, ACTB, ACTN1, AFP, AHCY, ALB, BCAT1, BCL6, BIN1, BIRC2, BIRC5, CAPN2, CASP1, CASP10, CAV1, CCND1, CCND3, CD44, CD48, CDC20, CDH2, CDK1, CDK11A/CDK11B, CDKN1A, CEBPA, COL14A1, COL1A1, CSPG4, CYFIP2, DDX11/DDX12, DDX3X, DDX5, DUSP6, EDN1, EGR2, EIF2S2, F2, F3, FBN1 |
| FOXM1 | 2.8 | 4.8E−05 | BIRC5, CCND1, CDC20, CDK1, CDKN1A, CENPA, CENPF, FOXM1, KDR, KIF20A, MMP2, PLK4, TGFBR2 |
| GLI2 | 2.7 | 3.2E−02 | CCL5, CCND1, CDK1, CDKN1A, IL1B, ITGB1, KRT1, KRT17, PTCH1, SFRP1 |
| MAX | 2.4 | 1.4E−03 | BCL6, CDKN1A, EDN1, FTH1, ID1, KLF6, LAMP2, MTHFD1, PDGFRB, SERINC3, TSC2, UBE2C |
| HNF1A | 2.1 | 3.6E−02 | ABCC2, AFP, AKR1C4, ALB, ANPEP, APOB, AQP9, BCL6, C2, CCND1, DPP4, DUSP6, FAM107B, FBXO8, FGA, FGB, G0S2, GNB2L1, HNF4A, IGFBP1, KIF20A, KIR3DL1, LCAT, MTHFD1, NAPA, PDK1, PFKP, PIH1D1, PRLR, PZP, SERPINA7, SLC26A1, SLCO1A2, SSTR4, TRA@, UQCRC2, UROD |
| | | | inhibited transcription factors and targets |
| CEBPB | −2.2 | 1.3E−11 | ACTG2, ALB, C3, CCL5, CCND1, CD14, CDKN1A, CEBPA, CEBPB, COL1A1, CP, CSF1R, CTSC, CXCL5, CYP19A1, DDX5, DEGS1, FTL, HLA-C, HP, HSPD1, ICAM1, ID1, IGFBP1, IL1B, IL1RN, IL8, INMT, IRF9, LAMC1, LCP2, LYN, MGP, MIA, PCTP, PDGFRA, PEA15, PLAUR, PPARD, PRKCD, PR |
| JUNB | −2.3 | 2.8E−03 | ACLY, CAV1, CCND1, CD68, CDC20, COL1A1, CYP19A1, FTH1, MMP2, MVD, NCF2, PTBP2, RELB, SCD |
| CIITA | −2.4 | 1.4E−07 | B2M, CCND1, CD74, COL1A1, HLA-B, HLA-DOB, HLA-DPA1, HLA-DQA1, HLA-DQB1, HLA-DRA, HLA-DRB1 |

TABLE 2-continued

Predicted transcription factors and targets identified among 1396 genes that passed Welch's t-test, FDR correction (q ≤ 0.05) and 1.5 fold change cutoff.

| TF | z-score | p-value | target molecules in dataset |
|---|---|---|---|
| POU2AF1 | −2.6 | 3.4E−03 | BCL6, CCND3, CD79A, CD79B, IGHA1, IGHG1, LCK, TRAF3 |
| STAT1 | −2.8 | 8.2E−12 | A2M, B2M, BIRC5, BTG1, C3, CASP1, CASP2, CASP4, CCL5, CCND1, CCND3, CCR7, CD14, CDKN1A, DPP4, FCER1G, GATA3, GBP1, GZMB, HLADRB1, ICAM1, IFIT3, IL1B, IL8, IRF1, IR5, IRF7, IRF9, LY96, NFE2, PDGFRB, PF4, PRL, PSMB10, PTGS2, SMAD7, SOCS3, STAT2, TLR4, TN |
| FOXO3 | −2.8 | 1.8E−04 | BIRC5, CCND1, CDKN1A, CTGF, CYR61, FOXM1, FOXO1, GPX1, IER3, IGFBP1, IL8, NAMPT, NOS3, SATB1, SOD2, TNFRSF1B, TXNIP, UBC, UBE2C |
| SPI1 | −2.9 | 1.5E−10 | ACTB, CCR7, CD14, CD68, CD79A, CD79B, CEBPA, CSF1R, CYBB, DUSP6, FCER1G, FLI1, FTH1, GNB2L1, GPX1, IGL@, IL1B, IL1RN, IRF9, ITGA5, ITGAM, ITGB2, MCL1, MMP2, NCF2, P2RY1, PIK3CG, PTGS2, PTPRC, RELA, TK1, TLR2, TLR4 |
| IFI16 | −3 | 1.8E−04 | CCL5, CCND1, CDKN1A, EDN1, GPX1, ICAM1, IFI16, IL1B, IL1RN, IL2RB, IL8, RPA3, STAT2 |
| HMGB1 | −3.1 | 1.6E−06 | CD83, CDKN1A, CXCL5, HLADRB1, ICAM1, IL1A, IL1B, IL8, MIA, PTGS2, RELB, SIRT1, TLR2, TLR4 |
| IRF1 | −3.2 | 1.0E−06 | B2M, CASP1, CASP2, CCL5, CCND1, CDKN1A, CYBB, EIF4A3, HLA-G, IFIT3, IL1B, IL8, IRF1, IRF5, IRF7, IRF9, LTB, NFE2, PF4, PSMB10, PTGS2, SOCS7, STAT2, TRIM22 |
| CREB1 | −3.4 | 1.5E−08 | ARPC3, ATP6V0B, BTG2, CCND1, CD3D, CD4, CD68, CD79A, CDH2, CEBPB, CYP19A1, CYP51A1, CYR61, DIO2, EDN1, EGR2, FN1, FOSB, GALNT1, HERPUD1, HLA-DRA, HLA-G, HMGCS1, HSPA4, IL1B, INHA, IRF7, MCL1, PDE3B, PDGFRA, PER1, PRL, PTGS2, SCD, SLC16A1, SLC2A4, SOD2, TF, TFAP2A, UPP1 |
| NFKB1 | −3.4 | 1.9E−08 | A2M, ADORA1, AKR1B1, B2M, BTG2, CCL5, CCND1, CDKN1A, COL2A1, CYBB, FANCD2, GATA3, GNB2L1, ICAM1, IER3, IFNGR2, IGHG1, IL1B, IL1RN, IL8, IRF1, LTB, MICA, NFKB1, NFKB2, PLK3, POU2F2, PRKACA, PTGS2, RELA, RELB, SOD2, TK1, TLR2, TNFAIP3 |
| RELA | −3.7 | 3.1E−17 | A2M, ABCG2, ACTA2, AFP, B2M, BIRC2, BTG2, CAV1, CCL5, CCND1, CCR7, CD44, CDKN1A, COL2A1, CXCL1, CYBB, CYP19A1, DIO2, EDN1, EWSR1, F3, GDF15, HLA-B, ICAM1, IER2, IER3, IFNGR2, IGHG1, IL1A, IL1B, IL1RN, IL8, INPP5D, IRF1, IRF7, L |
| IRF7 | −3.9 | 3.0E−03 | CASP4, CCL5, GBP1, IFI16, IFIT3, IRF1, IRF9, ISG20, ITGAM, MCL1, NAMPT, PSMB10, STAT2, TLR4, TMPO, TRIM21, TRIM22 |

Abbreviation: TF, transcription factor/regulator.
Regulation z-score; P-value overlap.

SUMMARY

Most immune response genes were down-regulated in post-Training leukocytes compared to pre-Training leukocytes. Functional enrichment of these down-regulated genes revealed their involvement in microbial pattern recognition, cytokine production and reception, chemotaxis, intercellular adhesion, immunological synapse formation, regulation of immune response, and activation and proliferation of immune cells (FIG. 8).

Figure 8:
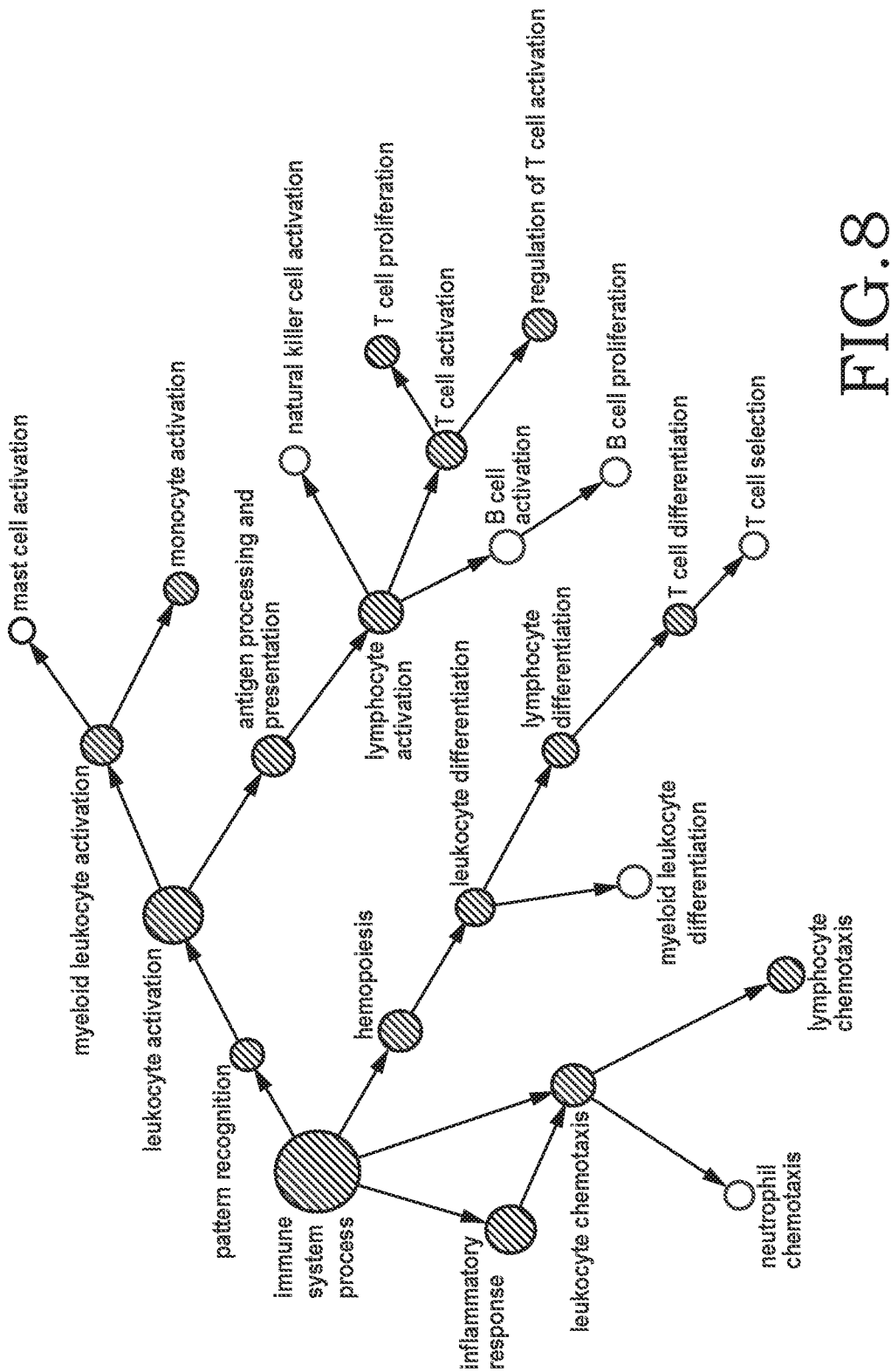
FIG. 8 is a map of functional network of differentially expressed genes connected by their sub-functions in the immune system.

FIG. 8 demonstrates a functional network of differentially expressed genes connected by their sub-functions in the immune system. The network shows enriched functions of genes involved in immune responses: activation of immune cells, differentiation, proliferation, antigen presentation, and infection directed migrations. Genes involved in all these functions were down regulated by the Ranger Training stressors. Each node represents a category of gene ontology of the pathways of the immune system. Node sizes are proportional to the number of genes belong to each category according to gene ontology, and intensity of node indicate significance of hypergeometric test after Bonferroni correction (q≤0.05). The pattern circles show more significant the enrichment than the solid white circles.

Figure 9A:
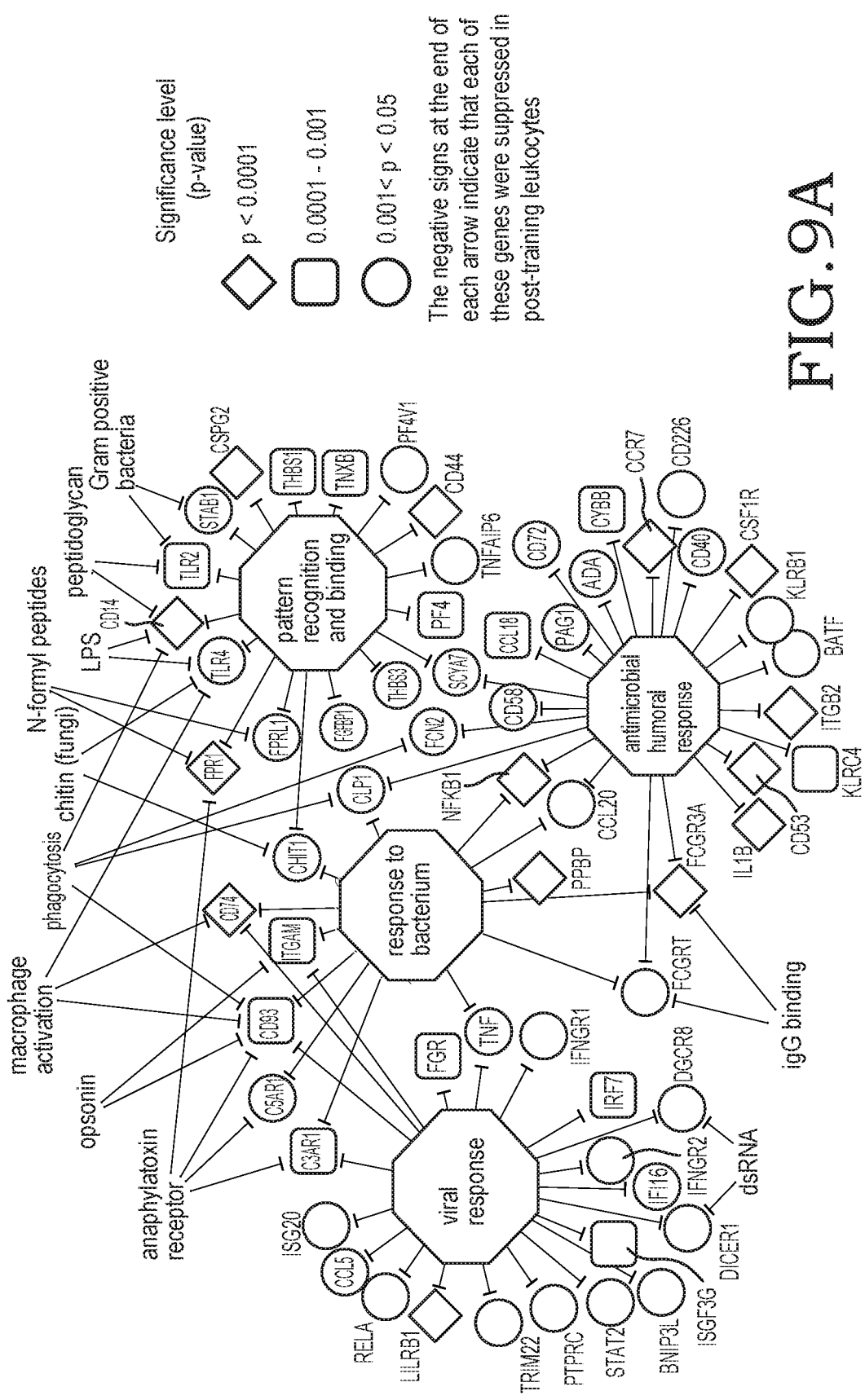
FIG. 9A is a map showing immune response transcripts involved in pattern recognition, viral, antibacterial and effector (humoral) responses.
Figure 9B:
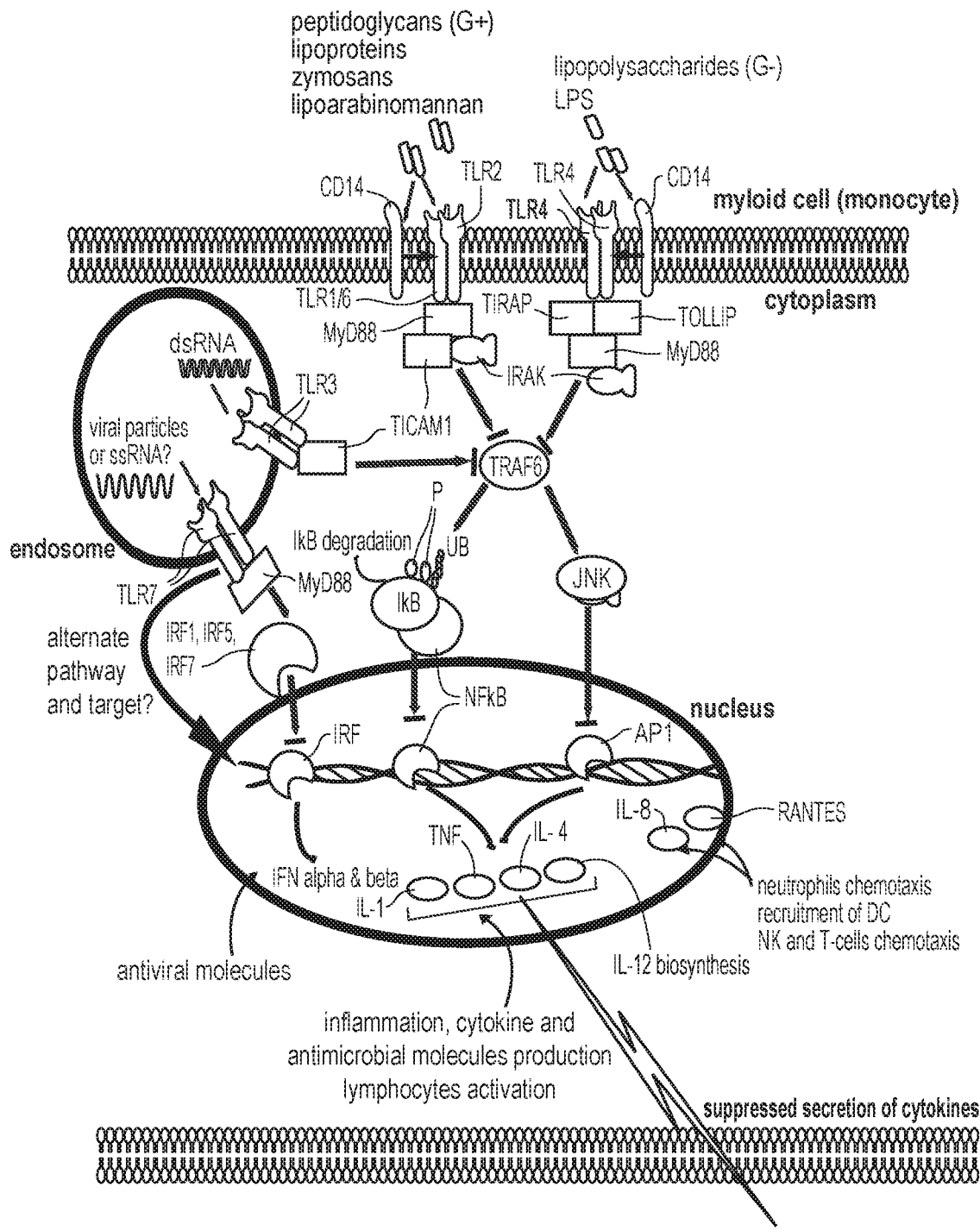
FIG. 9B is a diagram showing roles of stress down regulated genes in the cellular pathways of immune response.
Figure 9C:
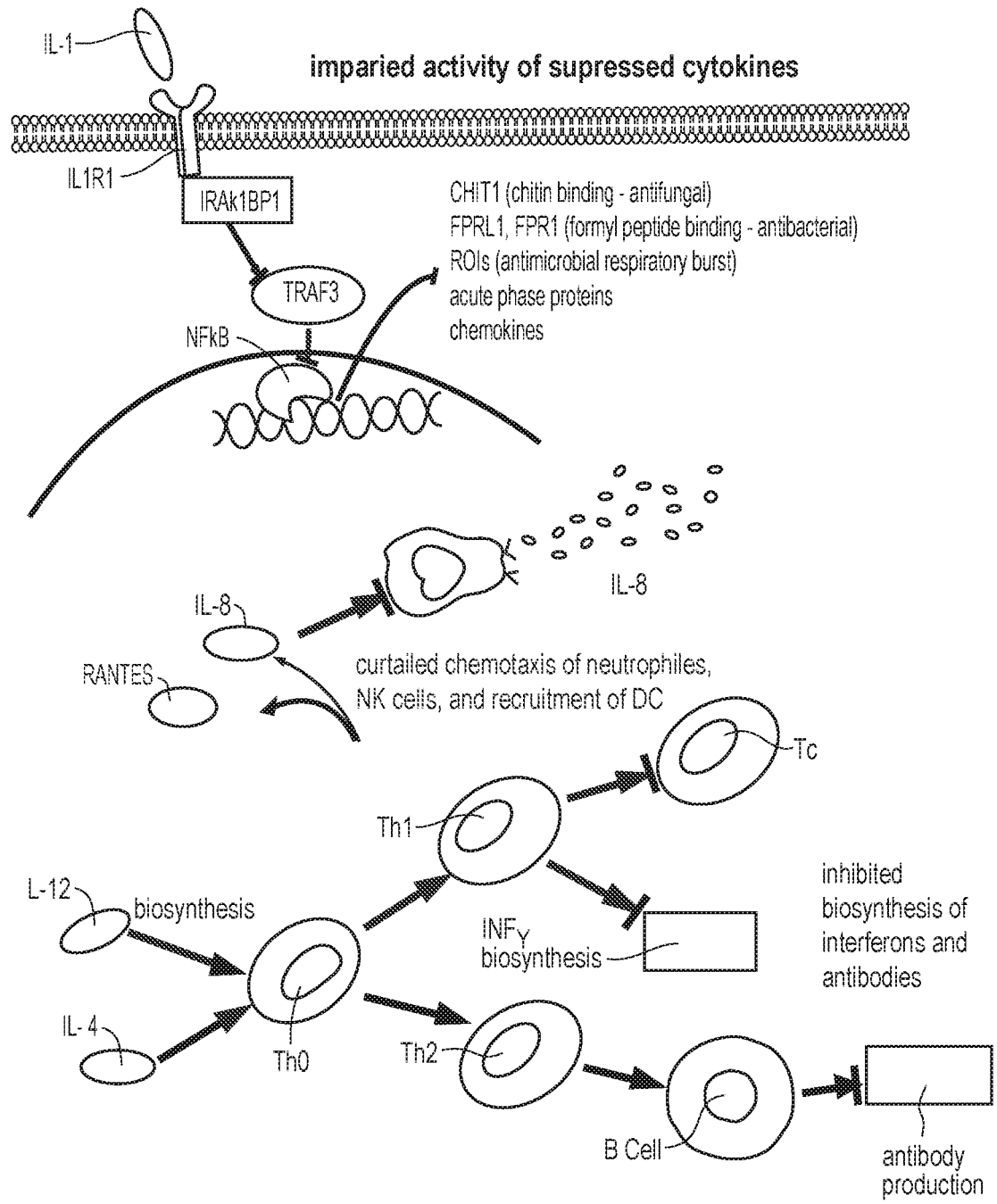
FIG. 9C is a diagram of action of secreted cytokines on other leukocytes.
Figure 10A:
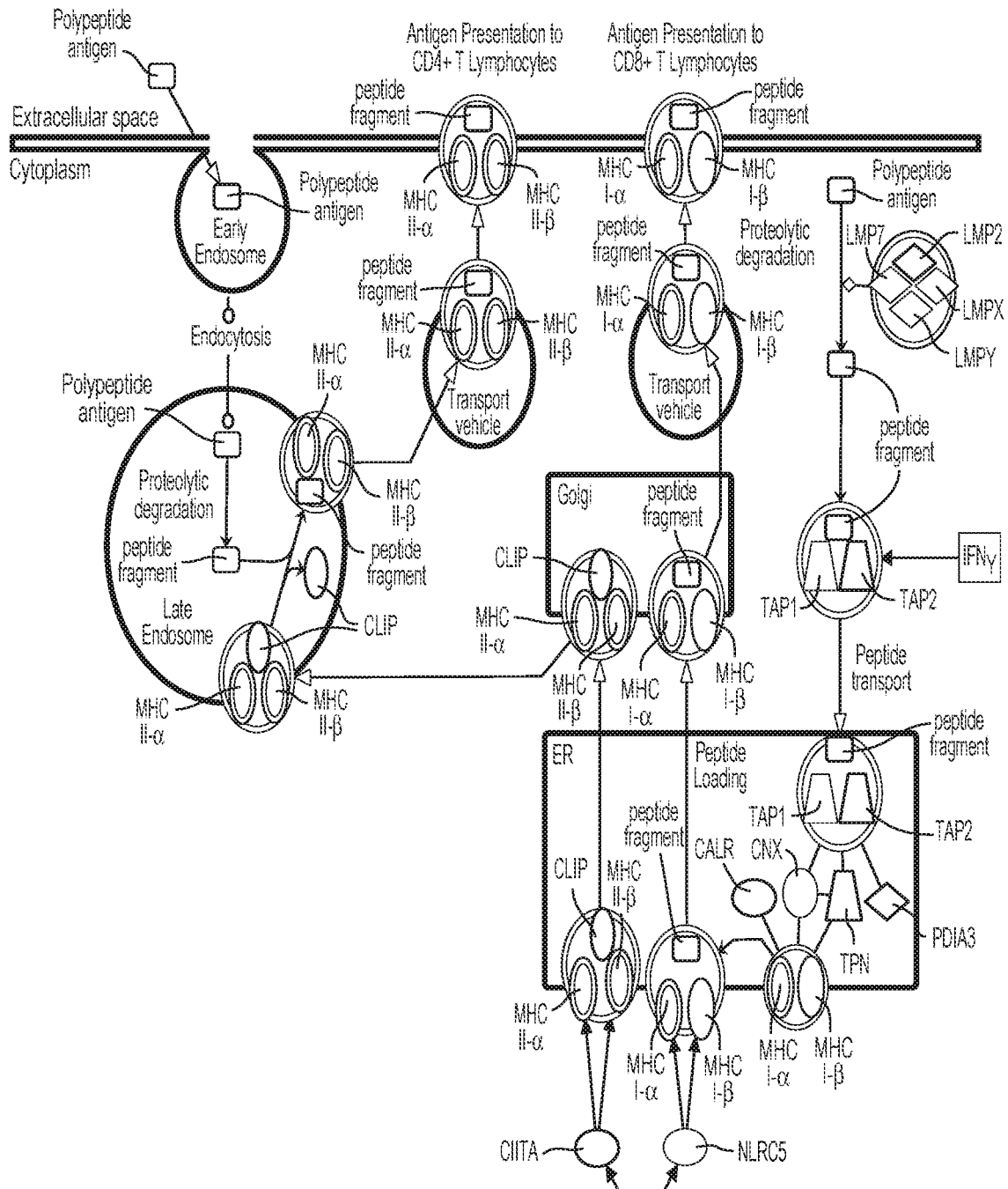
FIG. 10A is a diagram showing antigen presentation pathways.

Our data suggest that stress induced suppression of microbial patterns of innate immunity (FIG. 9A) may impair infection-directed maturation, activation, inflammatory response, motility, and proliferation of myeloid cells (FIGS. 9B & 9C) These impaired innate cells may also fail in priming the adaptive arm of immune response (FIG. 10A).

In FIG. 9A, shows altered immune response genes involved in pattern recognition, viral, antibacterial effector (humoral) responses.

In FIG. 9B, roles of stress down regulated genes in the cellular pathways of immune response are shown. Flat-ended arrows represent suppression of the corresponding pathway (biological process). Microbial recognition receptors, inflammatory cytokines (IL1, IL1R, TNFα, CD40), chemotaxis (IL8, IL8R, RANTES, CCR5, CCR7), lymphocyte recruitment (IL4, IL 12), and production of effector molecules (INFγ, IL2, IL2RB) were down regulated after Ranger Training In FIG. 9C, actions of secreted cytokines on other leukocytes are shown. Impaired activity of suppressed IL-1 other myeloid cells to secret antimicrobial effector molecules; depleted concentration gradient of IL-8 providing curtailed guidance to neutrophils and NK cells to sites of infection, and suppressed IL-8 and RANTES unable to recruit and induce maturation of dendritic cells (for antigen presentation); suppressed transcripts important for T-cell polarization (cellular or humoral) may mean deprivation of the host under stress from having protective immunity.

Figure 10B:
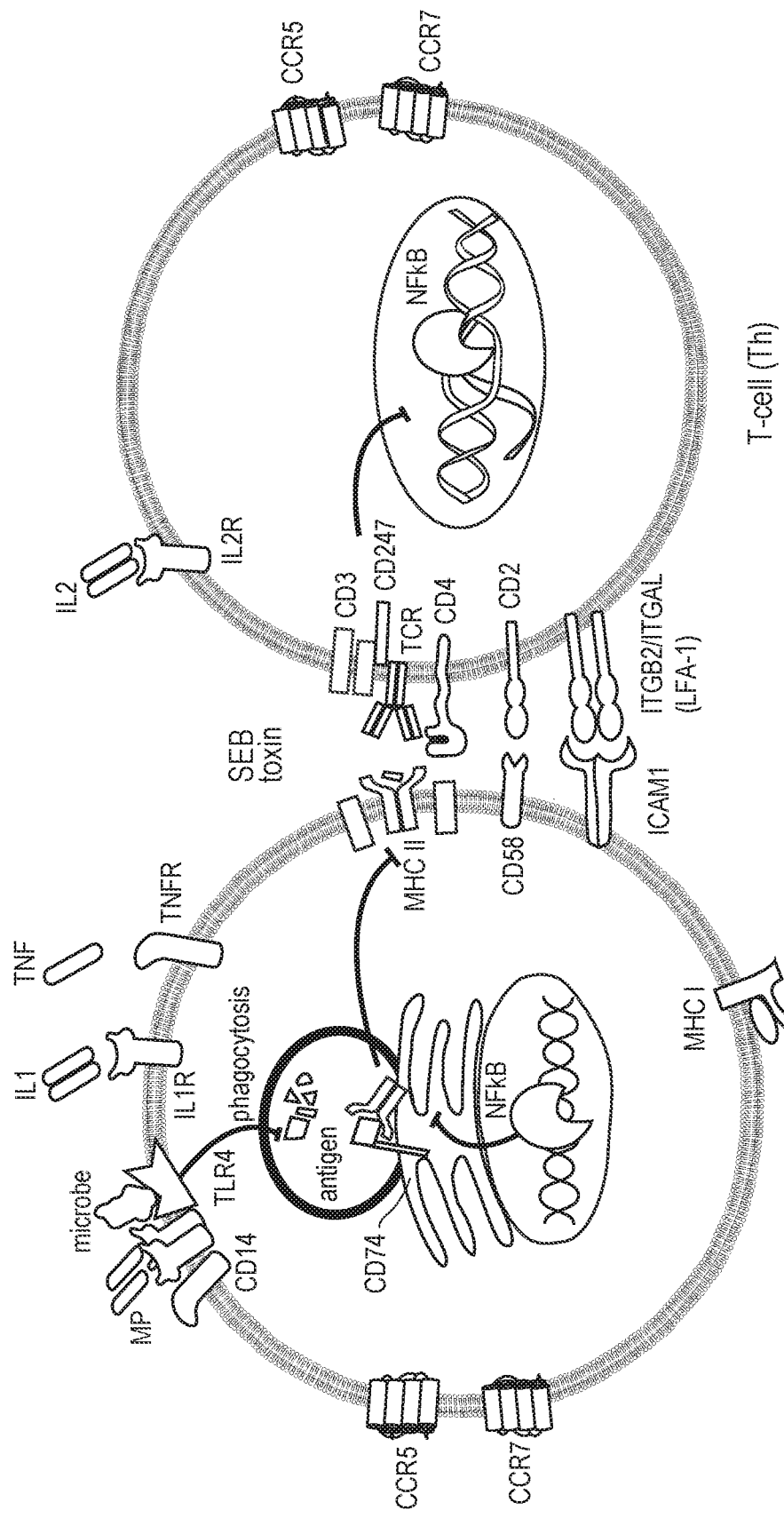
FIG. 10B is a diagram showing expression pattern of genes important for immunological synapse formation.
Figure 11:
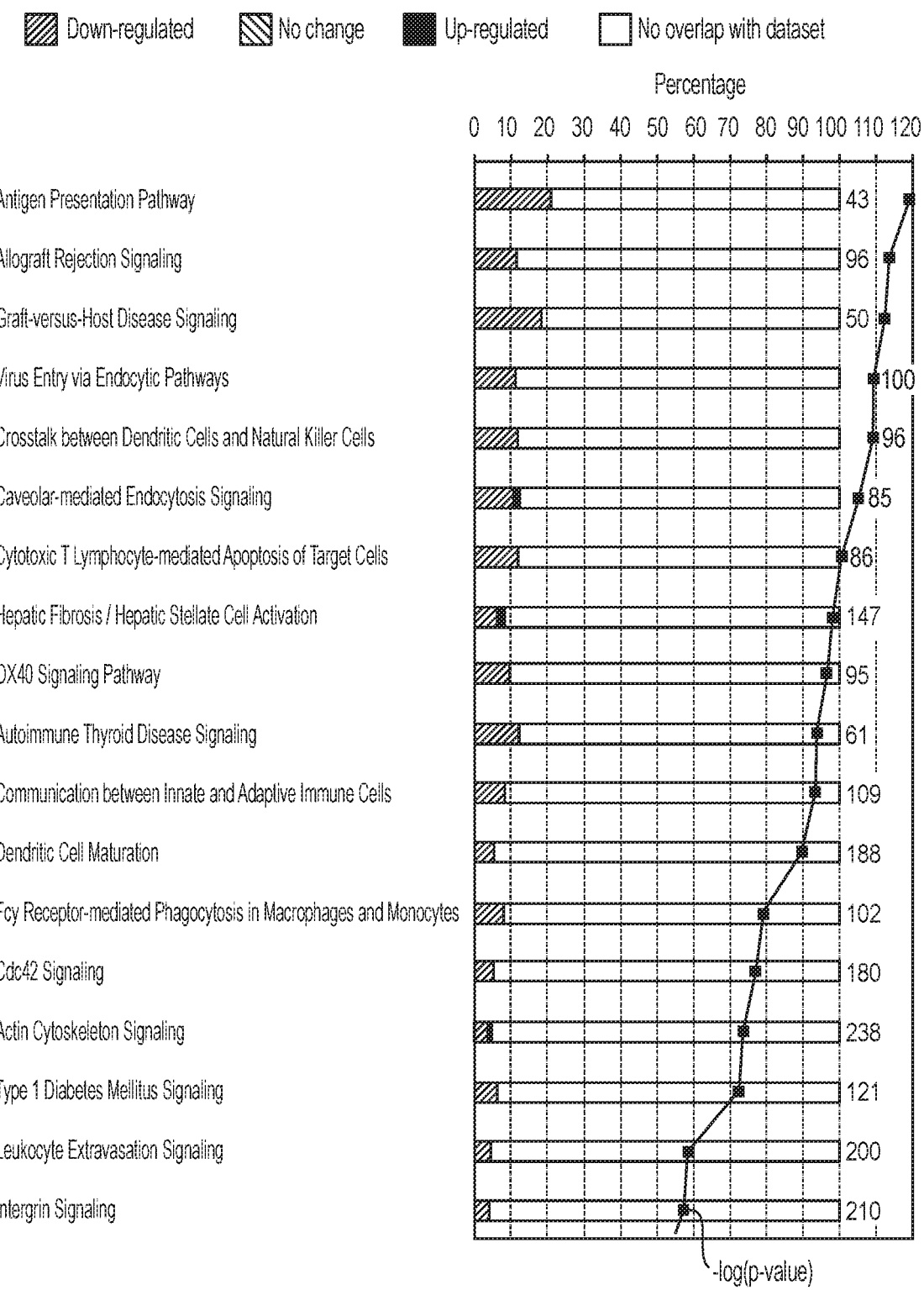
FIG. 11 is a diagram showing Canonical pathways significantly associated with stress regulated genes that passed Welch's t-test and FDR correction ($p<=0.001$) and 1.5 fold change.
Figure 12:
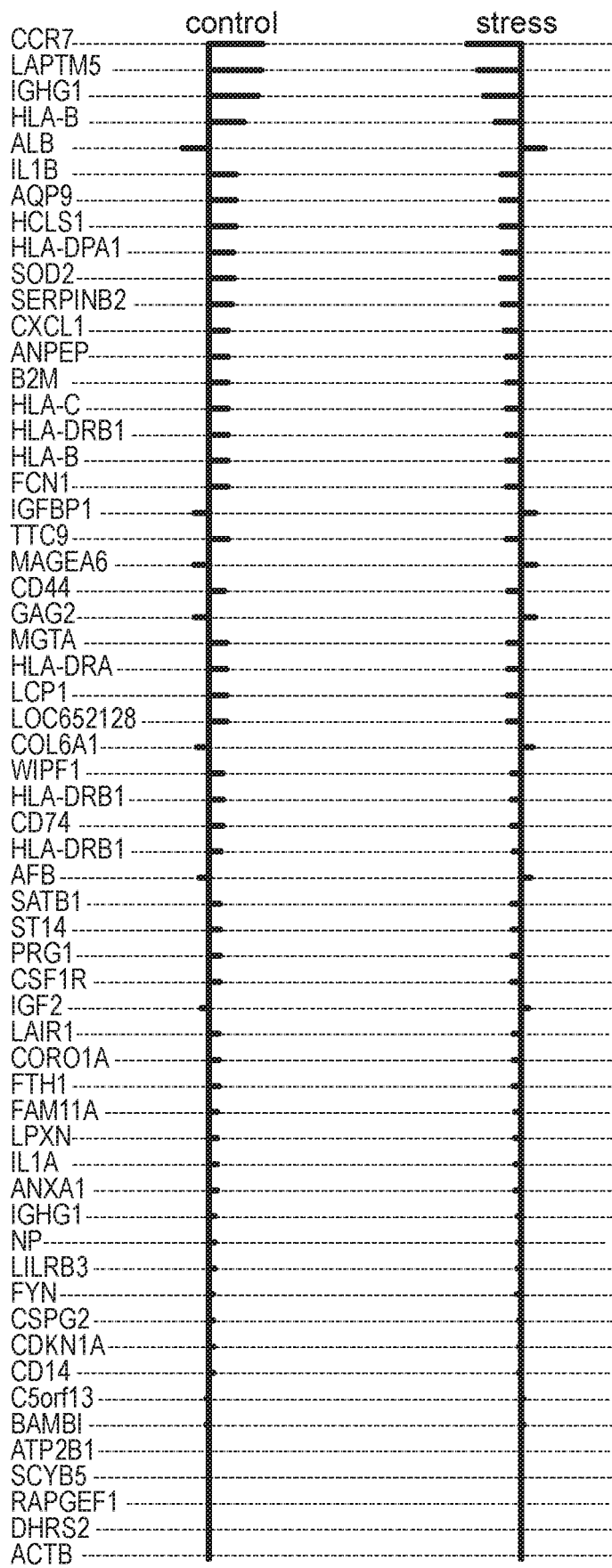
FIG. 12 is a graph showing relative contribution (rank) of genes in classifying (predicting) control and stress groups of Ranger samples ranked using the Nearest shrunken centroid prediction approach.
Figure 13A:
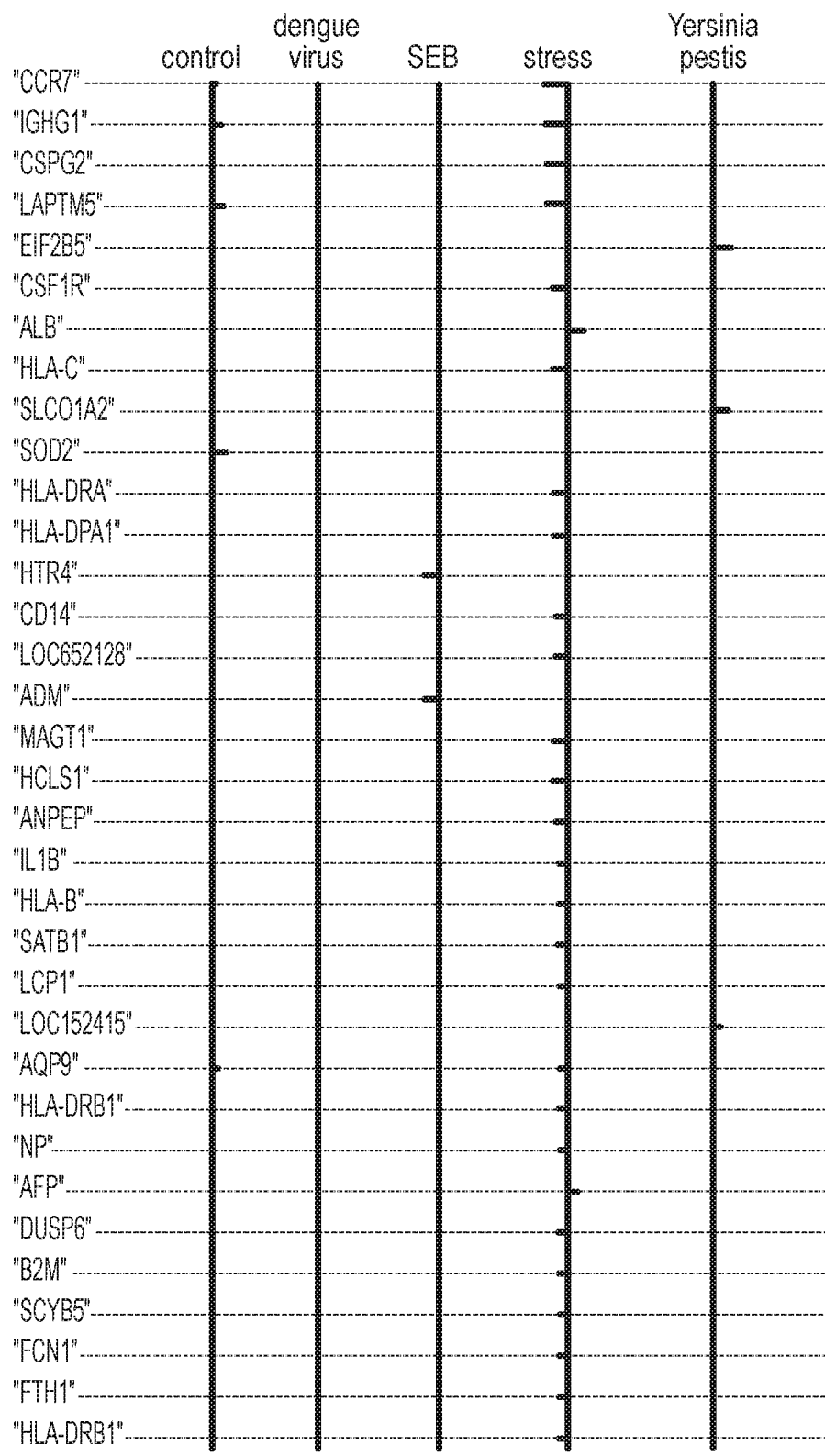
FIG. 13A is a graph showing stress specific genes differentiating stress from SEB, dengue virus and *Yersinia pestis* (plague) infections.
Figure 13B:
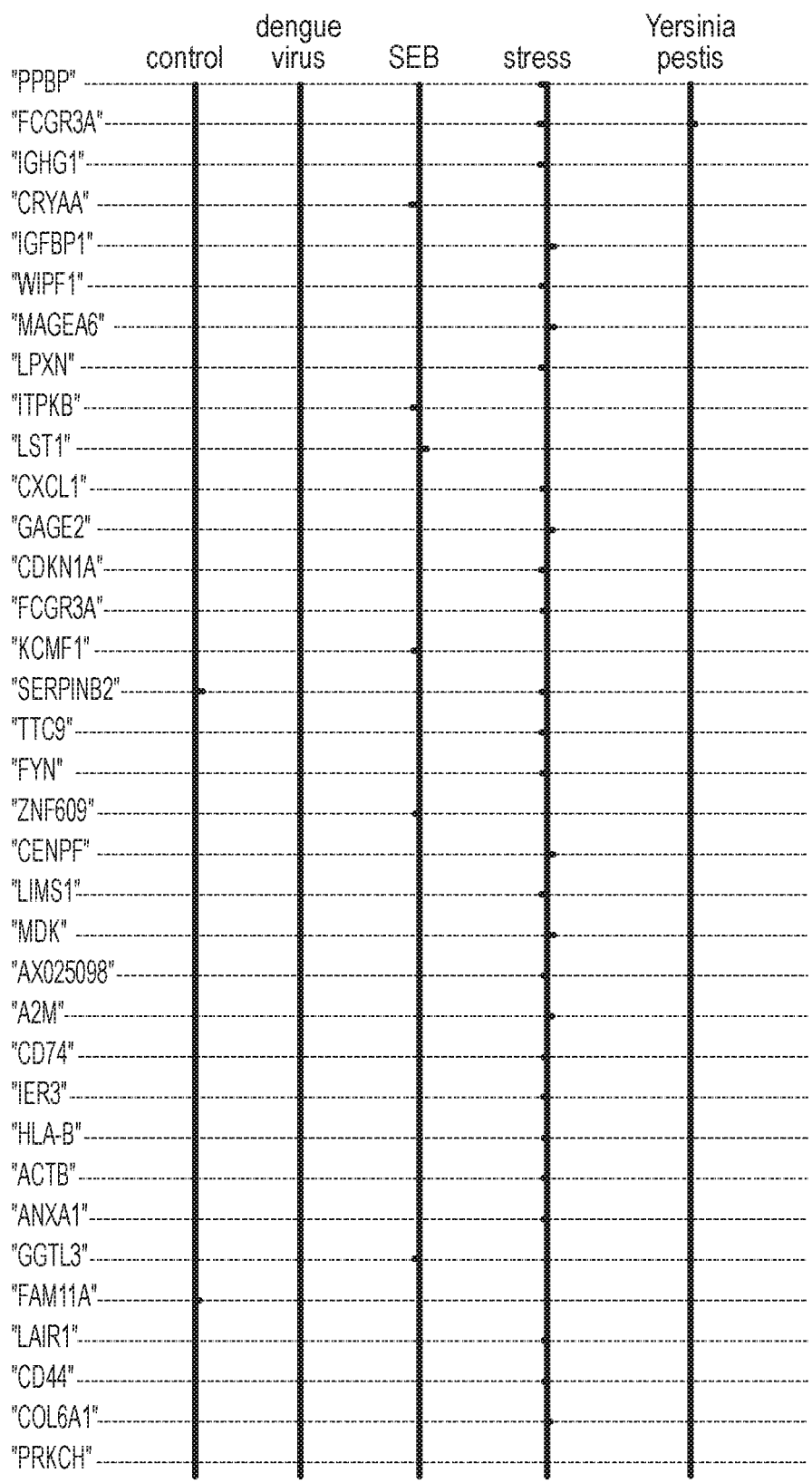
FIG. 13B is also a graph showing stress specific genes differentiating stress from SEB, dengue virus and *Yersinia pestis* (plague) infections.
Figure 14:
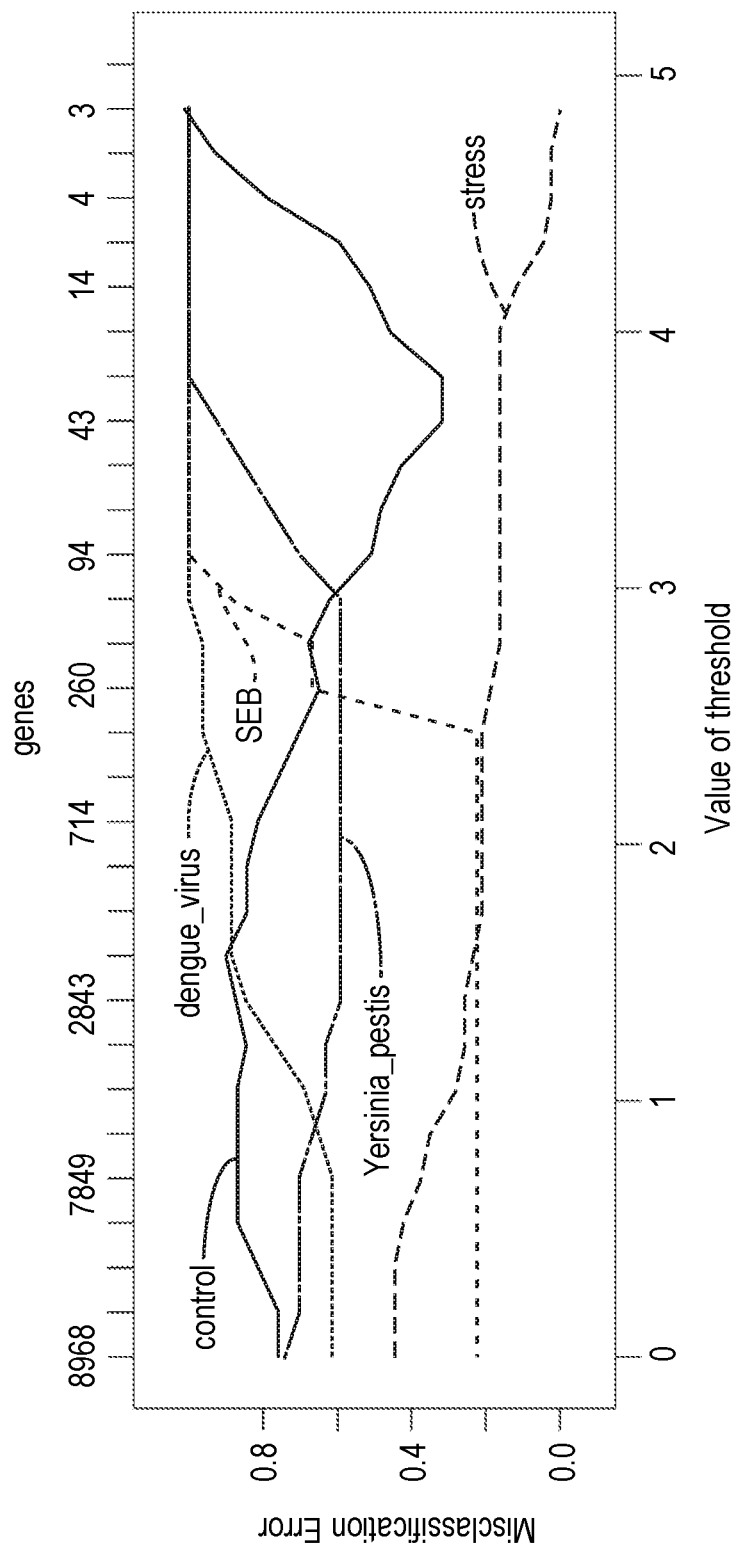
FIG. 14 is a graph showing misclassification error rate vs threshold value.

FIGS. 10A and 10B show stress-suppressed genes involved in antigen presentation and synapse formation. FIG. 10A shows antigen presentation pathways: This KEEG pathway taken via IPA was colored for the 288 stress-regulated genes that passed Welch's t-test, FDR correction (q≤0.001) and changed by ≥1.5 fold (between pre- and post-Training groups).

FIG. 10B shows expression of genes important for immunological synapse formation; suppression of transcripts important in antigen preparation, presentation, chemotaxis, intercellular binding, antigen reception, and downstream signaling (the gene labeled solid nodes) may have impaired formation of productive immunological synapse, and hence the poor response of post-Training leukocytes to SEB challenge although SEB toxin is presented without undergoing intracellular preparation, antigen presenting molecules of the synapse were suppressed.

Adaptive cells' antigen receptors, co-receptors, signal transducers, intercellular adhesion molecules, and chemokine receptors were highly suppressed (FIG. 10B). It is less likely that these stress-debilitated lymphocytes can be activated, proliferated, differentiated, and clonally expanded to amount defense response against infections as confirmed by impaired response of post-Training leukocytes to SEB exposure.

Discussion

Suppression of transcripts of critical immune response pathways, and regulatory networks are consistent with impaired innate and adaptive immune responses, including cellular and humoral immunity, as a result of battlefield-like stress.

Down-regulation of transcripts involved in Toll-like receptor, and chemokine and chemokine receptor signaling pathways indicate suppressed inflammatory response, impaired maturation of antigen presenting cells (APCs), impaired affinity maturation of integrins, and impaired migration, extravasation & homing of APCs and T-cells to nearby draining lymph nodes or infection sites.

Antigen preparation and presentation was the most suppressed pathway among immune response processes (FIG. 11). FIG. 11 shows canonical pathways significantly associated with stress-regulated genes that passed Welch's t-test and FDR correction ($p<=0.001$) and 1.5 fold change. Numbers on the right side indicate total # of genes in the pathway. Suppression of antigen presentation, T-cell receptor and integrin pathways indicate lack of productive immunological synapse formation (poor MHC-restricted antigen recognition and T-cell activation), leading to impaired adaptive and effector immune responses. Particularly, suppression of transcripts involved in cytoskeleton-dependent processes (chemokine guided migration, integrin-mediated adhesion, immunological-synapse formation, cellular polarization, and actin-microtubule aided receptor sequestration and signaling) curtails the dynamic cellular framework of T-cell activations (FIG. 10).

Unlike reports of differential regulations of Th1 and Th2 type responses observed in college students on the day of a stressful examination[15], and in caregivers of chronically sick relatives[16], our data suggest that battlefield-like stressors impair not only Th1 but also Th2 type responses as shown by suppressed transcripts of TLR2 and 4, and the cytokines IL4, IL4R and IL10RA in post-Training leukocytes. Suppression of inflammatory molecules (e.g., IL1A & 1B, and IL1R1, TNF members and TNF receptors, and NFkB class of factors), and Th2 classes of cytokines show features of battlefield-like stress that are distinct from acute and psychological stresses.

Previously miR-155 is reported to be proinflammatory. MiR-155 (−/−) mice are highly resistant to experimental autoimmune encephalomyelitis[17], and show suppressed antigen-specific helper cell, and markedly reduced articular inflammation[18]. Here, miR-155 transcripts were elevated in post-Training leukocytes (with or without SEB exposure), but its expression was suppressed by SEB in pre-training leukocytes (FIG. 6).

It seems that miR-155 is anti-inflammatory in humans exposed to stress and SEB toxin. Regulatory connection of miR-155 to many of stress-suppressed inflammatory cytokines may indicate its involvement in regulation of these cytokines, and glucocorticoid receptor elements, and modulate maturation of antigen presenting cells under battlefield-like stress.

Poor response of post-Training leukocytes to SEB ex vivo challenge is consistent with suppressed expression of MHCs, T-cell receptors, co-receptors and integrins which are important for activations of APCs and T-cells. Overall, our results clearly demonstrated that battlefield-like stressors suppress a broad spectrum of immune system process. This suppression of broad categories of immune response pathways may explain why chronically stressed individuals show poor vaccine responses and susceptibility to infections.

FIGS. 12-15 were generated from nearest shrunken centroid prediction. The Nearest Shrunken Centroid (NSC) classifier (predictor) is a robust[21-22] way of identifying genes specific to a certain agent in the presence of other infections or conditions[23]. NSC was used successfully to identify cancer biomarkers[24-25] and other disease sub-typing[26-27].

FIG. 12 is a graphical representation of Nearest shrunken centroid (NSC) ranked genes when stressed and control groups compared. The length of the horizontal bars indicate the absolute value of the score (the bigger the absolute value of the score the longer the horizontal bar, and the direction indicate the gene expression direction (left oriented bar indicate down-regulated and right oriented bar up-regulated genes). Here only two groups are compared and the opposite orientations of the horizontal bars indicate that these genes discriminate between the two compared groups.

FIGS. 13A and 13B are graphical representations of NSC algorithm identified genes which can discriminate stress and other conditions (dengue virus exposure, *Yersinia pestis* or plague infection and SEB toxin exposure; and also unexposed control group). The direction and length of the horizontal bars is given in FIG. 12. As shown in FIGS. 13 A&B there are 69 genes including 10 specific to the other pathogens that are shown by the corresponding horizontal bars.

FIG. 14 shows misclassification error versus threshold (cut-off) values, each line representing each condition. Here the stress (black line) has the lowest misclassification error beyond the threshold value of around 2.6. That means, genes ranked from one to about 260 can discriminate stress from other conditions (shown here). But in our case we took the top ranked genes (even though many more can also be potential stress biomarkers).

FIG. 15 is a graph showing that identified genes were cross-validated to ascertain that they were not included by mere chance. The more open circles (under stress) being separated from other shapes indicate that these genes discriminate stressed individuals from other patients (samples collected from patients exposed to other pathogens or control group). Though there is shown in FIG. 15 only 114 samples, the total number of samples used for prediction were 141.

Conclusion

Suppressed expression of genes critical to innate, humoral and cellular immunity is an indicator of compromised protective immunity as confirmed by impaired response of post-Training leukocytes to SEB challenge. Numbers and ratios of different subpopulations of leukocytes being within normal ranges, our observation (of anergic leukocytes of severely stressed individuals) draws some caution on current diagnostic practice of counting immune cells to ascertain integrity of the immune system, and its ability of protection against infection.

On the basis of suppressed inflammatory molecules and pathways, we hypothesized that exposure to battlefield-like and similar stresses may make exposed individuals less susceptible to autoimmune diseases, and sepsis; yet they may easily succumb to toxin or infection since their protective immunity already depleted.

Characterization of molecular signatures of stress pathologies can potentially reveal biomarkers and new pharmacologic targets for improving adaptation to stress and preventing stress-induced pathogenesis. Results such as ours together with proteomic analyses may yield novel preventative, prognostic and therapeutic opportunities to intervene the negative consequences of stress on heath.

Materials and Methods

Blood Sample Collection

Whole blood (from each subject) was drawn in Leucopack tubes (BRT Laboratories Inc., Baltimore, Md.) before and after the eight-week Training, and immediately spun at 200×g for 10 minutes. The concentrated leukocyte layer (buffy coats) was collected and treated with TRIzol™ reagent (Invitrogen, Carlsbad, Calif.) for RNA isolation and then stored at −80° C. Differential and complete blood counts (CBC) were obtained immediately after blood collection using a hemocytometer, and subsequently using an ABX PENTRA C+ 60 flow cytometer (Horiba ABX, Irvine, Calif.). Blood samples were also collected in PAXgene™ Blood RNA Tubes (VWR Scientific, Buffalo Grove, Ill.) for direct RNA isolation.

RNA Isolation

For cDNA microarray analysis, total RNA was isolated using the TRIzol™ reagent according to the manufacturer's instructions. The RNA samples were treated with DNase-1 (Invitrogen, Carlsbad, Calif.) to remove genomic DNA and were re-precipitated by isopropanol. The TRIzol™ isolated RNA was used in cDNA microarrays analysis[19]. For oligonucleotide microarrays, total RNA was isolated using PAXgene tubes following the manufacturer's protocol. The PAXgene tube contains a proprietary reagent that immediately stabilizes RNA at room temperature (18-25° C.) without freezing. Isolated RNA samples were stored at −80° C. until they were used for microarray and real time PCR analyses. The concentration and integrity of RNA were determined using an Agilent 2000 BioAnalyzer (Palo Alto, Calif.) according to manufacturer's instructions. The ArrayControl RNA Spikes from Ambion (Austin, Tex.) were used to monitor RNA integrity in hybridization, reverse transcription and RNA labeling.

cDNA Synthesis, Labeling, Hybridization and Image Processing

RNA was reverse transcribed and labeled using Micromax Tyramide Signal Amplification (TSA) Labeling and Detection Kit (Perkin Elmer, Inc., Waltham, Mass.) following the manufacturer's protocol. The slides were hybridized at 60° C. for 16 h (for cDNA microarrays and Trizol isolated RNA) and at 55° C. for 16 h (for oligonucleotide microarrays and PAXgen isolated RNA). Hybridized slides were scanned and recorded using a GenePix Pro 4000B (Axon Instruments Inc., Union City, Calif.) optical scanner, and the data were documented using Gene Pix 6.0 (Axon Instruments Inc, Union City, Calif.).

Preparation of cDNA Microarrays

Human cDNA microarrays were prepared using sequence-verified PCR elements produced from ~10,000 well-characterized human genes of The Easy to Spot Human UniGEM V2.0 cDNA Library (Incyte Genomics Inc., Wilmington, Del.). The PCR products, ranging from 500 to 700 base pairs, were deposited in 3× saline sodium citrate (SSC) at an average concentration of 165 µg/ml on CMT-GAPS™ II (γ-aminopropylsilane) coated slides (Corning Inc., Corning, N.Y.), using a Bio-Rad VersArray MicroArrayer (Hercules, Calif.). The cDNAs were UV-cross-linked at 120 mJ/cm² using UV Stratalinker® 2400 from Stratagene (La Jolla, Calif.). The microarrays were baked at 80° C. for 4 h. The slides were treated with succinic anhydride and N-methyl-2-pyrrolidinone to remove excess amines.

Oligonucleotide Microarrays

The Human Genome Array Ready Oligo Set Version 3.0 Set from Operon Biotechnologies (Huntsville, Ala.) includes 34,580 oligonucleotide probes representing 24,650 genes and 37,123 RNA transcripts from the human genome. The oligonucleotide targets were deposited in 3× saline sodium citrate (SSC) at an average concentration of 165 µg/ml onto CMT-GAPS II aminopropylsilane-coated slides (Corning, Corning, N.Y.) using a VersArray Microarrayer. Microarrays were UV-crosslinked at 120 mJ/cm² using UV Stratalinker® 2400. Then slides were baked at 80° C. for 4 hours, and were treated with succinic anhydride and N-methyl-2-pyrrolidinone to remove excess amines on the slide surface. Slides were stored in boxes with slide racks and the boxes were kept in desiccators.

Real Time QPCR

Quantitative real time PCR arrays of one hundred genes associated with inflammation, transcription factors, and antigen preparation and presentation pathways were carried out using Dendritic & Antigen Presenting Cell Pathway (PAHS 406) and NFkB Pathway (PAHS 25) RT² Profiler™ PCR Arrays (SABiosciences, Frederick, Md.) according to manufacturer's instructions. Four replicates of RNA samples isolated using PAXgene™ from Trainees before and after Training were assayed. The data were analyzed using ABiosciences' web-based software.

Reverse transcriptase reagent (iScript) and real time PCR master mix (QuantiTect™ SYBR® Green PCR Kit) were obtained from BioRad Inc., CA and QIAGEN Inc., Valencia, Calif., respectively. Real time polymerase chain reactions (PCR) were carried out in i-Cycler Real-time PCR apparatus (BioRad Inc, Milpitas, Calif.), using three to five biological replicates for each primer pair (based on sample availability). The custom oligonucleotide primers were designed using Primer3 software, or based on those from UniSTS and Universal Probe Library for Human (Roche Applied Science). Their specificities were verified in the BLAST domain at NCBI. Parallel amplification reaction using 18S rRNA primers was carried out as a control. Threshold cycle (Ct) for every run was recorded and then converted to fold change using the equation: $[(1+E)^{\Delta Ct}]_{GOI}/[(1+E)^{\Delta Ct}]_{HKG}$, where ΔCt stands for the difference between Ct of control and treated samples of a given gene, which is either gene of interest (GOI) or housekeeping genes (HKG), and E stands for primer efficiency, calculated from slope of best fitting standard curve of each primer pair.

ELISA

Plasma concentrations of prolactin (PRL), insulin-like growth factors I and II (IGF-I & II), tumor necrosis factor alpha (TNFα), and enzymatic activity of superoxide dismutase were determined using ELISA kits from Calbiotech, Inc. (Spring Valley, Calif., Catalog #PR063F), Diagnostic Systems Laboratories, Inc. (Webster, Tex., Catalog #s DSL-10-2800 and DSL-10-2600), Quantikine® of R&D Systems, Inc. (Minneapolis, Minn., Catalog #DTA00C) and Dojindo Molecular Technologies, Inc (Gaithersburg, Md., Catalog #S311), respectively, following manufacturers' protocols.

Microarray Data Analyses

Background and foreground pixels of the fluorescence intensity of each spot on the microarrays were segmented using ImaGene (BioDiscovery Inc., El Segundo, Calif.) and the spots with the highest 20% of the background and the lowest 20% of the signal were discarded. Local background correction was applied. Genes that passed this filter in all experiments were selected for further study. Then, sub-grid based Lowes normalization was performed for each chip independently. Additional per spot (dividing by control channel) and per gene (to specific samples) normalization were also performed under the Genespring GX platform (Agilent Technologies Inc, Santa Clara, Calif.). Statistical analysis was computed using Welch's t-test (p<0.05) with Benjamini and Hochberg False Discovery Rate (FDR) Multiple Correction to select the genes with high altered expression (for cDNA microarray data, but oligonucleotide microarray data were analyzed without FDR Correction). Two-dimensional clustering was carried out based on samples and genes for visualization and assessment of reproducibility in the profile of the significant genes across biological replicates.

Interaction Networks and Gene Ontology Enrichment

Bingo 2.3 was used for gene ontology enrichment with hypergeometric distribution with FDR (false discover rate) or Bonferroni corrections (p<0.05). Biological processes, molecular functions, and cellular components of each cluster of genes were compared to the global annotations and over-represented categories after corrections were analyzed and visualized. Functional analysis and pathways associated with stress and pathogen-regulated genes were analyzed using Ingenuity Pathway Analysis (Ingenuity Systems Inc.; Redwood City, Calif.). Cytoscape Version 2.6.1 was used for visualizing and analyzing enriched gene ontologies, and molecular interaction network constructions.

MicroRNA Analysis

Expression profiles of MicroRNAs were assayed using Agilent's human miRNA v3 microarray (Agilent Technologies Inc) consisting of 15 k targets representing 961 microRNAs. Differentially expressed microRNAs were analyzed using Qlucore Omices Explorer 2.2 (Qlucore AB) and GeneSpring GX 11.5 (Agilent Technologies Inc.). Target transcripts of profiled microRNAs were identified using target scan of Genespring, and Ingenuity Pathway Analysis (IPA) (Ingenuity Systems Inc.). Interaction networks of differentially expressed microRNAs and their target mRNAs were constructed using IPA.

Treatment of Leukocytes with Staphylococcal Enterotoxin B (SEB)

Leukocytes isolated from leucopack blood samples were plated in six well tissue culture plates (~$10^6$ cells/ml in RPMI 1640 and 10% human AB serum) and treated with SEB (Toxin Technology Inc., Sarasota, Fla.) at a final concentration of 100 ng/ml SEB. Cells were incubated for 6 h at 37° C. and 5% $CO_2$. At the end of the incubation period, treated leukocytes were collected by centrifugation at 350×g for 15 minutes. Cell pellets were treated with 2 ml TRIzol™ and kept at −80° C. for RNA isolation.

cDNA Microarray (Expression) Data Based Prediction of Transcription Factors, Regulatory Binding Sites and Downstream Target Identification Potential regulatory sites of differentially regulated genes were identified using HumanGenome9999 (Agilent Technologies Inc., CA) containing partial human genome sequences (9999 bp upstream region for 21787 genes). Statistically significant (p<0.05) common regulatory motifs of 5 to 12 nucleotides long were identified. The searching region was set to range 1 to 500 nucleotides upstream of transcription start sites. Other tools used for this purpose include MATCH and TFSEARCH. Cognate transcription factors of identified (common regulatory) sites were searched from different prediction and repository databases: DBD, JASPAR, TRANSFAC® 7.0—Public using Chip-MAPPER[20], ConTra, Pscan and Ingenuity Pathway Analysis (IPA, ingenuity inc). Expression databased prediction Z-scores and regulatory targets were analyzed using IPA. Regulator-target interaction networks and pathways were generated using Cytoscape (Cytoscape.org) and IPA.

TABLE 3A

Transcripts that have passed Welch's T-TEST (& Bonferroni correction at q < 0.01), and selected from battlefield-like condition that have Normalized Data values greater or less than those in baseline condition by a factor of 3 fold (59 transcripts)

| ID | q-value | Fold change | Symbol | UniGene | Description |
|---|---|---|---|---|---|
| AU119825 | 0.000726 | 3.29 | A2M | Hs.212838 | Alpha-2-macroglobulin |
| BE889785 | 0.00932 | −3.28 | ACSL1 | Hs.406678 | Acyl-CoA synthetase long-chain family member 1 |
| AL558086 | 0.000818 | 9.06 | ALB | Hs.418167 | Albumin |
| NM_001150 | 1.86E−05 | −5.52 | ANPEP | Hs.1239 | Alanyl (membrane) aminopeptidase (aminopeptidase N, aminopeptidase M, microsomal aminopeptidase, CD13, p150) [up-regulated in late adenovirus type-12 infection (Journal of Virology 2005, 79: 4, 2404)] |
| BG541130 | 0.000667 | −3.52 | ANXA1 | Hs.494173 | Annexin A1 |
| NM_020980 | 5.62E−05 | −8.06 | AQP9 | Hs.104624 | Aquaporin 9 [Dehydration/osmotic adaptation in yeast (JBC 2005; 280: 8, 7186); specialized leukocyte functions such as immunological response and bactericidal activity (PUBMED)] |
| BF432072 | 0.00212 | −3.68 | ATP2B1 | Hs.506276 | ATPase, Ca++ transporting, plasma membrane 1 |
| AV710740 | 4.47E−07 | −3.91 | B2M | Hs.534255 | Beta-2-microglobulin |
| NM_012342 | 0.00103 | 3.36 | BAMBI | Hs.533336 | BMP and activin membrane-bound inhibitor homolog (*Xenopus laevis*) |

TABLE 3A-continued

Transcripts that have passed Welch's T-TEST (& Bonferroni correction at q < 0.01), and selected from battlefield-like condition that have Normalized Data values greater or less than those in baseline condition by a factor of 3 fold (59 transcripts)

| ID | q-value | Fold change | Symbol | UniGene | Description |
|---|---|---|---|---|---|
| AI348005 | 0.00671 | −3.42 | BTG1L | Hs.710041 | Similar to B-cell translocation gene 1, |
| XM_008651 | 4.30E−07 | −16.98 | CCR7 | | chemokine (C-C motif) receptor 7 [suppression lead to impaired lymphocyte migration, delayed adaptive immune response (cell 1999), CCR7 is key mediator in balancing immunity and tolerance, abnormalities contribute to immune dysregulation (clinical and experimental immunology, 2009)] |
| AL549182 | 0.00137 | −3.46 | CD14 | Hs.163867 | CD14 molecule |
| M24915 | 0.000223 | −4.9 | CD44 | Hs.502328 | CD44 molecule (Indian blood group) |
| BG333618 | 0.00854 | −12.3 | CD74 | Hs.436568 | CD74 molecule, major histocompatibility complex, class II invariant chain |
| L26165 | 0.00869 | −3.8 | CDKN1A | Hs.370771 | Cyclin-dependent kinase inhibitor 1A (p21, Cip1) |
| NM_005196 | 0.00289 | 3.08 | CENPF | | synonyms: CENF, PRO1779; centromere protein F (400 kD); centromere protein F (350/400 kD, mitosin); CENP-F kinetochore protein; AH antigen; cell-cycle-dependent 350K nuclear protein; *Homo sapiens* centromere protein F, 350/400ka (mitosin) (CENPF), mRNA. |
| AL570594 | 5.07E−05 | 4.15 | COL6A1 | Hs.474053 | Collagen, type VI, alpha 1 |
| BE252062 | 0.000478 | −3.92 | CORO1A | Hs.474053 | Coronin, actin binding protein, 1A |
| NM_005211 | 6.28E−06 | −3.25 | CSF1R | Hs.586219 | Colony stimulating factor 1 receptor, formerly McDonough feline sarcoma viral (v-fms) oncogene homolog |
| AU118073 | 0.00469 | −4.52 | CSPG2/ VCAN | Hs.643801 | Chondroitin sulfate proteoglycan 2 (versican) |
| BG491425 | 0.000933 | −15.22 | CXCL1 | Hs.789 | Chemokine (C-X-C motif) ligand 1 (melanoma growth stimulating activity, alpha) [involved in neurophil recruitment (Shock 35: 6, 604)] |
| NM_005366 | 0.000153 | −3.34 | MAGEA11 | Hs.670252 | Melanoma antigen family A, 11 |
| AL583593 | 0.0035 | −7.3 | FCN1 | Hs.440898 | Ficolin (collagen/fibrinogen domain containing) 1 [expressed at the cell surface of monocytes and granulocytes and its receptor is found at activated but not resting T lympohcytes (journal of leukocyte biology 2010; 88; 1: 145); it is part of the innate immune system and function as recognition molecules in the complement system (Journal of innate immunity 2010; 2: 1, 3)] |
| NM_013409 | 0.002 | 3.01 | FST | Hs.9914 | Follistatin |
| Z97989 | 0.00897 | −3.82 | FYN | | FYN oncogene related to SRC, FGR, YES |
| NM_001472 | 9.99E−06 | 3.82 | GAGE7 | Hs.460641 | G antigen 7 |
| AL551154 | 0.000131 | −6.99 | HCLS1 | Hs.14601 | Hematopoietic cell-specific Lyn substrate 1 [induces G-CSF-Triggered Granulopoiesis Via LEF-1 Transcription Factor (blood 2010 114: 22, 229); mutation defects at HCLS1 with Kostmann disease, recombinant human granulocyte colony-stimulating factor (G-CSF), the prognosis and quality of life improved dramatically (European Journal of Pediatrics 2010, 169: 6, 659)] |
| BG327758 | 0.00021 | −15.13 | HLA-B | Hs.77961 | Major histocompatibility complex, class I, B |
| BE168491 | 0.00123 | −7.63 | HLA-C | Hs.654404 | Major histocompatibility complex, class I, C |
| AW407113 | 2.66E−05 | −5.29 | IGKV@, | Hs.660766 | Immunoglobulin kappa variable group |
| AV759427 | 0.000205 | −6.8 | HLA-DPA1 | Hs.347270 | Major histocompatibility complex, class II, DP alpha 1 |
| BF795929 | 0.00253 | −8.33 | HLA-DRA | Hs.520048 | Major histocompatibility complex, class II, DR alpha |
| M20503 | 0.000575 | −11.82 | HLA-DRB1/ HLA-DRB5 | Hs.696211/ Hs.696211 | Major histocompatibility complex, class II, DR beta 1/5 |
| BF974114 | 0.00046 | −5.24 | HLA-DRB1 | Hs.696211 | Major histocompatibility complex, class II, DR beta 1 |

TABLE 3A-continued

Transcripts that have passed Welch's T-TEST (& Bonferroni correction at q < 0.01), and selected from battlefield-like condition that have Normalized Data values greater or less than those in baseline condition by a factor of 3 fold (59 transcripts)

| ID | q-value | Fold change | Symbol | UniGene | Description |
|---|---|---|---|---|---|
| BF732822 | 0.000358 | −4.98 | HLA-DRB1 | Hs.696211 | Major histocompatibility complex, class II, DR beta 1 |
| AW411300 | 0.00267 | 4.36 | IGF2 | Hs.272259 | Insulin-like growth factor 2 (somatomedin A) |
| AL542262 | 0.00121 | 5.48 | IGFBP1 | Hs.642938 | Insulin-like growth factor binding protein 1 |
| AI634950 | 9.18E−07 | −11.82 | IGHG1 | Hs.510635 | Immunoglobulin heavy constant gamma 1 (G1m marker) |
| AA490743 | 0.001 | −4.61 | IGHG1 | Hs.510635 | Immunoglobulin heavy constant gamma 1 (G1m marker) |
| NM_000575 | 0.00594 | −5.15 | IL1A | Hs.1722 | Interleukin 1, alpha |
| W38319 | 6.35E−06 | −6.29 | IL1B | Hs.126256 | Interleukin 1, beta |
| AU122160 | 0.000811 | −4.17 | LAIR1 | Hs.572535 | Leukocyte-associated immunoglobulin-like receptor 1 |
| NM_006762 | 5.04E−07 | −16.13 | LAPTM5 | Hs.371021 | Lysosomal associated multispanning membrane protein 5 [negative regulation of cell surface BCR levels and B cell activation (The Journal of Immunology, 2010, 185: 294-301); LAPTM5 negatively regulated surface TCR expression by specifically interacting with the invariant signal-transducing CD3 zeta chain and promoting its degradation without affecting other CD3 proteins, CD3 epsilon, CD3 delta, or CD3 gamma (IMMUNITY 29: 1 Pages: 33-43)] |
| BF035921 | 0.000407 | −4.65 | LCP1 | Hs.381099 | Lymphocyte cytosolic protein 1 (L-plastin) |
| NM_024318 | 0.000838 | −3.65 | LILRA6 | Hs.688335 | Leukocyte immunoglobulin-like receptor, subfamily A (with TM domain), member 6 |
| AL560682 | 0.00115 | −8.2 | IG heavy chain/ LOC652128 | Hs.703938 | Immunoglobulin Heavy Chain Variable region |
| NM_004811 | 0.0021 | −4.12 | LPXN | Hs.125474 | Leupaxin |
| BF792356 | 1.21E−05 | 4.04 | MAGEA6 | Hs.441113 | Melanoma antigen family A, 6 |
| AW966037 | 0.000159 | 3.1 | MDK | Hs.82045 | Midkine (neurite growth-promoting factor 2) |
| BE742106 | 9.14E−06 | −4.03 | MGAT1 | Hs.519818 | Mannosyl (alpha-1,3-)-glycoprotein beta-1,2-N-acetylglucosaminyltransferase |
| NM_002473 | 0.00506 | −3.39 | MYH9 | Hs.474751 | Myosin, heavy chain 9, non-muscle |
| AU142621 | 0.00726 | −4.46 | PNP | Hs.75514 | Nucleoside phosphorylase |
| XM_007374 | 0.00795 | −3.25 | PRKCH | | protein kinase C, eta |
| BE266904 | 7.79E−05 | −4.15 | SATB1 | Hs.517717 | Special AT-rich sequence binding protein 1 (binds to nuclear matrix/scaffold-associating DNA's) |
| AL550163 | 0.00157 | −28.25 | SERPINB2 | Hs.594481 | Serpin peptidase inhibitor, clade B (ovalbumin), member 2 [upregulated under different inflammatory conditions, null mice showed increased TH1 response, secreted by macrophages, hemotpoeitic and nonhematopoeitic cells] |
| BG035651 | 0.00108 | −10.34 | SOD2 | Hs.487046 | Superoxide dismutase 2, mitochondrial [Conditional loss of SOD2 led to increased superoxide, apoptosis, and developmental defects in the T cell population, resulting in immunodeficiency and susceptibility to the influenza A virus H1N1 (Free radical biology and medicine, 201; 50: 3, 448); manipuation of SOD2 affects drosophila survival under stress (PLoS One 2011; 6: 5, e19866)] |
| AL548113 | 4.31E−05 | −3.28 | ST14 | Hs.504315 | Suppression of tumorigenicity 14 (colon carcinoma) |
| D86980 | 3.55E−07 | −3.57 | TTC9 | Hs.79170 | Tetratricopeptide repeat domain 9 |
| NM_003387 | 2.52E−05 | −4.05 | WIPF1 | Hs.128067 | WAS/WASL interacting protein family, member 1 |

TABLE 3B

Top 59 of stress specific genes ranked in order:

| Rank | Gene Accession | Gene Name | Control | Dengue Virus | SEB | Stress | Yersinia Pestis | Description |
|---|---|---|---|---|---|---|---|---|
| 1 | XM_008651 | CCR7 | 0.0943 | 0 | 0 | −0.2854 | 0 | chemokine (C-C motif) receptor 7 |
| 2 | AI634950 | IGHG1 | 0.1285 | 0 | 0 | −0.2723 | 0 | Immunoglobulin heavy constant gamma 1 (G1m marker) |
| 3 | AU118073 | CSPG2 | 0 | 0 | 0 | −0.2638 | 0.0673 | Chondroitin sulfate proteoglycan 2 |
| 4 | NM_006762 | LAPTM5 | 0.1751 | 0 | 0 | −0.2592 | 0 | Lysosomal associated multispanning membrane protein 5 |
| 5 | NM_005211 | CSF1R | 0 | 0 | 0 | −0.2147 | 0 | Colony stimulating factor 1 receptor, |
| 6 | AL558086 | ALB | −0.0559 | 0 | 0 | 0.2136 | 0 | Albumin |
| 7 | AW407113 | HLA-C | 0 | 0 | 0 | −0.2119 | 0 | Major histocompatibility complex, class I, C |
| 8 | BF795929 | HLA-DRA | 0 | 0 | 0 | −0.193 | 0 | Major histocompatibility complex, class II, DR alpha |
| 9 | AV759427 | HLA-DPA1 | 0 | 0 | 0 | −0.1885 | 0 | Major histocompatibility complex, class II, DP alpha 1 |
| 10 | AL549182 | CD14 | 0 | 0 | 0 | −0.187 | 0.0541 | CD14 molecule |
| 11 | AL560682 | LOC652128 | 0 | 0 | 0 | −0.183 | 0 | Similar to Ig heavy chain V-II region ARH-77 precursor |
| 12 | BE742106 | MGAT1 | 0 | 0 | 0 | −0.1764 | 0 | Mannosyl (alpha-1,3-)-glycoprotein beta-1,2-N-acetylglucosaminyl transferase |
| 13 | AL551154 | HCLS1 | 0.0306 | 0 | 0 | −0.1738 | 0 | Hematopoietic cell-specific Lyn substrate 1 |
| 14 | NM_001150 | ANPEP | 0.0331 | 0 | 0 | −0.1713 | 0 | Alanyl (membrane) aminopeptidase (aminopeptidase N, aminopeptidase M, microsomal aminopeptidase, CD13, p150) |
| 15 | W38319 | IL1B | 0.0424 | 0 | 0 | −0.1624 | 0 | Interleukin 1, beta |
| 16 | BG327758 | IL1B | 0.0702 | 0 | 0 | −0.1618 | 0 | Major histocompatibility complex, class I, B |
| 17 | BE266904 | SATB1 | 0 | 0 | 0 | −0.1566 | 0 | Special AT-rich sequence binding protein 1 (binds to nuclear matrix/scaffold-associating DNA's) |
| 18 | BF035921 | LCP1 | 0 | 0 | 0 | −0.1546 | 0 | Lymphocyte cytosolic protein 1 (L-plastin) |
| 19 | NM_020980 | AQP9 | 0.0815 | 0 | 0 | −0.1491 | 0 | Aquaporin 9 |
| 20 | M20503 | HLA-DRB1 | 0.0071 | 0 | 0 | −0.147 | 0 | Major histocompatibility complex, class II, DR beta 1 |
| 21 | AU142621 | NP | 0 | 0 | 0 | −0.1463 | 0 | Nucleoside phosphorylase |
| 22 | AA334424 | AFP | 0 | 0 | 0 | 0.1439 | 0 | Alpha-fetoprotein |
| 23 | NM_001946 | DUSP6 | 0 | 0 | 0 | −0.1433 | 0.0044 | Dual specificity phosphatase 6 |
| 24 | AV710740 | B2M | 0.0427 | 0 | 0 | −0.1403 | 0 | Beta-2-microglobulin |

TABLE 3B-continued

Top 59 of stress specific genes ranked in order:

| Rank | Gene Accession | Gene Name | Control | Dengue Virus | SEB | Stress | Yersinia Pestis | Description |
|---|---|---|---|---|---|---|---|---|
| 25 | XM_003507 | SCYB5 | 0 | 0 | 0 | −0.1371 | 0 | small inducible cytokine subfamily B (Cys-X-Cys), |
| 26 | AL583593 | FCN1 | 0.0203 | 0 | 0 | −0.1359 | 0 | Ficolin (collagen/fibrinogen domain containing) 1 |
| 27 | BE878314 | FTH1 | 0 | 0 | 0 | −0.1346 | 0 | Ferritin, heavy polypeptide 1 |
| 28 | BF732822 | HLA-DRB1 | 0 | 0 | 0 | −0.1318 | 0 | Major histocompatibility complex, class II, DR beta 1 |
| 29 | XM_003506 | PPBP | 0 | 0 | 0 | −0.1312 | 0 | pro-platelet basic protein (includes platelet basic |
| 30 | J04162 | FCGR3A | 0 | 0 | 0 | −0.1308 | 0.0905 | Fc fragment of IgG, low affinity IIIa, receptor (CD16a) |
| 31 | AA490743 | IGHG1 | 0 | 0 | 0 | −0.1254 | 0 | Immunoglobulin heavy constant gamma 1 (G1m marker) |
| 32 | AL542262 | IGFBP1 | 0 | 0 | 0 | 0.1214 | 0 | Insulin-like growth factor binding protein 1 |
| 33 | NM_003387 | WIPF1 | 0 | 0 | 0 | −0.1193 | 0 | WAS/WASL interacting protein family, member 1 |
| 34 | BF792356 | MAGEA6 | −0.0079 | 0 | 0 | 0.1181 | 0 | Melanoma antigen family A, 6 |
| 35 | NM_004811 | LPXN | 0 | 0 | 0 | −0.1162 | 0 | Leupaxin |
| 36 | BG491425 | CXCL1 | 0 | 0 | 0 | −0.1138 | 0 | Chemokine (C—X—C motif) ligand 1 |
| 37 | NM_001472 | GAGE2 | −0.0189 | 0 | 0 | 0.1127 | 0 | G antigen 2 |
| 38 | L26165 | CDKN1A | 0 | 0 | 0 | −0.1121 | 0 | Cyclin-dependent kinase inhibitor 1A (p21, Cip1) |
| 39 | NM_000569 | FCGR3A | 0 | 0 | 0 | −0.1107 | 0 | Fc fragment of IgG, low affinity IIIa, receptor (CD16a) |
| 40 | D86980 | TTC9 | 0.0306 | 0 | 0 | −0.0992 | 0 | Tetratricopeptide repeat domain 9 |
| 41 | Z97989 | FYN | 0 | 0 | 0 | −0.0989 | 0 | FYN oncogene related to SRC, FGR, YES |
| 42 | AL550163 | SERPINB2 | 0.1069 | 0 | 0 | −0.0971 | 0 | Serpin peptidase inhibitor, clade B (ovalbumin), member 2 |
| 43 | NM_005196 | CENPF | 0 | 0 | 0 | 0.095 | 0 | Homo sapiens centromere protein F, 350/400ka (mitosin) (CENPF), mRNA. |
| 44 | NM_004987 | LIMS1 | 0 | 0 | 0 | −0.0887 | 0 | LIM and senescent cell antigen-like domains 1 |
| 45 | AW966037 | MDK | 0 | 0 | 0 | 0.0877 | 0 | Midkine (neurite growth-promoting factor 2) |
| 46 | AX025098 | AX025098 | 0 | 0 | 0 | −0.0871 | 0 | unnamed protein product; Sequence 22 from Patent WO0031532. |
| 47 | AU119825 | A2M | 0 | 0 | 0 | 0.0867 | 0 | Alpha-2-macroglobulin |

TABLE 3B-continued

Top 59 of stress specific genes ranked in order:

| Rank | Gene Accession | Gene Name | Control | Dengue Virus | SEB | Stress | Yersinia Pestis | Description |
|---|---|---|---|---|---|---|---|---|
| 48 | BG333618 | CD74 | 0 | 0 | 0 | −0.0847 | 0 | CD74 molecule, major histocompatibility complex, class II invariant chain |
| 49 | N32077 | IER3 | 0 | 0 | 0 | −0.082 | 0 | Immediate early response 3 |
| 50 | BE168491 | HLA-B | 0.0089 | 0 | 0 | −0.0816 | 0 | Major histocompatibility complex, class I, B |
| 51 | BG481840 | ACTB | 0 | 0 | 0 | −0.0773 | 0 | Actin, beta |
| 52 | BG541130 | ANXA1 | 0 | 0 | 0 | −0.074 | 0 | Annexin A1 |
| 53 | AU122160 | LAIR1 | 0.0158 | 0 | 0 | −0.0709 | 0 | Leukocyte-associated immunoglobulin-like receptor 1 |
| 54 | M24915 | CD44 | 0.0216 | 0 | 0 | −0.0704 | 0 | CD44 molecule |
| 55 | AL570594 | COL6A1 | 0 | 0 | 0 | 0.0678 | 0 | Collagen, type VI, alpha 1 |
| 56 | XM_007374 | PRKCH | 0 | 0 | 0 | −0.0676 | 0 | protein kinase C, eta |
| 57 | AA583143 | MAFB | 0 | 0 | 0 | −0.0638 | 0 | V-maf musculoaponeurotic fibrosarcoma oncogene homolog B |
| 58 | XM_008466 | EVI2A | 0 | 0 | 0 | −0.063 | 0 | ecotropic viral integration site 2A |
| 59 | AA309971 | LAT | 0 | 0 | 0 | −0.0619 | 0 | Linker for activation of T cells |

TABLE 4

After 8 weeks: Transcripts profiled using quantitative real time QPCR arrays (116 transcripts were down-regulated, and 3 were up-regulated)

| Symbol | Fold | StdevRTPCR |
|---|---|---|
| IKBKG | −12.6188 | 0.339657363 |
| RELB | −12.2737 | 0.284777655 |
| IRAK1 | −9.2375 | 0.360943649 |
| HGDC | −6.8685 | 0.390462704 |
| JUN | −5.9484 | 0.27944997 |
| TNFSF14 | −4.7158 | 0.433281621 |
| RELA | −3.9724 | 0.63019443 |
| CD40 | −3.7974 | 0.189280078 |
| FADD | −3.6364 | 0.367498363 |
| PPM1A | −3.5988 | 0.27174874 |
| INHBA | −3.5247 | 0.104573154 |
| CSF1R | −3.1821 | 0.758689626 |
| CXCL10 | −3.1766 | 0.277406814 |
| AKT1 | −3.1059 | 0.367849974 |
| TNFRSF1A | −2.9079 | 0.687128349 |
| ACTB | −2.8481 | 0.351350801 |
| TRADD | −2.8432 | 0.506924503 |
| TLR9 | −2.8382 | 0.289278965 |
| TNFRSF10B | −2.8284 | 0.267218757 |
| LTBR | −2.5847 | 0.570855834 |
| CXCL1 | −2.5403 | 0.579529817 |
| FCER2 | −2.5184 | 0.414730623 |
| SLC44A2 | −2.4967 | −0.822611762 |
| HMOX1 | −2.4368 | 0.155559063 |
| CCL4 | −2.4116 | 0.533964145 |
| CD209 | −2.4074 | 0.197647764 |
| IKBKE | −2.3784 | 0.555233712 |
| ICAM1 | −2.3335 | 0.437161543 |
| HLA-A | −2.3295 | 1.214034504 |
| ELK1 | −2.3254 | 0.269089688 |
| CCL3L1 | −2.2462 | 0.27090657 |
| TNFAIP3 | −2.2346 | 0.389174835 |
| TLR6 | −2.2191 | 0.872877926 |
| HLA-DOA | −2.2153 | 0.607988424 |
| MAP3K1 | −2.2115 | 0.61339209 |
| IKBKB | −2.1962 | 0.538167096 |
| NFKBIA | −2.1772 | 0.152911234 |
| F2R | −2.1473 | 0.243094984 |
| CDKN1A | −2.1287 | 0.707160113 |
| CFB | −2.1287 | 0.164433367 |
| CD28 | −2.114 | 0.214883087 |
| IL16 | −2.0958 | −6.38481053 |
| ERBB2 | −2.0777 | 0.192737356 |
| IRAK2 | −2.0669 | 0.234239489 |
| CD1D | −2.035 | 0.200278319 |
| TLR2 | −2.0279 | −2.201882954 |
| CCL8 | −2.0139 | 0.148872434 |
| CD4 | −2 | 0.616064291 |
| HLA-DMA | −1.9793 | 1.430015754 |
| FASLG | −1.9725 | 0.132549302 |
| CCL11 | −1.9252 | 0.137200432 |
| CCL13 | −1.9252 | 0.137200432 |
| CCL16 | −1.9252 | 0.137200432 |
| CCL7 | −1.9252 | 0.137200432 |
| CXCL12 | −1.9252 | 0.137200432 |
| CXCL2 | −1.9252 | 0.137200432 |
| FCAR | −1.9252 | 0.137200432 |
| IL2 | −1.9252 | 0.137200432 |
| MDK | −1.9252 | 0.137200432 |
| TNFSF11 | −1.9252 | 0.137200432 |
| IL12B | −1.8823 | 0.139095667 |
| CD40 | −1.8693 | 0.396668136 |
| HLA-DPA1 | −1.8693 | −92.22884305 |
| RELB | −1.8661 | 0.207774407 |

TABLE 4-continued

After 8 weeks: Transcripts profiled using quantitative real time QPCR arrays (116 transcripts were down-regulated, and 3 transcripts were up-regulated)

| Symbol | Fold | StdevRTPCR |
|---|---|---|
| REL | −1.8628 | 0.585844588 |
| TLR1 | −1.8628 | 0.602086965 |
| CD2 | −1.8468 | 0.857944585 |
| ICAM1 | −1.8182 | 0.63392797 |
| TAPBP | −1.8119 | 0.419814619 |
| RELA | −1.7932 | 0.273669806 |
| CASP8 | −1.7777 | 0.21122336 |
| IL1R1 | −1.7685 | 0.524613114 |
| TICAM2 | −1.7623 | 0.216623278 |
| CD1B | −1.7381 | 0.132080179 |
| CEBPA | −1.7112 | 0.784622441 |
| CASP1 | −1.7082 | 0.934618998 |
| STAT1 | −1.7082 | 0.964130752 |
| TLR4 | −1.7082 | 0.580800815 |
| RAF1 | −1.7023 | 1.180672752 |
| CCR2 | −1.6935 | 0.305351506 |
| IFIT3 | −1.6615 | 0.677571172 |
| TNFRSF10A | −1.6615 | 0.230520538 |
| IFNGR1 | −1.6558 | 1.492757528 |
| ITGB2 | −1.6558 | 21.10639135 |
| LYN | −1.6558 | 230.7481187 |
| CCL19 | −1.6358 | 0.131657942 |
| CCL5 | −1.6217 | 1.745561311 |
| RAC1 | −1.5938 | 0.515059945 |
| MALT1 | −1.5883 | 0.281116286 |
| CCL3 | −1.5692 | 0.165855825 |
| CD80 | −1.5665 | 0.132742476 |
| TAP2 | −1.5502 | 0.393041048 |
| ACTB | −1.5369 | 0.382445363 |
| IL8 | −1.5157 | 0.483025481 |
| CCL2 | −1.5105 | 0.134605272 |
| TLR3 | −1.5 | 0.165275956 |
| IL12A | −1.4974 | 0.198792804 |
| FCGR1A | −1.4923 | 0.878361699 |
| NFKB2 | −1.4923 | 0.403365512 |
| EDARADD | −1.4794 | 0.143070569 |
| NOD1 | −1.4768 | 0.308099861 |
| TRAP1 | −1.4439 | 0.483257919 |
| NLRP12 | −1.4439 | 0.363870333 |
| PDIA3 | −1.434 | 0.406179958 |
| IL8 | −1.4216 | 0.354085621 |
| HLA-DQA1 | −1.4167 | 1.178062108 |
| MIF | −1.402 | 1.497615941 |
| RPL13A | −1.3899 | 1.4788335 |
| ITGAM | −1.3779 | 0.600004582 |
| ATF1 | −1.3519 | 0.183064879 |
| CDC42 | −1.3496 | 3.310458234 |
| ICAM2 | −1.3426 | 0.973584543 |
| CCR5 | −1.3333 | 0.145884175 |
| CD44 | −1.3036 | 1.754787134 |
| IL8RA | −1.3013 | 1.145515093 |
| RIPK1 | −1.3013 | 0.462210307 |
| CCR3 | 1.402 | 0.384641887 |
| TLR8 | 1.7471 | 2.50546893 |
| TLR7 | 1.7654 | 0.64730932 |

TABLE 5

Average fold change: Stress-Regulated Genes Involved in Immune System Processes, oxidative stress response and steroid biosythesis. Functions were enriched using hypergeometric statistical analysis along with Bonferroni correction ($p < 0.05$). The significance level and fold change for each gene (obtained from microarray statistical analysis) are shown in the last two columns respectively.

| Gene ID | Name | Description | fold | p-value |
|---|---|---|---|---|
| T-cell activation | | | | |
| AW950965 | CD3E | CD3e, epsilon (CD3-TCR complex) | −1.5 | 9.80E−03 |
| BG333618 | CD74 | CD74, MHC, class II invariant chain | −12.3 | 2.90E−05 |
| AA309971 | LAT | Linker for activation of T cells | −2.9 | 3.10E−04 |
| NM_000887 | ITGAX | Integrin, alpha X (complement component 3 receptor 4 subunit) | −1.4 | 2.10E−02 |
| NM_001767 | CD2 | CD2 molecule | −1.3 | 3.40E−02 |
| AA766638 | PAG1 | Phosphoprotein associated with glycosphingolipid microdomains 1 | −1.5 | 3.10E−02 |
| XM_001772 | LCK | lymphocyte-specific protein tyrosine kinase | −2 | 1.50E−04 |
| NM_000616 | CD4 | CD4 molecule | −2.3 | 1.00E−03 |
| NM_000589 | IL4 | Interleukin 4 | −1.6 | 6.60E−02 |
| NM_002838 | PTPRC | Protein tyrosine | −3.2 | 2.50E−03 |
| BG391140 | CSK | C-src tyrosine kinase | −1.5 | 5.00E−03 |
| XM_006041 | CD5 | CD5 antigen (p56-62) | −2.6 | 3.10E−04 |
| M12824 | CD8A | CD8a molecule | −3.9 | 1.20E−04 |
| BC001257 | GLMN | Glomulin, FKBP associated protein | −1.5 | 1.80E−02 |
| AA310902 | CD3D | CD3d molecule, delta (CD3-TCR complex) | −2.1 | 2.90E−03 |
| AI803460 | CCND3 | Cyclin D3 | −1.5 | 8.80E−03 |
| AC002310 | ITGAL | integrin, alpha L (antigen CD11A (P180), lymphocyte function-associated antigen1; alpha polypeptide) | −1.4 | 7.30E−02 |
| NM_003177 | SYK | Spleen tyrosine kinase | −1.8 | 7.60E−03 |
| NM_000632 | ITGAM | Integrin, alpha M (complement component 3 receptor 3 subunit) | −2.3 | 6.10E−04 |
| U81504 | AP3B1 | Adaptor-related protein complex 3, beta 1 subunit | −1.6 | 1.00E−02 |
| AW780437 | PRKCQ | Protein kinase C, theta | −1.7 | 9.10E−03 |
| AL136450 | BCORL1 | BCL6 co-repressor-like 1 | −1.7 | 3.90E−04 |
| NM_004931 | CD8B | CD8b molecule | −1.5 | 2.50E−03 |
| B cell activation | | | | |
| XM_003106 | PRKCD | protein kinase C, delta | −1.9 | 8.80E−04 |
| AU118181 | KLF6 | Kruppel-like factor 6 | −2.6 | 3.70E−04 |
| NM_000589 | IL4 | Interleukin 4 | −1.6 | 6.60E−02 |
| NM_001250 | CD40 | CD40 molecule, TNF receptor superfamily member | −1.4 | 1.80E−02 |
| L26165 | CDKN1A | Cyclin-dependent kinase inhibitor 1A (p21, Cip1) | −3.8 | 2.90E−05 |
| NM_003177 | SYK | Spleen tyrosine kinase | −1.8 | 7.60E−03 |
| NM_002838 | PTPRC | Protein tyrosine phosphatase, receptor type, C | −3.2 | 2.50E−03 |
| Natural killer cell activation | | | | |
| NM_001767 | CD2 | CD2 molecule | −1.3 | 3.40E−02 |
| AI948861 | SLAMF7 | SLAM family member 7 | −1.7 | 2.50E−02 |

TABLE 5-continued

Average fold change: Stress-Regulated Genes Involved in Immune System Processes, oxidative stress response and steroid biosythesis. Functions were enriched using hypergeometric statistical analysis along with Bonferroni correction (p < 0.05). The significance level and fold change for each gene (obtained from microarray statistical analysis) are shown in the last two columns respectively.

| | | | | |
|---|---|---|---|---|
| AF285436 | KIR3DL1 | Killer cell immunoglobulin-like receptor, three domains, long cytoplasmic tail, 1 | −1.8 | 3.90E−04 |
| AL136450 | BCORL1 | BCL6 co-repressor-like 1 | −1.7 | 3.90E−04 |
| Myeloid dendritic cell activation | | | | |
| NM_001767 | CD2 | CD2 molecule | −1.3 | 3.40E−02 |
| NM_006509 | RELB | V-rel reticuloendotheliosis viral oncogene homolog B, nuclear factor of kappa light polypeptide gene enhancer in B-cells 3 (avian) | −1.9 | 1.30E−04 |
| Mast cell activation | | | | |
| AA309971 | LAT | Linker for activation of T cells | −2.9 | 3.10E−04 |
| AF177765 | TLR4 | toll-like receptor 4 (TLR4) | −1.8 | 9.60E−03 |
| NM_005565 | LCP2 | Lymphocyte cytosolic protein 2 (SH2 domain containing leukocyte protein of 76 kDa) | −2.5 | 9.30E−04 |
| NM_003177 | SYK | Spleen tyrosine kinase | −1.8 | 7.60E−03 |
| Macrophage activation | | | | |
| BG333618 | CD74 | CD74; MHC, class II invariant chain | −12.3 | 2.90E−05 |
| AI937452 | CD93 | CD93 molecule | −1.6 | 5.60E−04 |
| AF177765 | TLR4 | toll-like receptor 4 (TLR4) | −1.8 | 9.60E−03 |
| Platelete activation | | | | |
| AI739539 | PF4 | Platelet factor 4 (chemokine (C-X-C motif) ligand 4) | −3.3 | 1.10E−04 |
| NM_001250 | CD40 | CD40 molecule, TNF receptor superfamily member | −1.4 | 1.80E−02 |
| T-cell differentiation | | | | |
| BG333618 | CD74 | CD74; MHC, class II invariant chain | −12.3 | 2.90E−05 |
| AW950965 | CD3E | CD3e; epsilon (CD3-TCR complex) | −1.5 | 9.80E−03 |
| M12824 | CD8A | CD8a molecule | −3.9 | 1.20E−04 |
| NM_001767 | CD2 | CD2 molecule | −1.3 | 3.40E−02 |
| AA310902 | CD3D | CD3d; delta (CD3-TCR complex) | −2.1 | 2.90E−04 |
| XM_001772 | LCK | lymphocyte-specific protein tyrosine kinase | −2 | 1.50E−04 |
| NM_000616 | CD4 | CD4 molecule | −2.3 | 1.00E−03 |
| NM_003177 | SYK | Spleen tyrosine kinase | −1.8 | 7.60E−03 |
| U81504 | AP3B1 | Adaptor-related protein complex 3, beta 1 subunit | −1.6 | 1.00E−02 |
| NM_002838 | PTPRC | Protein tyrosine phosphatase, receptor type, C | −3.2 | 2.50E−03 |

TABLE 5-continued

Average fold change: Stress-Regulated Genes Involved in Immune System Processes, oxidative stress response and steroid biosythesis. Functions were enriched using hypergeometric statistical analysis along with Bonferroni correction (p < 0.05). The significance level and fold change for each gene (obtained from microarray statistical analysis) are shown in the last two columns respectively.

| | | | | |
|---|---|---|---|---|
| B cell differentiation | | | | |
| AU118181 | KLF6 | Kruppel-like factor 6 | −2.6 | 3.70E−04 |
| NM_000589 | IL4 | Interleukin 4 | −1.6 | 6.60E−02 |
| NM_003177 | SYK | Spleen tyrosine kinase | −1.8 | 7.60E−03 |
| NK T cell differentiation | | | | |
| U81504 | AP3B1 | Adaptor-related protein complex 3, beta 1 subunit | −1.6 | 1.00E−02 |
| Monocyte differentiation | | | | |
| BG434340 | IFI16 | Interferon, gamma-inducible protein 16 | −1.7 | 2.70E−03 |
| NM_002473 | MYH9 | Myosin, heavy chain 9, non-muscle | −3.4 | 2.00E−05 |
| Myeloid cell differentiation | | | | |
| AA777633 | MYST3 | MYST histone acetyltransferase (monocytic leukemia) 3 | −1.6 | 3.30E−03 |
| AL551154 | HCLS1 | Hematopoietic cell-specific Lyn substrate 1 | −7 | 2.20E−06 |
| AI739539 | PF4 | Platelet factor 4 (chemokine (C-X-C motif) ligand 4) | −3.3 | 1.10E−04 |
| Y14768 | TNFA | TNF-alpha | −1.3 | 9.90E−03 |
| BG108304 | LYN | V-yes-1 Yamaguchi sarcoma viral related oncogene homolog | −3.2 | 4.50E−05 |
| XM_008993 | SPIB | Spi-B transcription factor (Spi-1/PU.1 related) | −1.5 | 1.40E−03 |
| AF177765 | TLR4 | toll-like receptor 4 (TLR4) | −1.8 | 9.60E−03 |
| NM_000589 | IL4 | Interleukin 4 | −1.6 | 6.60E−02 |
| AA583143 | MAFB | V-maf musculoaponeurotic fibrosarcoma oncogene homolog B (avian) | −2.7 | 1.00E−04 |
| NM_006509 | RELB | V-rel reticuloendotheliosis viral oncogene homolog B, nuclear factor of kappa light polypeptide gene enhancer in B-cells 3 (avian) | −1.9 | 1.30E−04 |
| AA253017 | MYST1 | MYST histone acetyltransferase 1 | −1.5 | 5.70E−02 |
| T cell proliferation | | | | |
| AW950965 | CD3E | CD3e molecule, epsilon (CD3-TCR complex) | −1.5 | 9.80E−03 |
| NM_000887 | ITGAX | Integrin, alpha X (complement component 3 receptor 4 subunit) | −1.4 | 2.10E−02 |
| BC001257 | GLMN | Glomulin, FKBP associated protein | −1.5 | 1.80E−02 |
| AI803460 | CCND3 | Cyclin D3 | −1.5 | 8.80E−03 |
| AC002310 | ITGAL | integrin, alpha 1 (antigen CD11A (P180), lymphocyte function-associated antigen 1; alpha polypeptide) | −1.4 | 7.30E−02 |

TABLE 5-continued

Average fold change: Stress-Regulated Genes Involved in Immune System Processes, oxidative stress response and steroid biosythesis. Functions were enriched using hypergeometric statistical analysis along with Bonferroni correction (p < 0.05). The significance level and fold change for each gene (obtained from microarray statistical analysis) are shown in the last two columns respectively.

| Accession | Symbol | Description | Fold | p-value |
|---|---|---|---|---|
| NM_000589 | IL4 | Interleukin 4 | −1.6 | 6.60E−02 |
| NM_003177 | SYK | Spleen tyrosine kinase | −1.8 | 7.60E−03 |
| NM_000632 | ITGAM | Integrin, alpha M (complement component 3 receptor 3 subunit) | −2.3 | 6.10E−04 |
| NM_002838 | PTPRC | Protein tyrosine phosphatase, receptor type, C | −3.2 | 2.50E−03 |
| AW780437 | PRKCQ | Protein kinase C, theta | −1.7 | 9.10E−03 |
| AL136450 | BCORL1 | BCL6 co-repressor-like 1 | −1.7 | 3.90E−04 |
| | | B cell proliferation | | |
| XM_003106 | PRKCD | protein kinase C, delta | −1.9 | 8.80E−04 |
| NM_000589 | IL4 | Interleukin 4 | −1.6 | 6.60E−02 |
| NM_001250 | CD40 | CD40 molecule, TNF receptor superfamily member | −1.4 | 1.80E−02 |
| L26165 | CDKN1A | Cyclin-dependent kinase inhibitor 1A (p21, Cip1) | −3.8 | 2.90E−05 |
| NM_002838 | PTPRC | Protein tyrosine phosphatase, receptor type, C | −3.2 | 2.50E−03 |
| | | activated T cell proliferation | | |
| NM_000887 | ITGAX | Integrin, alpha X (complement component 3 receptor 4 subunit) | −1.4 | 2.10E−02 |
| AC002310 | ITGAL | integrin, alpha 1 (antigen CD11A (P180), lymphocyte function-associated antigen 1; alpha polypeptide) | −1.4 | 7.30E−02 |
| NM_000589 | IL4 | Interleukin 4 | −1.6 | 6.60E−02 |
| NM_000632 | ITGAM | Integrin, alpha M (complement component 3 receptor 3 subunit) | −2.3 | 6.10E−04 |
| | | NK cell proliferation | | |
| AL136450 | BCORL1 | BCL6 co-repressor-like 1 | −1.7 | 3.90E−04 |
| | | microbial pattern recognition and binding | | |
| AI739539 | PF4 | Platelet factor 4 (CXCL4) | −3.3 | 1.10E−04 |
| AI097512 | CHIT1 | Chitinase 1 (chitotriosidase) | −1.5 | 2.00E−02 |
| NM_003264 | TLR2 | Toll-like receptor 2 | −2.6 | 1.00E−03 |
| AF177765 | TLR4 | toll-like receptor 4 (TLR4) | −1.8 | 9.60E−03 |
| XM_012649 | SCYA7 | Small inducible cytokine A7 (monocyte chemotactic | −1.5 | 2.80E−02 |
| AL549182 | CD14 | CD14 molecule | −3.5 | 8.20E−06 |
| NM_002620 | PF4V1 | Platelet factor 4 variant 1 | −2.7 | 1.90E−03 |
| AA188236 | CLP1 | CLP1, cleavage and polyadenylation factor I subunit, homolog (*S. cerevisiae*) | −1.5 | 1.60E−02 |
| AI087056 | TICAM1 | Toll-like receptor adaptor molecule 1 | −1.5 | 3.30E−03 |
| AF054013 | FPRL1 | Formyl peptide receptor-like 1 | −1.9 | 2.40E−03 |
| L10820 | FPR1 | Human N-formyl peptide receptor | −1.8 | 3.10E−05 |
| | | antigen processing and presentation | | |
| BG333618 | CD74 | CD74; MHC, class II invariant chain | −12.3 | 2.90E−05 |
| BF795929 | HLA-DRA | MHC, class II, DR alpha | −8.3 | 1.20E−05 |
| U83582 | HLA-DQB1 | MHC, class II, DQ beta 1 | −2 | 5.20E−05 |
| AI634950 | IGHG1 | Ig heavy constant gamma1 (G1m marker) | −11.8 | 6.20E−08 |
| AL571972 | FCGRT | Fc fragment of IgG, receptor, transporter, alpha | −1.6 | 5.10E−02 |
| AV759427 | HLA-DPA1 | MHC, class II, DP alpha 1 | −6.8 | 2.70E−06 |
| M83664 | HLA-DPB1 | MHC, class II, DP beta 1 | −2.8 | 6.30E−06 |
| AL561631 | IFI30 | Interferon, gamma-inducible protein 30 | −2.6 | 2.80E−03 |
| NM_006674 | MICA | MHC class I polypeptide-related sequence A | −2.2 | 2.50E−03 |
| BG327758 | HLA-B | MHC, class I, B | — | 2.70E−06 |
| AF071019 | HLA-G | HLA-G histocompatibility antigen, class I, G | −2.4 | 2.60E−06 |
| BF663123 | IGHA1 | Ig heavy constant alpha 1 | −2.5 | 2.80E−03 |
| AW407113 | HLA-C | MHC, class I, C | −5.3 | 6.50E−07 |
| BG176768 | HLA-DOB | MHC, class II, DO beta | −2.4 | 1.60E−04 |
| NM_006509 | RELB | Nuclear factor of kappa light polypeptide gene enhancer in B-cells 3 | −1.9 | 1.30E−04 |
| M20503 | HLA-DRB1 | MHC, class II, DR beta 1 | −11.8 | 5.30E−06 |
| U81504 | AP3B1 | Adaptor-related protein complex 3, beta 1 subunit | −1.6 | 1.00E−02 |
| AV710740 | B2M | Beta-2-microglobulin | −3.9 | 4.30E−08 |
| | | cytokine activity | | |
| XM_003506 | PPBP | pro-platelet basic protein (includes platelet basic | −4.1 | 8.10E−05 |
| AI739539 | PF4 | Platelet factor 4 (chemokine (C-X-C motif) ligand 4) | −3.3 | 1.10E−04 |
| Y14768 | TNFA | TNF-alpha | −1.3 | 9.90E−03 |
| XM_003507 | SCYB5 | Small inducible cytokine subfamily B (Cys-X-Cys), | −5.2 | 4.90E−05 |
| XM_005349 | TNFSF8 | tumor necrosis factor (ligand) superfamily, member 8 | −1.9 | 1.50E−03 |
| W38319 | IL1B | Interleukin 1, beta | −6.3 | 2.70E−07 |
| NM_002988 | CCL18 | Chemokine (C-C motif) ligand 18 (pulmonary and activation-regulated) | −1.6 | 1.20E−03 |
| AV717082 | IL8 | Interleukin 8 | — | 3.20E−04 |
| BG108304 | LYN | V-yes-1 Yamaguchi sarcoma viral related oncogene homolog | −3.2 | 4.50E−05 |

TABLE 5-continued

Average fold change: Stress-Regulated Genes Involved in Immune System Processes, oxidative stress response and steroid biosythesis. Functions were enriched using hypergeometric statistical analysis along with Bonferroni correction (p < 0.05). The significance level and fold change for each gene (obtained from microarray statistical analysis) are shown in the last two columns respectively.

| Accession | Symbol | Description | Fold | p-value |
|---|---|---|---|---|
| XM_012649 | SCYA7 | small inducible cytokine A7 (monocyte chemotactic | −1.5 | 2.80E−02 |
| NM_000589 | IL4 | Interleukin 4 | −1.6 | 6.60E−02 |
| NM_000575 | IL1A | Interleukin 1, alpha | −5.2 | 2.30E−05 |
| XM_003508 | GRO3 | GRO3 oncogene | −1.5 | 2.10E−02 |
| AA569974 | CCL5 | Chemokine (C-C motif) ligand 5 | −1.6 | 4.30E−03 |
| NM_005408 | CCL13 | Chemokine (C-C motif) ligand 13 | −1.6 | 1.90E−02 |
| BG288796 | IL1RN | Interleukin 1 receptor antagonist | −3.6 | 3.90E−04 |
| AW188005 | LTB | Lymphotoxin beta (TNF superfamily, member 3) | −3.2 | 1.00E−03 |
| BC001257 | GLMN | Glomulin, FKBP associated protein | −1.5 | 1.80E−02 |
| AW965098 | CCL20 | Chemokine (C-C motif) ligand 20 | −1.5 | 4.30E−03 |
| BG393056 | PRL | Prolactin | −1.5 | 1.40E−02 |
| BG491425 | CXCL1 | Chemokine (C-X-C motif) ligand 1 (melanoma growth stimulating activity, alpha) | −15.2 | 6.90E−06 |
| NM_002620 | PF4V1 | Platelet factor 4 variant 1 | −2.7 | 1.90E−03 |
| cytokine binding (receptors) | | | | |
| AF009962 | CCR-5 | CC-chemokine receptor (CCR-5) | −1.5 | 1.00E−02 |
| NM_000877 | IL1R1 | Interleukin 1 receptor, type I | −1.5 | 3.40E−02 |
| NM_000418 | IL4R | Interleukin 4 receptor | −1.6 | 9.40E−03 |
| XM_008651 | CCR7 | Chemokine (C-C motif) receptor 7 | −17 | 4.30E−08 |
| NM_001558 | IL10RA | Interleukin 10 receptor, alpha | −1.6 | 1.20E−02 |
| NM_000878 | IL2RB | Interleukin 2 receptor, beta | −2.7 | 6.30E−06 |
| AF012629 | TNFRSF10C | Tumor necrosis factor receptor superfamily, member 10c, decoy without an intracellular domain | −1.7 | 2.30E−03 |
| XM_001743 | TNFRSF1B | Tumor necrosis factor receptor superfamily, member 1B | −2.4 | 1.80E−03 |
| BC001281 | TNFRSF10B | Tumor necrosis factor receptor superfamily, member 10b | −1.5 | 3.60E−03 |
| NM_001250 | CD40 | CD40 molecule, TNF receptor superfamily member | −1.4 | 1.80E−02 |
| AL050337 | IFNGR1 | interferon gamma receptor 1 | −1.6 | 6.20E−03 |
| AL550285 | IFNGR2 | Interferon gamma receptor 2 (interferon gamma transducer 1) | −1.8 | 6.50E−03 |
| IL-12 biosynthesis | | | | |
| NM_003998 | NFKB1 | Nuclear factor of kappa light polypeptide gene enhancer in B-cells 1 (p105) | −3.7 | 5.20E−05 |
| NM_002198 | IRF1 | Interferon regulatory factor 1 | −2.2 | 4.50E−04 |
| AF177765 | TLR4 | toll-like receptor 4 (TLR4) | −1.8 | 9.60E−03 |
| IL-6 biosynthesis | | | | |
| W39546 | CEBPB | CCAAT/enhancer binding protein (C/EBP), beta | −1.9 | 5.30E−03 |
| W38319 | IL1B | Interleukin 1, beta | −6.3 | 2.70E−07 |
| AF177765 | TLR4 | toll-like receptor 4 (TLR4) | −1.8 | 9.60E−03 |
| IL-2 biosynthesis | | | | |
| BC001257 | GLMN | Glomulin, FKBP associated protein | −1.5 | 1.80E−02 |
| NM_000616 | CD4 | CD4 molecule | −2.3 | 1.00E−03 |
| AW780437 | PRKCQ | Protein kinase C, theta | −1.7 | 9.10E−03 |
| IL-3 biosynthesis | | | | |
| NM_003177 | SYK | Spleen tyrosine kinase | −1.8 | 7.60E−03 |
| IL-1 biosynthesis | | | | |
| AF177765 | TLR4 | toll-like receptor 4 (TLR4) gene, | −1.8 | 9.60E−03 |
| inflammatory response | | | | |
| AL570708 | CD180 | CD180 molecule | −1.3 | 1.50E−02 |
| AL549182 | CD14 | CD14 molecule | −3.5 | 8.20E−06 |
| U08198 | C8G | Human complement C8 gamma subunit precursor (C8G) gene, complete cds. | −1.5 | 4.00E−03 |
| NM_003264 | TLR2 | Toll-like receptor 2 | −2.6 | 1.00E−03 |
| XM_006848 | KRT1 | keratin 1 (epidermolytic hyperkeratosis) | −2 | 1.70E−03 |
| NM_001250 | CD40 | CD40 molecule, TNF receptor superfamily member | −1.4 | 1.80E−02 |
| NM_004029 | IRF7 | Interferon regulatory factor 7 | −2.2 | 5.60E−04 |
| W39546 | CEBPB | CCAAT/enhancer binding protein (C/EBP), beta | −1.9 | 5.30E−03 |
| X04011 | CYBB | Cytochrome b-245, beta polypeptide (chronic granulomatous disease) | −1.6 | 3.20E−03 |
| AF177765 | TLR4 | toll-like receptor 4 (TLR4) | −1.8 | 9.60E−03 |
| AI090294 | CD97 | CD97 molecule | −1.7 | 1.90E−04 |
| NM_003998 | NFKB1 | Nuclear factor of kappa light polypeptide gene enhancer in B-cells 1 (p105) | −3.7 | 5.20E−05 |
| NM_000211 | ITGB2 | Integrin, beta 2 (complement component 3 receptor 3 and 4 subunit) | −2.2 | 6.30E−06 |

TABLE 5-continued

Average fold change: Stress-Regulated Genes Involved in Immune System Processes, oxidative stress response and steroid biosynthesis. Functions were enriched using hypergeometric statistical analysis along with Bonferroni correction ($p < 0.05$). The significance level and fold change for each gene (obtained from microarray statistical analysis) are shown in the last two columns respectively.

| ID | Name | Description | Fold | P-value |
|---|---|---|---|---|
| AC002310 | ITGAL | integrin, alpha 1 (antigen CD11A (P180), lymphocyte function-associated antigen 1; alpha polypeptide) | −1.4 | 7.30E−02 |
| *Cholesterol and other steroids biosynthesis* | | | | |
| AL558223 | ACBD3 | Acyl-Coenzyme A binding domain containing 3 | 1.6 | 4.10E−03 |
| BE253839 | DHCR24 | 24-dehydrocholesterol reductase | 2.1 | 1.60E−02 |
| AW271546 | HSD17B1 | Hydroxysteroid (17-beta) dehydrogenase 1 | 1.6 | 2.50E−03 |
| AF078850 | HSD17B12 | Hydroxysteroid (17-beta) dehydrogenase 12 | 1.4 | 1.70E−02 |
| AK001889 | PRLR | Prolactin receptor | 1.9 | 5.00E−03 |
| NM_000786 | CYP51A1 | Cytochrome P450, family 51, subfamily A, polypeptide 1 | 1.9 | 3.90E−04 |
| NM_004110 | FDXR | Ferredoxin reductase | 1.8 | 5.00E−03 |
| NM_000103 | CYP19A1 | Cytochrome P450, family 19, subfamily A, polypeptide 1 | 1.9 | 1.60E−02 |
| BE378962 | DHCR7 | 7-dehydrocholesterol reductase | 1.8 | 2.60E−03 |
| J05158 | CPN2 | Carboxypeptidase N, polypeptide 2, 83 kD | 1.9 | 2.10E−03 |
| AL521605 | OPRS1 | Opioid receptor, sigma 1 | 2.2 | 4.70E−04 |
| AW117731 | HMGCS1 | 3-hydroxy-3-methylglutaryl-Coenzyme A synthase 1 (soluble) | 2.2 | 2.00E−03 |
| BG324529 | MVD | Mevalonate (diphospho) decarboxylase | 2.3 | 5.20E−03 |
| *Ergosterol biosynthesis* | | | | |
| AL521605 | OPRS1 | Opioid receptor, sigma 1 | 2.2 | 4.70E−04 |
| *Dopamine biosynthesis* | | | | |
| AW156890 | SNCA | Synuclein, alpha (non A4 component of amyloid precursor) | 1.5 | 1.20E−02 |
| *Fatty acid biosynthesis* | | | | |
| AL359403 | MCAT | Malonyl CoA: ACP acyltransferase (mitochondrial) | 1.6 | 5.40E−03 |
| AF097514 | SCD | Stearoyl-CoA desaturase (delta-9-desaturase) | 5.2 | 4.40E−04 |
| *transcription Transcription factors* | | | | |
| BE266904 | SATB1 | Special AT-rich sequence binding protein 1 | −4.2 | 1.70E−06 |
| NM_006763 | BTG2 | BTG family, member 2 | −3.8 | 7.70E−04 |
| NM_003998 | NFKB1 | NFk light polypeptide gene enhancer in B-cells 1 (p105) | −3.7 | 7.00E−05 |
| AI348005 | BTG1 | B-cell translocation gene 1, anti-proliferative | −3.4 | 3.70E−05 |
| NM_006060 | IKZF1 | IKAROS family zinc finger 1 (Ikaros) | −2.6 | 7.00E−05 |
| AL555297 | SF1 | Splicing factor 1 | −2.4 | 1.70E−06 |
| NM_014795 | ZFHX1B | Zinc finger homeobox 1b | −2.3 | 6.10E−04 |
| AL561046 | TSC22D3 | TSC22 domain family, member 3 | −2.2 | 5.00E−04 |
| NM_002198 | IRF1 | Interferon regulatory factor 1 | −2.2 | 5.00E−04 |
| NM_004029 | IRF7 | Interferon regulatory factor 7 | −2.2 | 5.80E−04 |
| AV708340 | UBA52 | Ubiquitin A-52 residue ribosomal protein fusion product 1 | −2.1 | 6.80E−04 |
| AI631717 | HNF4A | Hepatocyte nuclear factor 4, alpha | 2 | 3.90E−03 |
| BG529476 | HMGB2 | High-mobility group box 2 | 2.1 | 2.50E−03 |
| BG340581 | SREBF2 | Sterol regulatory element binding transcription factor 2 | 2.3 | 1.50E−03 |
| AL525810 | FOXM1 | Forkhead box M1 | 2.3 | 2.40E−04 |
| M95585 | HLF | Hepatic leukemia factor | 2.4 | 5.00E−04 |
| NM_003220 | TFAP2A | Transcription factor AP-2 alpha | 2.4 | 2.00E−03 |
| AL575644 | NFKBIL1 | NFk light polypeptide enhancer in B-cells inhibitor-like 1 | 3.3 | 4.60E−03 |
| *Ssuperoxide metabolism* | | | | |
| BG035651 | SOD2 | Superoxide dismutase 2, mitochondrial | −10.3 | 1.20E−07 |
| BG421245 | CYBA | Cytochrome b-245, alpha polypeptide | −2.1 | 1.00E−06 |
| XM_002200 | NCF2 | neutrophil cytosolic factor 2 (65 kD, chronic | −2 | 2.90E−04 |
| *heat Heat shock proteins* | | | | |
| BG327949 | HSP90B1 | Heat shock protein 90 kDa beta (Grp94), member 1 | 1.6 | 4.50E−02 |
| AB007877 | HSPA12A | Heat shock 70 kDa protein 12A | 1.7 | 2.10E−03 |
| BE742483 | HSPA4 | Heat shock 70 kDa protein 4 | 1.9 | 1.00E−05 |
| AI640615 | BAG4 | BCL2-associated athanogene 4 | 1.9 | 1.10E−03 |
| BG032173 | HSPD1 | Heat shock 60 kDa protein 1 (chaperonin) | 2.5 | 5.90E−04 |

Example 1

The biomarker findings are presented which were identified from gene expression changes in leukocytes collected from (informed and consented) US Army Ranger Cadets who underwent eight-weeks of Army Ranger Training (RASP, Ranger Assessment and Selection Program). Our subjects were exposed to extreme physical and psychological stressors of Ranger Training, which is designed to emulate extreme battlefield scenarios such as strenuous physical activity, sleep deprivation, calorie restriction, and survival emotional stresses—pushing cadets to their physical and psychological limits. Though these men were among the best of the best, many trainees dropped out in the first phase of the three-phased RASP Training. The Army Ranger population provides a rare opportunity to study extreme stress, and to contribute to the understanding of intense chronic stress in general. Particularly, the ability to collect pre-training samples for comparison with post-training samples is rarely practical in any other chronically and extremely stressed patients.

Our studies focus in identifying molecular mediators of compromised protective immunity caused by social and battlefield-like stresses, and in identifying pathogen-induced biomarkers under severe stress background. Social and physiological stresses, particularly, which are frequent or chronic are major contributors of stress-induced immune dysfunction. In this study, we employed experimental and computational approaches to identify molecules and signaling pathways involved in the host's response towards battlefield-like stress, and in assessing protective immunity status of the stressed host towards infection.

In the first approach, we used genome-wide transcriptome, and microRNA profiling and in-vitro pathogen exposure of leukocytes (isolated from Army Ranger Trainees) to identify stress-suppressed transcripts and pathways critical in protective immune response. We have identified a number of stress response biomarkers (transcripts and pathways) that have potential implication in compromising the immune function. The most compromised pathways include antigen preparation and presentation, and T-cell activation pathways. Suppressed immune response genes remained suppressed even after ex-vivo exposure of post-RASP leukocytes to the mitogenic toxin, Staphylococcal enterotoxin B (SEB). On the other hand, complete and differential counts of post-training WBCs were within normal ranges. This impaired activation is an indicator of anergy, and compromised protective immunity.

Example 2

In the second approach, we used rigorous computational analyses in identifying up-stream regulatory modules (and molecular networks) of stress-suppressed genes. We identified up-stream regulators of differentially altered transcripts, which include immune related and steroid hormone inducible transcription factors, stress response factors, and microRNAs. Some stress induced microRNAs, and a number of stress-inhibited transcription factors were found to regulate or be modulated by many compromised immune response transcripts.

The identification of exceptionally enriched suppression of antigen presentation and lymphocyte activation pathways (in spite of normal blood cell counts) are remarkable since these findings are consistent with prior observations of poor vaccine responses, impaired wound healing and infection susceptibility associated with chronic intense stress.

Some of the transcripts were unique to RASP stressors (severe and chronic stress), even in the presence of other pathogens, to which we briefly refer in this manuscript. These specific transcripts may have potential use as diagnostic markers to distinguish debilitating chronic stress from that of infection.

CONCLUSION

The subject matter of the present invention (biomarkers) solves the drawbacks of other routinely used assays that check the status of the immune system process. Many clinical laboratories do differential and complete white blood cell counting to ascertain integrity of the immune system. Some advanced clinical laboratories do challenge assays (proliferation assays) to check the viability of immune cells (in addition to cell counting). In our case, even though the cells are within their normal ranges (cell counting would have indicated normal), we still see no measurable response to SEB challenge (and we have the molecular indicators of the why). Our molecular markers can be used to check the protective or compromised nature of the immune system regardless of whether the cells are anergic (within normal range in terms of their numbers but not protective) or otherwise.

DEFINITIONS

Welch's t-test: Statistical comparative analysis whereby the means and variance of compared groups are not assumed to be the equal.
Transcriptome: Genome-wide transcripts of human or any other living thing.
Transcript: Messenger RNA (ribonucleic acid) or any other small RNA molecule.
Pathway: regulatory hierarchy of bio-molecules (proteins, transcripts, or metabolites) forming a specific biological process (function).
Normal Control: A person or sample from a person, or genes or transcripts from a person, or expression profile from a person or persons that has not been subjected to stress.
Diagnostic biomarkers: stress effected genes, transcripts, cDNAs, mRNA, miRNAs, rRNA, tRNA, peptides and proteins.
**Gene names and accession numbers presented herein are standard gene names and accession numbers for genes that are found in the NCBI GenBank®. GenBank® is the NIH genetic sequence database, an annotated collection of all publicly available DNA sequences (Nucleic Acids Research, 2013 January; 41(D1):D36-42). GenBank is part of the International Nucleotide Sequence Database Collaboration, which comprises the DNA DataBank of Japan (DDBJ), the European Molecular Biology Laboratory (EMBL), and GenBank at NCBI. These three organizations exchange data on a daily basis.

REFERENCES

1. Cohen S, Janicki-Deverts D & Miller G E. Psychological stress and disease. *JAMA* 2007; 298(14): 1685-1687.
2. Rokutan K, Morita K, Masuda K, Tominaga K, Shikishima M, Teshima-Kondo S et al. Gene expression profiling in peripheral blood leukocytes as a new approach for assessment of human stress response. *J Med Invest* 2005; 52(3-4): 137-144.
3. Motoyama K, Nakai Y, Miyashita T, Fukui Y, Morita M, Sanmiya K et al. Isolation stress for 30 days alters hepatic gene expression profiles, especially with reference to lipid metabolism in mice. *Physiol Genomics* 2009; 37(2): 79-87.
4. Zhang Y, Miao J, Hanley G, Stuart C, Sun X, Chen T et al. Chronic restraint stress promotes immune suppression through toll-like receptor 4-mediated phosphoinositide 3-kinase signaling. *J Neuroimmunol* 2008; 204(1-2): 13-19.
5. Padgett D A & Glaser R. How stress influences the immune response. *Trends in Immunology* 2003; 24(8): 444-448.

6. Kiecolt-Glaser J K, Glaser R, Gravenstein S, Malarkey W B & Sheridan J. Chronic stress alters the immune response to influenza virus vaccine in older adults. *Pro Nat Acad Sci (USA)* 1996; 93(7): 3043-3047.
7. Tournier J N, Mathieu J, Mailfert Y, Multon E, Drouet C, Jouan A et al. Chronic restraint stress induces severe disruption of the T-cell specific response to tetanus toxin vaccine. *Immunology* 2001; 102(1): 87-93.
8. Li J, Cowden L G, King J D, Briles D A, Schroeder H W, Stevens A B et al. Effects of chronic stress and interleukin-10 gene polymorphisms on antibody response to tetanus vaccine in family caregivers of patients with Alzheimer's disease. *Psychosom Med* 2007; 69(6): 551-559.
9. Glaser R, Sheridan J, Malarkey W B, MacCallum R C & Kiecolt-Glaser J K. Chronic stress modulates the immune response to a pneumococcal pneumonia vaccine. *Psychosom Med* 2000; 62(6): 804-807.
10. Kiank C, Holtfreter B, Starke A, Mundt A, Wilke C & Schutt C. Stress susceptibility predicts the severity of immune depression and the failure to combat bacterial infections in chronically stressed mice. *Brain Behav Immun* 2006; 20(4): 359-368.
11. Reiche E M, Nunes S O & Morimoto H K. Stress, depression, the immune system, and cancer. *Lancet Oncol* 2004; 5(10): 617-625.
12. Friedl K E, Moore R J, Hoyt R W, Marchitelli L J, Martinez-Lopez L E & Askew E W. Endocrine markers of semistarvation in healthy lean men in a multistressor environment. *J Appl Physiol* 2000; 88(5): 1820-1830.
13. Nindl B C, Barnes B R, Alemany J A, Frykman P N, Shippee R L & Friedl K E. Physiological consequences of U.S. Army Ranger training. *Med Sci Sports Exerc* 2007; 39(8): 1380-1387.
14. Mendis C, Das R, Hammamieh R, Royaee A, Yang D, Peel S et al. Transcriptional response signature of human lymphoid cells to staphylococcal enterotoxin B. *Genes Immun* 2005; 6(2): 84-94.
15. Paik I H, Toh K Y, Lee C, Kim J J & Lee S J. Psychological stress may induce increased humoral and decreased cellular immunity. *Behav Med* 2000; 26(3): 139-141.
16. Glaser R, MacCallum R C, Laskowski B F, Malarkey W B, Sheridan J F & Kiecolt-Glaser J K. Evidence for a shift in the Th-1 to Th-2 cytokine response associated with chronic stress and aging. *J Gerontol Ser A-Biol Sci Med Sci* 2001; 56(8): M477-M482.
17. O'Connell R M, Kahn D, Gibson W S, Round J L, Scholz R L, Chaudhuri A A et al. MicroRNA-155 promotes autoimmune inflammation by enhancing inflammatory T cell development. *Immunity;* 33(4): 607-619.
18. Kurowska-Stolarska M, Alivernini S, Ballantine L E, Asquith D L, Millar N L, Gilchrist D S et al. MicroRNA-155 as a proinflammatory regulator in clinical and experimental arthritis. *Proc Natl Acad Sci USA;* 108(27): 11193-11198.
19. Das R, Hammamieh R, Neill R, Ludwig G V, Eker S, Lincoln P et al. Early indicators of exposure to biological threat agents using host gene profiles in peripheral blood mononuclear cells. *BMC Infect Dis* 2008; 8: 104.
20. Marinescu V D, Kohane, I. S., and Riva, A. (2005). The MAPPER database: a multi-genome catalog of putative transcription factor binding sites. In: *Nucleic Acids Res* pp D91-97.
21. Christin C, Hoefsloot H C, Smilde A K, Hoekman B, Suits F, Bischoff R et al. A critical assessment of feature selection methods for biomarker discovery in clinical proteomics. *Mol Cell Proteomics;* 12(1): 263-276.
22. Wang S & Zhu J. Improved centroids estimation for the nearest shrunken centroid classifier. *Bioinformatics* 2007; 23(8): 972-979.
23. Tibshirani R, Hastie T, Narasimhan B & Chu G. Diagnosis of multiple cancer types by shrunken centroids of gene expression. *Proc Natl Acad Sci USA* 2002; 99(10): 6567-6572.
24. Sharma P, Sahni N S, Tibshirani R, Skaane P, Urdal P, Berghagen H et al. Early detection of breast cancer based on gene-expression patterns in peripheral blood cells. *Breast Cancer Res* 2005; 7(5): R634-644.
25. Shankavaram U T, Reinhold W C, Nishizuka S, Major S, Morita D, Chary K K et al. Transcript and protein expression profiles of the NCI-60 cancer cell panel: an integromic microarray study. *Mol Cancer Ther* 2007; 6(3): 820-832.
26. Selaru F M, Wang S, Yin J, Schulmann K, Xu Y, Mori Y et al. Beyond Field Effect: Analysis of Shrunken Centroids in Normal Esophageal Epithelia Detects Concomitant Esophageal Adenocarcinoma. *Bioinform Biol Insights* 2007; 1: 127-136.
27. Suarez-Farinas M, Shah K R, Haider A S, Krueger J G & Lowes M A. Personalized medicine in psoriasis: developing a genomic classifier to predict histological response to Alefacept. *BMC Dermatol;* 10:1.

What is claimed is:

1. A method for detecting a subset of messenger RNA (mRNA) in a subject method comprising:
 (a) obtaining a sample from the subject,
  wherein the sample comprises whole blood;
 (b) isolating total RNA from the sample,
  wherein the total RNA comprises a subset of messenger RNA (mRNA);
 (c) determining the level of a subset of mRNA in the sample,
  wherein the subset of mRNA consists of CCR7, IGHG1, CSPG2, LAPTM5, CSF1R, ALB, HLA-C, HLA-DRA, HLA-DPA1, CD14, LOC652128, MGAT1, HCLS1, ANPEP, IL1B, SATB1, LCP1, AQP9, and HLA-DRB1.

2. The method of claim 1, wherein leukocytes are isolated from the whole blood sample.

3. The method of claim 1, wherein the method further comprises producing cDNA from the isolated mRNA.

4. The method of claim 1, wherein the method further comprises detecting the subset set of mRNA using a microarray.

5. The method of claim 4, wherein the microarray is a cDNA microarray.

* * * * *